(12) United States Patent
Vermaas et al.

(10) Patent No.: US 12,584,169 B2
(45) Date of Patent: \*Mar. 24, 2026

(54) COMPOSITIONS AND METHODS FOR IMPROVING SAMPLE IDENTIFICATION IN INDEXED NUCLEIC ACID LIBRARIES

(71) Applicants:Illumina, Inc., San Diego, CA (US); Illumina Cambridge Limited, Cambridge (GB)

(72) Inventors: Eric Vermaas, San Diego, CA (US); Mahdieh Khosroheidari, San Diego, CA (US); Angela Kalbande, San Diego, CA (US); Vincent Peter Smith, Cambridge (GB); Claire Bevis-Mott, Cambridge (GB); Jonathan Mark Boutell, Cambridge (GB); Michael Chesney, Cambridge (GB)

(73) Assignees: Illumina, Inc., San Diego, CA (US); Illumina Cambridge Limited (GB)

( \* ) Notice: Subject to any disclaimer, the term of this patent is extended or adjusted under 35 U.S.C. 154(b) by 1382 days.

This patent is subject to a terminal disclaimer.

(21) Appl. No.: 17/227,639

(22) Filed: Apr. 12, 2021

(65) Prior Publication Data

US 2021/0230689 A1 Jul. 29, 2021

Related U.S. Application Data

(60) Continuation-in-part of application No. 17/181,271, filed on Feb. 22, 2021, now Pat. No. 12,247,254, and
(Continued)

(51) Int. Cl.
C12Q 1/6874 (2018.01)
C12Q 1/6806 (2018.01)
(Continued)

(52) U.S. Cl.
CPC ......... C12Q 1/6874 (2013.01); C12Q 1/6806 (2013.01); C12Q 1/6809 (2013.01);
(Continued)

(58) Field of Classification Search
None
See application file for complete search history.

(56) References Cited

U.S. PATENT DOCUMENTS 6,849,404 B2    2/2005  Park et al.
7,601,499 B2    10/2009  Berka et al.
(Continued)

FOREIGN PATENT DOCUMENTS

EP    1256630 A2    11/2002
EP    1256630 A3    2/2004
(Continued)

OTHER PUBLICATIONS

Zheng et al., "Titration-free 454 sequencing using Y adapters," Nat. Protoc. 2011, 6:1367-1376. (Year: 2011).\*
(Continued)

*Primary Examiner* — Kaijiang Zhang
(74) *Attorney, Agent, or Firm* — Illumina, Inc.

(57) ABSTRACT

The present invention is concerned with compositions and methods for improving the rate of correct sample identification in indexed nucleic acid library preparations for multiplex next generation sequencing by blocking the 3' ends of pooled indexed polynucleotides from multiple samples prior to amplification and sequencing, by exonuclease treatment and optionally blocking the 3' ends of pooled indexed polynucleotides from multiple samples prior to amplification and sequencing, by exonuclease treatment after protective adapters are ligated to target polynucleotides to degrade unincorporated adapters prior to amplification and sequencing, and/or by modifying or blocking 5' and 3' ends of pooled
(Continued)

indexed polynucleotides from multiple samples, with an optional exonuclease treatment, prior to amplification and sequencing.

17 Claims, 27 Drawing Sheets

Related U.S. Application Data a continuation-in-part of application No. 15/959,897, filed on Apr. 23, 2018, now Pat. No. 10,995,369, and a continuation-in-part of application No. 15/959,712, filed on Apr. 23, 2018, now Pat. No. 10,975,430, and a continuation-in-part of application No. 15/960,035, filed on Apr. 23, 2018, now Pat. No. 11,459,610, said application No. 17/181,271 is a division of application No. 15/959,984, filed on Apr. 23, 2018, now Pat. No. 10,934,584.

(60) Provisional application No. 62/488,830, filed on Apr. 23, 2017, provisional application No. 62/488,824, filed on Apr. 23, 2017, provisional application No. 62/488,825, filed on Apr. 23, 2017, provisional application No. 62/488,833, filed on Apr. 23, 2017.

(51) Int. Cl.

| | |
|---|---|
| C12Q 1/6809 | (2018.01) |
| C12Q 1/6816 | (2018.01) |
| C12Q 1/6834 | (2018.01) |
| C12Q 1/6855 | (2018.01) |
| C40B 20/04 | (2006.01) |
| C40B 50/16 | (2006.01) |
| C40B 50/18 | (2006.01) |
| C40B 70/00 | (2006.01) |
| C40B 80/00 | (2006.01) |

(52) U.S. Cl.
CPC ......... *C12Q 1/6816* (2013.01); *C12Q 1/6834* (2013.01); *C12Q 1/6855* (2013.01); *C40B 20/04* (2013.01); *C40B 50/16* (2013.01); *C40B 50/18* (2013.01); *C40B 70/00* (2013.01); *C40B 80/00* (2013.01)

(56) References Cited

U.S. PATENT DOCUMENTS

| | | | |
|---|---|---|---|
| 7,741,463 | B2 | 6/2010 | Gormley et al. |
| 8,053,192 | B2 | 11/2011 | Bignell et al. |
| 8,182,989 | B2 | 5/2012 | Bignell et al. |
| 8,822,150 | B2 | 9/2014 | Bignell et al. |
| 8,895,249 | B2 | 11/2014 | Shen et al. |
| 9,169,513 | B2 | 10/2015 | Shen et al. |
| 9,376,678 | B2 | 6/2016 | Gormley et al. |
| 9,512,478 | B2 | 12/2016 | Bignell et al. |
| 9,650,628 | B2 | 5/2017 | Amorese et al. |
| 9,758,816 | B2 | 9/2017 | Shen et al. |
| 9,850,484 | B2 | 12/2017 | Joung et al. |
| 9,968,901 | B2 | 5/2018 | Head et al. |
| 10,036,013 | B2 | 7/2018 | Kim |
| 10,167,500 | B2 | 1/2019 | Becker et al. |
| 10,174,352 | B2 | 1/2019 | Arnold et al. |
| 10,221,452 | B2 | 3/2019 | Rigatti et al. |
| 10,253,359 | B2 | 4/2019 | Gormley et al. |
| 10,995,369 | B2 | 5/2021 | Vermaas et al. |
| 11,359,233 | B2 | 6/2022 | Woodhouse et al. |
| 2002/0192769 | A1 | 12/2002 | Park et al. |
| 2004/0209299 | A1 | 10/2004 | Pinter et al. |
| 2006/0292611 | A1 | 12/2006 | Berka et al. |
| 2009/0233291 | A1 | 9/2009 | Chen et al. |
| 2010/0062494 | A1 | 3/2010 | Church et al. |
| 2010/0311064 | A1 | 12/2010 | Oliphant et al. |
| 2013/0231253 | A1 | 9/2013 | Amorese et al. |
| 2014/0066335 | A1 | 3/2014 | Gormley et al. |
| 2015/0051116 | A1 | 2/2015 | Kim |
| 2015/0265995 | A1 | 9/2015 | Head et al. |
| 2016/0017392 | A1 | 1/2016 | Arnold et al. |
| 2016/0090623 | A1 | 3/2016 | Rigatti et al. |
| 2016/0186249 | A1 | 6/2016 | Becker et al. |
| 2016/0355880 | A1 | 12/2016 | Gormley et al. |
| 2017/0088833 | A1 | 3/2017 | Joung et al. |
| 2018/0044668 | A1 | 2/2018 | Jiang et al. |
| 2018/0305750 | A1 | 10/2018 | Smith et al. |
| 2018/0305751 | A1 | 10/2018 | Vermaas et al. |
| 2018/0305752 | A1 | 10/2018 | Vermaas et al. |
| 2018/0305753 | A1 | 10/2018 | Chesney et al. |

FOREIGN PATENT DOCUMENTS

| | | | |
|---|---|---|---|
| GB | 20160015486 | | 10/2016 |
| WO | 2007052006 | A1 | 5/2007 |
| WO | 2009098037 | A1 | 8/2009 |
| WO | 2011112534 | A1 | 9/2011 |
| WO | 2013177220 | A1 | 11/2013 |
| WO | 2015069374 | A1 | 5/2015 |
| WO | WO 2016/058517 | A1 | 4/2016 |
| WO | 2016130704 | A2 | 8/2016 |
| WO | 2018144216 | A1 | 8/2018 |
| WO | 2018197945 | A1 | 11/2018 |
| WO | 2018197950 | A1 | 11/2018 |
| WO | 2018200380 | A1 | 11/2018 |
| WO | 2018200386 | A1 | 11/2018 |

OTHER PUBLICATIONS

Zheng et al., "Titration-free 454 sequencing using Y adapters," Nature Protocols, 2011, vol. 6, No. 9, pp. 1367-1376.

Nikiforov et al., "The Use of Phosphorothioate Primers and Exonuclease Hydrolosis for the Preparation of Single-stranded PCR Products and their Detection by Solid-phase Hybridization," Jan. 30, 2012, *Genome Research*, 3:285-94.

Ambardar et al., "High Throughput Sequencing: An Overview of Sequencing Chemistry," Indian Journal of Microbiology, Oct.-Dec. 2016, vol. 56, No. 4, pp. 394-404.

Esling et al., "Accurate multiplexing and filtering for high-throughput amplicon-sequencing," Nucleic Acids Research, 2015, vol. 43, No. 5, pp. 2513-2524.

Sinha et al., "Index switching causes "spreading-of-signal" among multiplexed samples in Illumina HiSeq 4000 DNA sequencing," bioRxiv, Apr. 9, 2017, 29 pages.

Kircher et al., "Double indexing overcomes inaccuracies in multiplex sequencing on the Illumina platform," Nucleic Acids Research, 2012, vol. 40, No. 1, pp. 1-8.

Illumina, "Effects of Index Misassignment on Multiplexing and Downstream Analysis," Illumina, Inc., 2017, 4 pages.

International Preliminary Report on Patentability for PCT/IB2018/000497, issued Oct. 29, 2019, 7 pages.

International Preliminary Report on Patentability for PCT/IB2018/000509, issued Oct. 29, 2019, 6 pages.

International Preliminary Report on Patentability for PCT/US2018/028867, issued Oct. 29, 2019, 8 pages.

International Preliminary Report on Patentability for PCT/US2018/028881, issued Oct. 29, 2019, 7 pages.

International Search Report and Written Opinion for PCT/IB2018/000497, issued Jun. 29, 2018, 14 pages.

International Search Report and Written Opinion for PCT/US2018/028881, issued Jun. 28, 2018, 14 pages.

International Search Report and Written Opinion PCT/IB2018/000509, issued Sep. 12, 2018, 14 pages.

International Search Report and Written Opinion PCT/US2018/028867, issued Jun. 28, 2018, 15 pages.

(56)     References Cited

OTHER PUBLICATIONS

Kircher et al., "Double indexing overcomes inaccuracies in multi-plex sequencing on the Illumina platform—Supplementary Tables," Nucleic Acids Research, 2012, vol. 40, No. 1, pp. 1-17.

* cited by examiner

12 different P7 Indices; 8 different P5 Indices

|   | 1 | 2 | 3 | 4 | 5 | 6 | 7 | 8 | 9 | 10 | 11 | 12 |
|---|---|---|---|---|---|---|---|---|---|----|----|----|
| A | D701-D601 | D702-D601 | D703-D601 | D704-D601 | D705-D601 | D706-D601 | D707-D601 | D708-D601 | D709-D601 | D710-D601 | D711-D601 | D712-D601 |
| B | D701-D602 | D702-D602 | D703-D602 | D704-D602 | D705-D602 | D706-D602 | D707-D602 | D708-D602 | D709-D602 | D710-D602 | D711-D602 | D712-D602 |
| C | D701-D603 | D702-D603 | D703-D603 | D704-D603 | D705-D603 | D706-D603 | D707-D603 | D708-D603 | D709-D603 | D710-D603 | D711-D603 | D712-D603 |
| D | D701-D604 | D702-D604 | D703-D604 | D704-D604 | D705-D604 | D706-D604 | D707-D604 | D708-D604 | D709-D604 | D710-D604 | D711-D604 | D712-D604 |
| E | D701-D605 | D702-D605 | D703-D605 | D704-D605 | D705-D605 | D706-D605 | D707-D605 | D708-D605 | D709-D605 | D710-D605 | D711-D605 | D712-D605 |
| F | D701-D606 | D702-D606 | D703-D606 | D704-D606 | D705-D606 | D706-D606 | D707-D606 | D708-D606 | D709-D606 | D710-D606 | D711-D606 | D712-D606 |
| G | D701-D607 | D702-D607 | D703-D607 | D704-D607 | D705-D607 | D706-D607 | D707-D607 | D708-D607 | D709-D607 | D710-D607 | D711-D607 | D712-D607 |
| H | D701-D608 | D702-D608 | D703-D608 | D704-D608 | D705-D608 | D706-D608 | D707-D608 | D708-D608 | D709-D608 | D710-D608 | D711-D608 | D712-D608 |

COMPOSITIONS AND METHODS FOR IMPROVING SAMPLE IDENTIFICATION IN INDEXED NUCLEIC ACID LIBRARIES

RELATED APPLICATIONS

This application is a continuation-in-part of U.S. patent application Ser. No. 15/959,712, filed Apr. 23, 2018, which claims the benefit of U.S. Provisional Application Ser. No. 62/488,824, filed on Apr. 23, 2017; a continuation-in-part of U.S. patent application Ser. No. 15/960,035, filed Apr. 23, 2018, which claims the benefit of U.S. Provisional Application Ser. No. 62/488,825, filed Apr. 23, 2017; a continuation-in-part of U.S. patent application Ser. No. 15/959,897, filed Apr. 23, 2018, which claims the benefit of U.S. Provisional Application Ser. No. 62/488,830, filed on Apr. 23, 2017; and a continuation-in-part of U.S. patent application Ser. No. 17/181,271, filed Feb. 22, 2021, which is a divisional of U.S. patent application Ser. No. 15/959,984, filed Apr. 23, 2018, now U.S. Pat. No. 10,934,584, issued Mar. 2, 2021, which claims the benefit of U.S. Provisional Application Serial No. 62/488,833, filed on Apr. 23, 2017, each of which is incorporated herein by reference in its entirety.

FIELD

The present disclosure relates to, among other things, sequencing of polynucleotides from multiple indexed libraries; and more particularly to increasing the likelihood that sequencing properly identifies the library from which the polynucleotides originated.

BACKGROUND

Improvements in sequencing methodologies have allowed for sequencing of pooled or multiplexed polynucleotides from different libraries in a single sequencing protocol. A library-specific sequence (an "index tag" or "sample-specific tag") may be added to polynucleic acids of each library so that the origin of each sequenced polynucleic acid may be properly identified. The index tag sequence may be added to polynucleotides of a library by, for example, ligating adapters comprising the index tag sequence to ends of the polynucleic acids.

The adapters may contain sequences in addition to the index tag sequence, such as a universal extension primer sequence and a universal sequencing primer sequence. The universal extension primer sequence, also referred to as a universal primer extension sequence, may, among other things, hybridize to a first oligonucleotide coupled to a solid surface. The first oligonucleotide may have a free 3' end from which a polymerase may add nucleotides to extend the sequence using the hybridized library polynucleotide as a template, resulting in a reverse strand of the library polynucleotide being coupled to the solid surface. Additional copies of forward and reverse strands may be coupled to the solid surface through cluster amplification. One example of cluster amplification is bridge amplification in which the 3' end of previously amplified polynucleotides that are bound to the solid surface hybridize to second oligonucleotides bound to the solid surface. The second oligonucleotide may have a free 3' end from which a polymerase may add nucleotides to extend the sequence using the coupled reverse strand polynucleotide as a template, resulting in a forward strand of the library polynucleotide being coupled to the solid surface via the second oligonucleotide. The process may be repeated to produce clusters of forward and reverse strands coupled to the solid surface. The forward strands or the reverse strands may be removed, e.g. via cleavage, prior to sequencing.

A sequencing primer may hybridize to a portion of a polynucleotide strand coupled to the solid support. For example, the sequencing primer may hybridize to a universal sequencing primer sequence, also referred to as a universal primer binding site, if present. Sequencing may occur through multiple rounds of addition of nucleotides to the sequencing primer using the coupled polynucleotide as a template, and detecting the identity of the added nucleotides. Hybridization of the sequencing primer may occur at a location on the coupled polynucleotide strand to allow sequence identification of the index tag sequence as well as a target sequence of the polynucleotide coupled to the solid surface or separate sequencing primers may be employed to separately sequence the index tag sequence and the target sequence. Accordingly, the target sequence may be indexed to a particular library of origin based on the index tag sequence associated with the target sequence.

Despite the inclusion of a library-specific index tag sequence to each polynucleic acid to be sequenced, errors in identifying the library origin of a sequenced polynucleic acid may occur due to a phenomenon known as index hopping. Index hopping occurs when index tag sequences from one library are inadvertently added to a polynucleic acid from a different library. Index hopping may occur during library preparation or cluster amplification of the polynucleotides on a flow cell or other suitable solid support for sequencing. Index hopping may confound results of sequencing, such as resulting in improper assignment of library origin of a sequenced polynucleotide or discarding sequencing results.

BRIEF SUMMARY

Index hopping or jumping is observed when sequenced DNA library molecules contain a different index sequence than was present in the library adaptor during library preparation. Index hopping can occur during sample preparation or during cluster amplification of pooled multiplexed libraries. One mechanism that causes index hopping involves the presence of free unligated adaptor molecules present after library preparation.

Without intending to be limited by theory, the problem of index jumping has multiple modes, some of which involve the presence of residual unligated adaptor molecules and/or incomplete products left over from library preparation. One class of index jumping can be caused by free unligated adaptor molecules having a specific universal primer extension sequence, e.g., P7', present in the library pool, that can contribute to the formation of libraries with swapped indices. This problem can be prevented by use of a 5' exonuclease that specifically targets the P7' adaptor strand for degradation. This can be achieved, for instance, through the use of an exonuclease that is biased toward digestion of double-stranded 5' ends, or through the use of 5' end modifications to bias towards exonuclease-mediated degradation of the adaptor DNA molecules.

One or more aspects of the present disclosure address at least one potential mechanism associated with index hopping by blocking 3' ends of polynucleic acids, including unincorporated adapters, during library sample preparation. One or more aspects of the present disclosure address at least one potential mechanism associated with index hopping by degrading polynucleotides, including target polynucleotides and unincorporated adapters, which do not form adaptertarget-adapter polynucleotide sequences during library sample preparation. Without intending to be bound by theory, it is believed that index hopping may occur when an unincorporated adapter comprising an index tag sequence for one library hybridizes to a portion of an adapter from another library, and the unincorporated adapter serves as a primer during cluster amplification. Thus, a target sequence from one library may be tagged with an index tag of an adapter from another library. During subsequent rounds of cluster amplification, additional copies of the miss-tagged target may be amplified prior to sequencing. Such index hopping may confound results of subsequent sequencing. In one aspect, by blocking the 3' ends of polynucleotides in a library, including unincorporated adapters, during library sample preparation, the ability of the unincorporated adapters to serve as primers during cluster amplification will be blocked. In one aspect, by degrading unincorporated adapters during library sample preparation, unincorporated adapters from other libraries will not be available to serve as primers during cluster amplification and, thus, index hopping may be mitigated.

As used herein, a "blocked" 3' end of a polynucleotide or oligonucleotide is a 3' end of the polynucleotide or oligonucleotide that is modified to prevent incorporation of nucleotides on the 3' end to extend the polynucleotide or the oligonucleotide. For example, the 3' nucleotide may comprise a 3' dideoxynucleotide.

In some aspects described herein, a method includes providing a composition comprising first and second library. The first library includes a first plurality of polynucleotides comprising target polynucleotides to which first and second oligonucleotide adapters are bound in a first adapter-target-second adapter sequence of nucleotides. One or both of the first and second adapter sequences comprise a library-specific sequence. The second library includes a second plurality of polynucleotides comprising target polynucleotides to which first and second oligonucleotide adapters are attached in a first adapter-target-second adapter sequence of nucleotides. One or both of the first and second adapter sequences comprise a library-specific sequence.

The library-specific sequence of the first plurality of polynucleotides is different than the library-specific sequence of the second plurality of polynucleotides. The composition further comprises first and second oligonucleotide adapters that are not attached to target polynucleotides. The method further comprises blocking 3' ends of the first and second pluralities of polynucleotides and 3' ends of the first and second oligonucleotide adapters that are not attached to target polynucleotides. For example, the 3' ends of the first and second pluralities of polynucleotides and the first and second oligonucleotide adapters that are not attached to target polynucleotides may be blocked by incorporating a dideoxynucleotide onto the 3' ends of the oligonucleotides and polynucleotides. The terms "adaptor" and "adapter" are used interchangeably.

In some aspects described herein, a method includes providing a substrate having a surface comprising a plurality of attached oligonucleotides having a free 3' end and providing a composition comprising a first library including a first plurality of polynucleotides, a second library including a second plurality of polynucleotides, and first and second oligonucleotide adapters that are not attached to target polynucleotides. The first and second pluralities of polynucleotides comprise first adapter-target-second adapter sequences of nucleotides. One or both of the first and second adapter sequences comprise a library-specific sequence. The library-specific sequence of the first plurality of polynucleotides is different than the library-specific sequence of the second plurality of polynucleotides. The first adapter sequence of the first and second pluralities of polynucleotides comprises a sequence complementary to at least a portion of a sequence of the oligonucleotides attached to the surface of the substrate. 3' ends of the first and second pluralities of polynucleotides and 3' ends of the first and second oligonucleotide adapters that are not attached to target polynucleotides are blocked. The method further comprises contacting the surface of the substrate with the composition under conditions that permit hybridization of complementary portions of (i) the oligonucleotides attached to the surface of the substrate, and (ii) the first adapter sequence of the first and second pluralities of polynucleotides. The method further includes extending the oligonucleotides attached to the surface of the substrate from the free 3' end by incorporating nucleotides complementary to a sequence of the polynucleotides hybridized to the oligonucleotides attached to the surface of the substrate to produce a copy of at least a portion of the hybridized polynucleotide such that the copy is attached to the surface of the substrate.

In some aspects described herein, a method includes providing a first library of target polynucleotides from a first source. The target polynucleotides have 5' and 3' ends. The method further includes providing a second library of target polynucleotides from a second source. The target polynucleotides have 5' and 3' ends. The method includes attaching a first oligonucleotide adapter to the 5' ends of target polynucleotides of the first library, and attaching a second oligonucleotide adapter to the 3' ends of the target polynucleotides of the first library, to produce first library polynucleotides comprising first adapter-target-second adapter sequences of nucleotides. One or both of the first and second adapter sequences comprise a library-specific sequence. The method further includes attaching a first oligonucleotide adapter to the 5' ends of target polynucleotides of the second library, and attaching a second oligonucleotide adapter to the 3' ends of the target polynucleotides of the second library, to produce second library polynucleotides comprising first adapter-target-second adapter sequences of nucleotides. One or both of the first and second adapter sequences comprise a library-specific sequence. The library-specific sequence of the first library is different from the library-specific sequence of the second library. The method further includes blocking 3' ends of the first and second library polynucleotides. Blocking the 3' ends of the first and second library polynucleotides may comprise, for example, enzymatically incorporating a dideoxynucleotide onto the 3' ends of the first and second library polynucleotides.

In some aspects described herein, a composition comprises a first library including a first plurality of polynucleotides. The first plurality of polynucleotides comprises first adapter-target-second adapter sequences of nucleotides. One or both of the first and second adapter sequences comprise a library-specific sequence. The 3' ends of the polynucleotides of the first plurality of polynucleotides are blocked.

The composition may further comprise a second library including a second plurality of polynucleotides. The second plurality of polynucleotides comprises first adapter-target-second adapter sequences of nucleotides. One or both of the first and second adapter sequences comprise a library-specific sequence. The library-specific sequence of the first plurality of polynucleotides is different than the library-specific sequence of the second plurality of polynucleotides. The 3' ends of the polynucleotides of the second plurality of polynucleotides are blocked.

The composition may further include first and second adapters that are not attached to the target polynucleotides of the first or second plurality of polynucleotides. The 3' ends of the first and second adapters are blocked.

In some embodiments described herein, a composition includes a first library including a first plurality of polynucleotides. The first plurality of polynucleotides comprises first adapter-target-second adapter sequences of nucleotides. One or both of the first and second adapter sequences comprise a library-specific sequence. The composition further comprises an enzyme and reagents for blocking 3' ends of polynucleotides.

The composition may further comprise a second library including a second plurality of polynucleotides. The second plurality of polynucleotides comprises first adapter-target-second adapter sequences of nucleotides. One or both of the first and second adapter sequences comprise a library-specific sequence. The library-specific sequence of the first plurality of polynucleotides is different than the library-specific sequence of the second plurality of polynucleotides.

The composition may further include first and second adapters that are not attached to the target polynucleotides of the first or second plurality of polynucleotides.

In some aspects described herein, a method includes providing a first plurality of double-stranded target polynucleotide fragments. Each of the double-stranded target polynucleotide fragments has a first end and a second end. The method further includes providing a first adapter oligonucleotide comprising a first strand having a 5' end and a 3' end and a second strand having a 5' end and a 3' end. The first adapter oligonucleotide comprises (i) a double stranded region comprising the 5' end of the first strand and the 3' end of the second strand, and (ii) a single stranded region in which the first and second strands are single stranded. The single stranded region comprises the 3' end of the first strand and the 5' end of the second strand. The first adapter oligonucleotide comprises a first library-specific sequence. The 3' end of the first strand is modified to prevent digestion by an enzyme having 3' exonuclease activity, and the 5' end of the second strand is modified to prevent digestion by an enzyme having 5' exonuclease activity. The method further comprises incubating the first adapter oligonucleotide and the first plurality of double stranded target polynucleotide fragments under conditions suitable to ligate the 5' end of the first strand of the first adapter and the 3' end of the second strand of the first adapter to the first and second ends of the double stranded target polynucleotide fragments to produce a first library of polynucleotides comprising first adapter-target-first adapter sequences. The method further comprises contacting the first library of polynucleotides with an exonuclease, which is to be understood as being one or more exonuclease. The exonuclease comprises 3' and 5' single stranded exonuclease activity, to selectively degrade first adapter oligonucleotides that are not ligated to the double stranded target polynucleotide fragments.

In some aspects described herein, an oligonucleotide adapter for ligating to a target polynucleotide prior to sequencing includes a first oligonucleotide strand having a 5' end and a 3' end; and a second oligonucleotide strand having a 5' end and a 3' end. A region of the 5' end of the first strand comprises nucleotides complementary to nucleotides in a region of the 3' end of the second strand such that the complementary regions are double-stranded. A region of the 3' end of the first strand and a region of the 5' end of the second strand are sufficiently non-complementary to be single-stranded. At least one of the first strand and the second strand comprises a library-specific index tag sequence. The 3' end of the first strand is modified to prevent digestion by an enzyme having 3' exonuclease activity, and the 5' end of the second strand is modified to prevent digestion by an enzyme having 5' exonuclease activity.

In addition or alternatively, aspects of embodiments of the present disclosure relates to protecting from exonucleases the 5' and 3' ends of template polynucleotides for immobilizing on a surface for sequencing, and degrading residual unprotected polynucleotides to inhibit the ability of the unprotected polynucleotides from participating in index hopping.

In some aspects described herein, a method includes providing a first library comprising a first plurality of polynucleotides having a first adapter-target-first adapter sequence. The polynucleotides of the first plurality of polynucleotide are double stranded in a region comprising the target and at least a portion of the first adapter on both ends of the target. The method further includes providing a first primer oligonucleotide configured to hybridize with a portion of the first adapter in proximity to a 3' end of a strand of the first adapter. The 5' end of the first primer oligonucleotide is modified to prevent digestion by an enzyme having 5' exonuclease activity. The method further includes providing a second primer oligonucleotide configured to hybridize with a complement of a portion of the first adapter in proximity to a 3' end of a strand of the complement of the first adapter. The 5' end of the second primer oligonucleotide is modified to prevent digestion by an enzyme having 5' exonuclease activity. The method further includes incubating the first library with the first and second primer oligonucleotides in a solution under conditions suitable to amplify the polynucleotides having a first adapter-target-first adapter sequence to produce an amplified first library of polynucleotides having 5' ends modified to prevent digestion by an enzyme having 5' exonuclease activity. The amplified polynucleotides have an amplified first adapter-target-amplified first adapter sequence. The amplified first adapter sequence comprises a first library-specific sequence. The method further includes modifying 3' ends of the amplified first library polynucleotides to prevent one or both of (i) digestion by an enzyme having 3' exonuclease activity, or (ii) addition of nucleotides to the 3' end by an enzyme having polymerase activity, thereby generating a protected first library of polynucleotides having modified 5' and 3' ends. Preferably, the 3' ends are modified to inhibit the addition of nucleotides to the 3' end by an enzyme having polymerase activity.

The protected first library of polynucleotides having modified 5' and 3' ends may be pooled with similar polynucleotides from other libraries and immobilized for a surface for sequencing. When the 3' ends were modified to include dideoxynucleotides, a decrease in index hopping of nearly 100-fold was observed.

In some aspects described herein, a polynucleotide prepared for immobilizing for sequencing has an adapter-target-adapter sequence. The adapter sequence comprises a library specific sequence. The polynucleotide is double stranded in a region comprising the target and at least a portion of the adapter on both ends of the target. The 5' and 3' ends of the polynucleotide in a region of the adapter sequence are single stranded. The 5' ends are modified to prevent digestion by an enzyme having 5' exonuclease activity. The 3' ends are modified to inhibit one or both of (i) digestion by an enzyme having 3' exonuclease activity, or (ii) addition of nucleotides to the 3' end by an enzyme having polymerase activity. Preferably, the 3' ends are modified to inhibit the addition of nucleotides to the 3' end by an enzyme having polymerase activity.

In some aspects described herein, a kit comprises an adapter as described in the previous paragraph and an exonuclease. In some aspects described herein, a composition comprises an adapter as described in the previous paragraph and an exonuclease.

In some aspects described herein, a composition includes a plurality of polynucleotides comprising a first adapter-target-second adapter sequence. The target sequence is double stranded. A region of the first adapter in proximity to the target is double stranded. A region of the second adapter in proximity to the target is double stranded.

A region of the first adapter distal to the target comprises two single strands, each having an end. A region of the second adapter distal to the target comprises two single strands, each having an end. At least one strand of the two single strands of the first or second adapter comprises a library-specific index tag sequence. Each end of the two single strands of the first and second adapters are modified to prevent digestion by an exonuclease.

The composition of the previous paragraph may optionally comprise an adapter that includes a first oligonucleotide strand having a 5' end and a 3' end; and a second oligonucleotide strand having a 5' end and a 3' end. A region of the 5' end of the first strand comprises nucleotides complementary to nucleotides in a region of the 3' end of the second strand such that the complementary regions are double-stranded. A region of the 3' end of the first strand and a region of the 5' end of the second strand are sufficiently non-complementary to be single-stranded. At least one of the first strand and the second strand comprises a library-specific index tag sequence. The 3' end of the first strand is modified to prevent digestion by an enzyme having 3' exonuclease activity, and the 5' end of the second strand is modified to prevent digestion by an enzyme having 5' exonuclease activity.

The compositions of either of the previous two paragraphs may further comprise an exonuclease.

In some embodiments, compositions comprise the polynucleotide and an exonuclease.

In one embodiment, free unligated P7' adaptor molecules present after library preparation can anneal to the immobilized surface P7 primer on a substrate such as a flow cell and serve as a template for generation of a longer, modified immobilized surface primer that contains a specific index sequence, e.g., i7, and a common universal primer binding sequence. The modified surface primer would then have complementarity to library molecules in the adaptor region 3' of the index molecule, allowing the generation of surface-bound library molecule with a different i7 index sequence than was present in the original library molecule.

This mechanism of index jumping can be reduced or eliminated through the use of 5' exonucleases to selectively degrade unligated P7' adaptor molecules. One mode of selective degradation involves the use of a 5' exonuclease with 5' to 3' exonuclease activity that is biased toward degradation of double stranded DNA molecules. This approach could be used in the context of a library preparation method using forked adaptors, with one double stranded end (possibly containing a short 3' overhang), and a "forked" single stranded end. After ligation to sample insert libraries, the resultant library contains single-stranded "forked" regions on both ends. Some unligated adaptor molecules remain that include the double stranded end. The P7' strand of this adaptor molecule can then be targeted for degradation through the use of a 5' to 3' exonuclease that is biased toward digestion of double stranded DNA. Use of a 5' to 3' exonuclease that selectively targets a 5' phosphorylated double stranded end aids in narrowing the activity of the exonuclease to unligated adaptors.

Another mode of selective degradation involves the use of a 5' exonuclease with 5' to 3' exonuclease activity and 3' to 5' DNA exonuclease activity. This approach could also be used in the context of a library preparation method using forked adaptors, with one double stranded end (possibly containing a short 3' overhang), and a "forked" single stranded end. After ligation to sample insert libraries, some unligated adaptor molecules remain that include the double stranded end. The P7' strand of this adaptor molecule can then be targeted for degradation through the use of 5' exonuclease with 5' to 3' exonuclease activity and 3' to 5' DNA exonuclease activity, but the 3' to 5' DNA exonuclease activity can be reduced by the use of a modification at each of the 3' ends of an adapter to block the 3' to 5' exonuclease activity. This modification prevents digestion of adaptor-target-adaptor molecules from the free 3' ends. An optional modification is at the 5' "forked" single stranded end. This modification prevents digestion of adaptor-target-adaptor molecules from the free 5' ends.

One class of index jumping can be caused by incomplete products present in the library pool. During library production incomplete species can result, such as adaptor-target molecules which do not include the desired structure of a target molecule flanked on each end by adaptor molecules, and target molecules which do not have an adaptor molecule attached at either end. These species can contribute to the formation of libraries with swapped indices by acting as primers for unwanted extension reactions.

This mechanism of index jumping can be reduced or eliminated through the use of exonucleases having 3' to 5' exonuclease activity to selectively degrade incomplete products present in the library pool. This approach could also be used in the context of a library preparation method using forked adaptors, with one double stranded end (possibly containing a short 3' overhang), and a "forked" single stranded end. After ligation to sample insert libraries, some incomplete products remain that include either a double stranded end and a "forked" single stranded end, or two double stranded ends.

These double stranded ends can be targeted for degradation through the use of an exonuclease having 3' to 5' exonuclease activity that is biased towards double stranded DNA molecules. Use of a 3' to 5' exonuclease that selectively targets blunt or recessed 3' termini can aid in narrowing the activity of the exonuclease to the incomplete products.

One class of index jumping can be caused by free unligated adaptor molecules having a specific universal primer extension sequence, e.g., P7', present in the library pool, or incomplete products, such as adaptor-target molecules which do not include a target polynucleotide flanked by on each end by adaptor molecules, that can contribute to the formation of libraries with swapped indices by acting as primers for unwanted extension reactions. This problem can be prevented introducing 3' blocks into free unligated adaptor molecules having a specific universal primer extension sequence, e.g., P7', or incomplete products present in the library pool.

Provided herein are compositions and methods for mitigating index hopping and its effect on sequencing data quality.

The methods, polynucleotides, compositions, and kits described herein may be useful in mitigating index hopping, for example by blocking 3' ends of polynucleotides, including unincorporated adapters, or degrading unblocked polynucleotides, including unincorporated adapters, during library sample preparation. By blocking the 3' ends of the unincorporated adapters, the unincorporated adapters cannot be extended during cluster amplification if the adapters hybridize to an adapter-target-adapter polynucleotide sequence during cluster amplification. In addition or alternatively, those polynucleotides that are not blocked at the 3' end may be degraded by an exonuclease to mitigate index hopping. In addition, it will be understood that degrading incomplete products, such as target polynucleotides to which no adapter is ligated or to which only one adapter is ligated, would be generally beneficial for reducing binding of polynucleic acids to the solid support that may not serve as effective templates for sequencing.

Additional features and advantages of the subject matter of the present disclosure will be set forth in the detailed description which follows, and in part will be readily apparent to those skilled in the art from that description or recognized by practicing the subject matter of the present disclosure as described herein, including the detailed description which follows, the claims, as well as the appended drawings.

It is to be understood that both the foregoing general description and the following detailed description present embodiments of the subject matter of the present disclosure, and are intended to provide an overview or framework for understanding the nature and character of the subject matter of the present disclosure as it is claimed. The accompanying drawings are included to provide a further understanding of the subject matter of the present disclosure, and are incorporated into and constitute a part of this specification. The drawings illustrate various embodiments of the subject matter of the present disclosure and together with the description serve to explain the principles and operations of the subject matter of the present disclosure. Additionally, the drawings and descriptions are meant to be merely illustrative, and are not intended to limit the scope of the claims in any manner.

BRIEF DESCRIPTION OF THE DRAWINGS

The following detailed description of specific embodiments of the present disclosure may be best understood when read in conjunction with the following drawings.

FIG. 24A shows how reads from a given sample are incorrectly demultiplexed and mixed with a different sample following demultiplexing. FIG. 24B demonstrates index hopping in a dual index system, where it leads to unexpected combinations of index tag sequences.

FIG. 25A shows an exemplary layout of a dual adapter plate, wherein each individual well of a 96-well plate contains a unique pair of index tag sequences. FIG. 25B shows an experimental setup aimed at measuring the rate of index hopping, wherein only unique dual index tag combinations are used.

FIG. 26A shows a 6-fold increase in index hopping associated with a 50% spike-in of free adapters. FIG. 26B shows an approximately linear effect of the free forked adapter on the rate of index hopping within the range tested.

FIG. 27 shows the effect of 3' blocking treatment according to the present invention on the rates of index hopping in Illumina TruSeq® PCR-Free and Nano (PCR) library preparation work flows, with and without a free adapter spike-in.

FIG. 29 shows the effect of combined exonuclease and 3' blocking treatment according to the present invention on the rates of index hopping in Illumina TruSeq® PCR-Free library preparation work flow, with and without a free adapter spike-in.

FIG. 30 shows the effect of combined exonuclease and 3' blocking treatment with protected adapters according to the present invention on the rates of index hopping in Illumina TruSeq PCR-Free library preparation work flow, with and without a free adapter spike-in.

Figure 1:
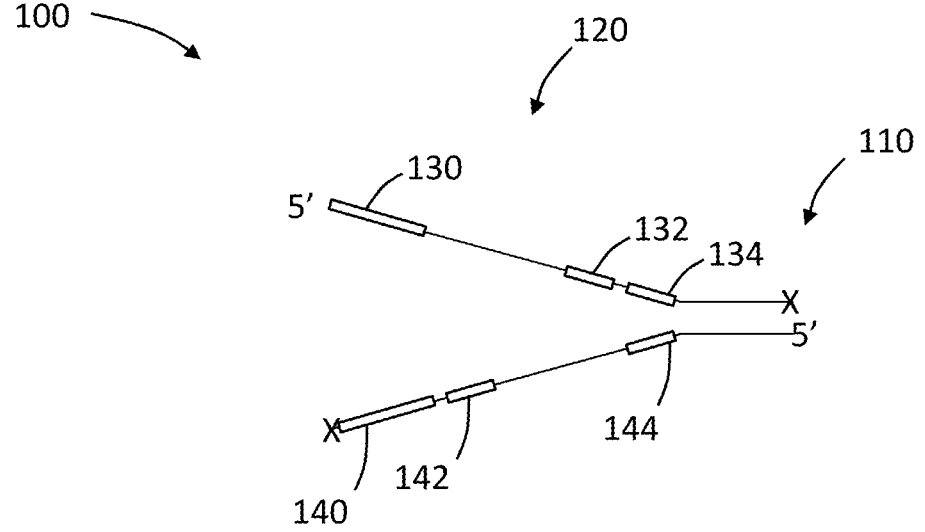
FIG. 1 is a schematic drawing of an embodiment of an adapter according to various aspects of the disclosure presented herein.

The schematic drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar to other numbered components.

DETAILED DESCRIPTION

Reference will now be made in greater detail to various embodiments of the subject matter of the present disclosure, some embodiments of which are illustrated in the accompanying drawings.

Definitions

All scientific and technical terms used herein have meanings commonly used in the art unless otherwise specified. The definitions provided herein are to facilitate understanding of certain terms used frequently herein and are not meant to limit the scope of the present disclosure.

As used herein, singular forms "a," "an" and "the" include plural referents unless the context clearly dictates otherwise. Thus, for example, reference to an "index tag sequence" includes examples having two or more such "index tag sequences" unless the context clearly indicates otherwise. In another example, reference to an "exonuclease" includes examples having two or more "exonucleases" unless the context clearly indicates otherwise.

As used in this specification and the appended claims, the term "or" is generally employed in its sense including "and/or" unless the content clearly dictates otherwise. The term "and/or" means one or all of the listed elements or a combination of any two or more of the listed elements. The use of "and/or" in some instances does not imply that the use of "or" in other instances may not mean "and/or."

As used herein, "have", "has", "having", "include", "includes", "including", "comprise", "comprises", "comprising" or the like are used in their open ended inclusive sense, and generally mean "include, but not limited to", "includes, but not limited to", or "including, but not limited to".

"Optional" or "optionally" means that the subsequently described event, circumstance, or component, can or cannot occur, and that the description includes instances where the event, circumstance, or component, occurs and instances where it does not.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the inventive technology.

Also herein, the recitations of numerical ranges by endpoints include all numbers subsumed within that range (e.g., 1 to 5 includes 1, 1.5, 2, 2.75, 3, 3.80, 4, 5, etc.). Where a range of values is "greater than", "less than", etc. a particular value, that value is included within the range.

Unless otherwise expressly stated, it is in no way intended that any method set forth herein be construed as requiring that its steps be performed in a specific order.

Accordingly, where a method claim does not actually recite an order to be followed by its steps or it is not otherwise specifically stated in the claims or descriptions that the steps are to be limited to a specific order, it is no way intended that any particular order be inferred. Any recited single or multiple feature or aspect in any one claim may be combined or permuted with any other recited feature or aspect in any other claim or claims.

While various features, elements or steps of particular embodiments may be disclosed using the transitional phrase "comprising," it is to be understood that alternative embodiments, including those that may be described using the transitional phrases "consisting" or "consisting essentially of," are implied. Thus, for example, implied alternative embodiments to a polynucleotide comprising an adapter-target-adapter sequence includes embodiments where the polynucleotide consists of the adapter-target-adapter sequence and embodiments where the polynucleotide consists essentially of the adapter-target-adapter sequence.

As used herein, "providing" in the context of a compound, polynucleotide, composition, or article means making the compound, polynucleotide, composition, or article, purchasing the compound, polynucleotide, composition, or article, or otherwise obtaining the compound, composition, or article.

As used herein, "amplify", "amplifying" or "amplification reaction" and their derivatives, refer generally to any action or process whereby at least a portion of a polynucleotide (e.g., template polynucleotide) is replicated or copied into at least one additional polynucleotide. The additional polynucleotide optionally includes a sequence that is substantially identical or substantially complementary to at least some portion of the template polynucleotide. The template polynucleotide may be single-stranded or double-stranded and the additional polynucleotide may independently be single-stranded or double-stranded. Amplification optionally includes linear or exponential replication of a polynucleotide. In some embodiments, such amplification may be performed using isothermal conditions; in other embodiments, such amplification may include thermocycling. In some embodiments, the amplification is a multiplex amplification that includes the simultaneous amplification of a plurality of target sequences in a single amplification reaction. In some embodiments, "amplification" includes amplification of at least some portion of DNA and RNA based nucleic acids alone, or in combination. The amplification reaction may include any of the amplification processes known to one of ordinary skill in the art. In some embodiments, the amplification reaction includes polymerase chain reaction (PCR).

As used herein, the term "polymerase" is intended to be consistent with its use in the art and includes, for example, an enzyme that produces a complementary replicate of a polynucleotide using the polynucleotide as a template strand. Typically, DNA polymerases bind to the template strand and then move down the template strand sequentially adding nucleotides to the free hydroxyl group at the 3' end of a growing strand of nucleic acid. DNA polymerases typically synthesize complementary DNA molecules from DNA templates and RNA polymerases typically synthesize RNA molecules from DNA templates (transcription). Polymerases may use a short RNA or DNA strand, called a primer, to begin strand growth. Some polymerases may displace the strand upstream of the site where they are adding bases to a chain. Such polymerases are said to be strand displacing, meaning they have an activity that removes a complementary strand from a template strand being read by the polymerase. Exemplary polymerases having strand displacing activity include, without limitation, the large fragment of Bst (*Bacillus stearothermophilus*) polymerase, exo-Klenow polymerase or sequencing grade T7 exo-polymerase. Some polymerases degrade the strand in front of them, effectively replacing it with the growing chain behind (5' exonuclease activity). Some polymerases have an activity that degrades the strand behind them (3' exonuclease activity). Some useful polymerases have been modified, either by mutation or otherwise, to reduce or eliminate 3' and/or 5' exonuclease activity.

As used herein, "conditions suitable for amplification," "amplification conditions" and its derivatives, generally refers to conditions suitable for amplifying one or more polynucleotide sequences. Such amplification may be linear or exponential. In some embodiments, the amplification conditions may include isothermal conditions or alternatively may include thermocycling conditions, or a combination of isothermal and thermocycling conditions. In some embodiments, the conditions suitable for amplifying one or more polynucleotide sequences include polymerase chain reaction (PCR) conditions. Typically, the amplification conditions refer to a reaction mixture that is sufficient to amplify polynucleotides such as one or more target sequences, or to amplify an amplified target sequence ligated to one or more adapters, e.g., an adapter-ligated amplified target sequence. Generally, the amplification conditions include a catalyst for amplification or for polynucleotide synthesis, for example a polymerase; a primer that possesses some degree of complementarity to the nucleic acid to be amplified; and nucleotides, such as deoxyribonucleotide triphosphates (dNTPs) to promote extension of the primer once hybridized to the nucleic acid. The amplification conditions may require hybridization or annealing of a primer to a nucleic acid, extension of the primer and a denaturing step in which the extended primer is separated from the polynucleotide sequence undergoing amplification. Typically, but not necessarily, amplification conditions may include thermocycling; in some embodiments, amplification conditions include a plurality of cycles where the steps of annealing, extending and separating are repeated. Typically, the amplification conditions include cations such as Mg++ or Mn++ and may also include various modifiers of ionic strength.

As used herein, the term "polymerase chain reaction" ("PCR") refers to the method of K. B. Mullis U.S. Pat. Nos. 4,683,195 and 4,683,202, which describe a method for increasing the concentration of a segment of a polynucleotide of interest in a mixture of genomic DNA without cloning or purification. This process for amplifying the polynucleotide of interest consists of introducing a large excess of two oligonucleotide primers to the DNA mixture containing the desired polynucleotide of interest, followed by a series of thermal cycling in the presence of a DNA polymerase. The two primers are complementary to their respective strands of the double stranded polynucleotide of interest. The mixture is denatured at a higher temperature first and the primers are then annealed to complementary sequences within the polynucleotide of interest molecule. Following annealing, the primers are extended with a polymerase to form a new pair of complementary strands. The steps of denaturation, primer annealing and polymerase extension may be repeated many times (referred to as thermocycling) to obtain a high concentration of an amplified segment of the desired polynucleotide of interest. The length of the amplified segment of the desired polynucleotide of interest (amplicon) is determined by the relative positions of the primers with respect to each other, and therefore, this length is a controllable parameter. By virtue of repeating the process, the method is referred to as the "polymerase chain reaction" (hereinafter "PCR"). Because the desired amplified segments of the polynucleotide of interest become the predominant nucleic acid sequences (in terms of concentration) in the mixture, they are said to be "PCR amplified". In a modification to the method discussed above, the polynucleotides may be PCR amplified using a plurality of different primer pairs, in some cases, one or more primer pairs per polynucleotide of interest, thereby forming a multiplex PCR reaction.

As defined herein "multiplex amplification" refers to selective and non-random amplification of two or more target sequences within a sample using at least one target-specific primer. In some embodiments, multiplex amplification is performed such that some or all of the target sequences are amplified within a single reaction vessel. The "plexy" or "plex" of a given multiplex amplification refers generally to the number of different target-specific sequences that are amplified during that single multiplex amplification. In some embodiments, the plexy may be about 12-plex, 24-plex, 48-plex, 96-plex, 192-plex, 384-plex, 768-plex, 1536-plex, 3072-plex, 6144-plex or higher. It is also possible to detect the amplified target sequences by several different methodologies (e.g., gel electrophoresis followed by densitometry, quantitation with a bioanalyzer or quantitative PCR, hybridization with a labeled probe; incorporation of biotinylated primers followed by avidin-enzyme conjugate detection; incorporation of 32P-labeled deoxynucleotide triphosphates into the amplified target sequence).

As used herein, the term "primer" and its derivatives refer generally to any polynucleotide that may hybridize to a target sequence of interest. Typically, the primer functions as a substrate onto which nucleotides may be polymerized by a polymerase; in some embodiments, however, the primer may become incorporated into the synthesized nucleic acid strand and provide a site to which another primer may hybridize to prime synthesis of a new strand that is complementary to the synthesized nucleic acid molecule. The primer may be comprised of any combination of nucleotides or analogs thereof. In some embodiments, the primer is a single-stranded oligonucleotide or polynucleotide.

The terms "polynucleotide" and "oligonucleotide" are used interchangeably herein to refer to a polymeric form of nucleotides of any length, and may comprise ribonucleotides, deoxyribonucleotides, analogs thereof, or mixtures thereof. This term refers only to the primary structure of the molecule. Thus, the term includes triple-, double- and single-stranded deoxyribonucleic acid ("DNA"), as well as triple-, double- and single-stranded ribonucleic acid ("RNA"). The terms polynucleotide and oligonucleotide used herein also encompasses cDNA, that is complementary or copy DNA produced from an RNA template, for example by the action of reverse transcriptase.

As used herein, "amplified target sequences" and its derivatives, refers generally to a polynucleotide sequence produced by the amplifying the target sequences using target-specific primers and the methods provided herein. The amplified target sequences may be either of the same sense (i.e the positive strand) or antisense (i.e., the negative strand) with respect to the target sequences.

As used herein, the terms "ligating", "ligation" and their derivatives refer generally to the process for covalently linking two or more molecules together, for example covalently linking two or more polynucleotides to each other. In some embodiments, ligation includes joining nicks between adjacent nucleotides of polynucleotides. In some embodiments, ligation includes forming a covalent bond between an end of a first and an end of a second polynucleotide. In some embodiments, the ligation may include forming a covalent bond between a 5' phosphate group of one nucleic acid and a 3' hydroxyl group of a second nucleic acid thereby forming a ligated polynucleotide. Generally for the purposes of this disclosure, an amplified target sequence may be ligated to an adapter to generate an adapter-ligated amplified target sequence.

As used herein, "ligase" and its derivatives, refers generally to any agent capable of catalyzing the ligation of two substrate molecules. In some embodiments, the ligase includes an enzyme capable of catalyzing the joining of nicks between adjacent nucleotides of a nucleic acid. In some embodiments, the ligase includes an enzyme capable of catalyzing the formation of a covalent bond between a 5' phosphate of one nucleic acid molecule to a 3' hydroxyl of another nucleic acid molecule thereby forming a ligated nucleic acid molecule. Suitable ligases may include, but not limited to, T4 DNA ligase, T4 RNA ligase, and E. coli DNA ligase.

As used herein, "ligation conditions" and its derivatives, generally refers to conditions suitable for ligating two molecules to each other. In some embodiments, the ligation conditions are suitable for sealing nicks or gaps between nucleic acids. As used herein, the term nick or gap is consistent with the use of the term in the art. Typically, a nick or gap may be ligated in the presence of an enzyme, such as ligase at an appropriate temperature and pH. In some embodiments, T4 DNA ligase may join a nick between nucleic acids at a temperature of about 70-72° C.

As used herein, the term "universal sequence" refers to a region of sequence that is common to two or more nucleic acid molecules where the molecules also have regions of sequence that differ from each other. A universal sequence that is present in different members of a collection of molecules may allow capture of multiple different nucleic acids using a population of universal capture nucleic acids that are complementary to the universal sequence. Similarly, a universal sequence present in different members of a collection of molecules may allow the replication or amplification of multiple different nucleic acids using a population of universal primers that are complementary to the universal sequence. Thus a universal capture polynucleotide or a universal primer includes a sequence that may hybridize specifically to a universal sequence. Polynucleotides may be modified to attach universal adapters, for example, at one or both ends of the different sequences.

As used herein, "re-amplification" and their derivatives refer generally to any process whereby at least a portion of an amplified nucleic acid molecule is further amplified via any suitable amplification process (referred to in some embodiments as a "secondary" amplification), thereby producing a reamplified nucleic acid molecule. The secondary amplification need not be identical to the original amplification process whereby the amplified nucleic acid molecule was produced; nor need the reamplified nucleic acid molecule be completely identical or completely complementary to the amplified nucleic acid molecule; all that is required is that the reamplified nucleic acid molecule include at least a portion of the amplified nucleic acid molecule or its complement. For example, the re-amplification can involve the use of different amplification conditions and/or different primers, including different target-specific primers than the primary amplification.

As used herein, the term "amplicon," when used in reference to a nucleic acid, means the product of copying the nucleic acid, wherein the product has a nucleotide sequence that is the same as or complementary to at least a portion of the nucleotide sequence of the nucleic acid. An amplicon can be produced by any of a variety of amplification methods that use the nucleic acid, or an amplicon thereof, as a template including, for example, polymerase extension, polymerase chain reaction (PCR), rolling circle amplification (RCA), ligation extension, or ligation chain reaction. An amplicon can be a nucleic acid molecule having a single copy of a particular nucleotide sequence (e.g. a PCR product) or multiple copies of the nucleotide sequence (e.g. a concatameric product of RCA). A first amplicon of a target nucleic acid is typically a complementary copy. Subsequent amplicons are copies that are created, after generation of the first amplicon, from the target nucleic acid or from the first amplicon. A subsequent amplicon can have a sequence that is substantially complementary to the target nucleic acid or substantially identical to the target nucleic acid.

As used herein, the term "amplification site" refers to a site in or on an array where one or more amplicons can be generated. An amplification site can be further configured to contain, hold or attach at least one amplicon that is generated at the site.

As used herein, the term "array" refers to a population of sites that can be differentiated from each other according to relative location. Different molecules that are at different sites of an array can be differentiated from each other according to the locations of the sites in the array. An individual site of an array can include one or more molecules of a particular type. For example, a site can include a single target nucleic acid molecule having a particular sequence or a site can include several nucleic acid molecules having the same sequence (and/or complementary sequence, thereof). The sites of an array can be different features located on the same substrate. Exemplary features include without limitation, wells in a substrate, beads (or other particles) in or on a substrate, projections from a substrate, ridges on a substrate, or channels in a substrate. The sites of an array can be separate substrates each bearing a different molecule. Different molecules attached to separate substrates can be identified according to the locations of the substrates on a surface to which the substrates are associated or according to the locations of the substrates in a liquid or gel. Exemplary arrays in which separate substrates are located on a surface include, without limitation, those having beads in wells.

As used herein, the term "capacity," when used in reference to a site and nucleic acid material, means the maximum amount of nucleic acid material that can occupy the site. For example, the term can refer to the total number of nucleic acid molecules that can occupy the site in a particular condition. Other measures can be used as well including, for example, the total mass of nucleic acid material or the total number of copies of a particular nucleotide sequence that can occupy the site in a particular condition. Typically, the capacity of a site for a target nucleic acid will be substantially equivalent to the capacity of the site for amplicons of the target nucleic acid.

As used herein, the term "capture agent" refers to a material, chemical, molecule or moiety thereof that is capable of attaching, retaining or binding to a target molecule (e.g. a target nucleic acid). Exemplary capture agents include, without limitation, a capture nucleic acid that is complementary to at least a portion of a target nucleic acid, a member of a receptor-ligand binding pair (e.g. avidin, streptavidin, biotin, lectin, carbohydrate, nucleic acid binding protein, epitope, antibody, etc.) capable of binding to a target nucleic acid (or linking moiety attached thereto), or a chemical reagent capable of forming a covalent bond with a target nucleic acid (or linking moiety attached thereto).

As used herein, the term "clonal population" refers to a population of nucleic acids that is homogeneous with respect to a particular nucleotide sequence. The homogenous sequence is typically at least 10 nucleotides long, but can be even longer including for example, at least 50, 100, 250, 500 or 1000 nucleotides long. A clonal population can be derived from a single target nucleic acid or template nucleic acid. Typically, all of the nucleic acids in a clonal population will have the same nucleotide sequence. It will be understood that a small number of mutations (e.g. due to amplification artifacts) can occur in a clonal population without departing from clonality.

Index Hopping

This disclosure relates to, among other things, sequencing of polynucleotides from multiple indexed libraries; and more particularly to increasing the likelihood that sequencing properly identifies the library from which the polynucleotides originated.

When polynucleotides from different libraries are pooled or multiplexed for sequencing, the polynucleotides from each library may be modified to include a library-specific index tag sequence, also referred to as a sample-specific tag. During sequencing the index tag is sequenced along with target polynucleotide sequences from the libraries. Accordingly, the index tag sequence may be associated with target polynucleotide sequence so that the library from which the target sequence originated may be identified.

However, a phenomenon referred to as index hopping may occur in a small percentage of sequence results (typically 0.5% to 2%). Index hopping refers to an index tag sequence from one library being associated with target polynucleotide from another library (see FIGS. 24A and 24B). While the mechanisms by which index hopping may occur are not fully understood, the rate of index hopping may be effectively reduced by blocking the 3' end of unincorporated adapters after the adapters are attached to the target polynucleotides of a library to, among other things, attach the index tag sequence to the polynucleotide.

Initial Library Sample Preparation

Libraries comprising polynucleotides may be prepared in any suitable manner to attach oligonucleotide adapters to target polynucleotides. As used herein, a "library" is a population of polynucleotides from a given source or sample. A library comprises a plurality of target polynucleotides. As used herein, a "target polynucleotide," "target fragment," "target nucleic acid fragment, "target molecule," "target nucleic acid molecule," and "target nucleic acid" are used interchangeably and refer to a polynucleotide that is desired to sequence. The target polynucleotide may be essentially any polynucleotide of known or unknown sequence. It may be, for example, a fragment of genomic DNA or cDNA. Sequencing may result in determination of the sequence of the whole, or a part of the target polynucleotides. The target polynucleotides may be derived from a primary polynucleotide sample that has been randomly fragmented. The target polynucleotides may be processed into templates suitable for amplification by the placement of universal primer sequences at the ends of each target fragment. The target polynucleotides may also be obtained from a primary RNA sample by reverse transcription into cDNA.

Primary polynucleotide molecules may originate in double-stranded DNA (dsDNA) form (e.g., genomic DNA fragments, PCR and amplification products and the like) or may have originated in single-stranded form, as DNA or RNA, and been converted to dsDNA form. By way of example, mRNA molecules may be copied into double-stranded cDNAs using standard techniques well known in the art. The precise sequence of primary polynucleotides is generally not material to the disclosure presented herein, and may be known or unknown.

In some embodiments, the primary target polynucleotides are RNA molecules. In an aspect of such embodiments, RNA isolated from specific samples is first converted to double-stranded DNA using techniques known in the art. The double-stranded DNA may then be index tagged with a library- or sample-specific tag. Different preparations of such double-stranded DNA comprising library specific index tags may be generated, in parallel, from RNA isolated from different sources or samples. Subsequently, different preparations of double-stranded DNA comprising different library specific index tags may be mixed, sequenced en masse, and the identity of each sequenced fragment determined with respect to the library from which it was isolated/derived by virtue of the presence of a library specific index tag sequence.

In some embodiments, the primary target polynucleotides are DNA molecules. For example, the primary polynucleotides may represent the entire genetic complement of an organism, and are genomic DNA molecules, such as human DNA molecules, which include both intron and exon sequences (coding sequence), as well as non-coding regulatory sequences such as promoter and enhancer sequences. Although it could be envisaged that particular sub-sets of polynucleotide sequences or genomic DNA could also be used, such as, for example, particular chromosomes or a portion thereof. In many embodiments, the sequence of the primary polynucleotides is not known. The DNA target polynucleotides may be treated chemically or enzymatically either prior to, or subsequent to a fragmentation processes, such as a random fragmentation process, and prior to, during, or subsequent to the ligation of the adaptor oligonucleotides.

Preferably, the primary target polynucleotides are fragmented to appropriate lengths suitable for sequencing. The target polynucleotides may be fragmented in any suitable manner. Preferably, the target polynucleotides are randomly fragmented. Random fragmentation refers to the fragmentation of a polynucleotide in a non-ordered fashion by, for example, enzymatic, chemical or mechanical means. Such fragmentation methods are known in the art and utilize standard methods (Sambrook and Russell, Molecular Cloning, A Laboratory Manual, third edition). For the sake of clarity, generating smaller fragments of a larger piece of polynucleotide via specific PCR amplification of such smaller fragments is not equivalent to fragmenting the larger piece of polynucleotide because the larger piece of polynucleotide remains in intact (i.e., is not fragmented by the PCR amplification). Moreover, random fragmentation is designed to produce fragments irrespective of the sequence identity or position of nucleotides comprising and/or surrounding the break.

In some embodiments, the random fragmentation is by mechanical means such as nebulization or sonication to produce fragments of about 50 base pairs in length to about 1500 base pairs in length, such as 50-700 base pairs in length or 50-500 base pairs in length.

Fragmentation of polynucleotide molecules by mechanical means (nebulization, sonication and Hydroshear for example) may result in fragments with a heterogeneous mix of blunt and 3'- and 5'-overhanging ends. Fragment ends may be repaired using methods or kits (such as the Lucigen DNA terminator End Repair Kit) known in the art to generate ends that are optimal for insertion, for example, into blunt sites of cloning vectors. In some embodiments, the fragment ends of the population of polynucleotides are blunt ended. The fragment ends may be blunt ended and phosphorylated. The phosphate moiety may be introduced via enzymatic treatment, for example, using polynucleotide kinase.

In some embodiments, the target polynucleotide sequences are prepared with single overhanging nucleotides by, for example, activity of certain types of DNA polymerase such as Taq polymerase or Klenow exo minus polymerase which has a non-template-dependent terminal transferase activity that adds a single deoxynucleotide, for example, deoxyadenosine (A) to the 3' ends of, for example, PCR products. Such enzymes may be utilized to add a single nucleotide 'A' to the blunt ended 3' terminus of each strand of the target polynucleotide duplexes. Thus, an 'A' could be added to the 3' terminus of each end repaired duplex strand of the target polynucleotide duplex by reaction with Taq or Klenow exo minus polymerase, while the adapter polynucleotide construct could be a T-construct with a compatible 'T' overhang present on the 3' terminus of each duplex region of the adapter construct. This end modification also prevents self-ligation of the target polynucleotides such that there is a bias towards formation of the combined ligated adapter-target polynucleotides.

In some embodiments, fragmentation is accomplished through tagmentation as described in, for example, International Patent Application Publication WO 2016/130704. In such methods transposases are employed to fragment a double stranded polynucleotide and attach a universal primer sequence into one strand of the double stranded polynucleotide. The resulting molecule may be gap-filled and subject to extension, for example by PCR amplification, using primers that comprise a 3' end that hybridizes to the attached universal primer sequence and a 5' end that contains other sequences of an adapter or using primers that comprise a 3' end that hybridizes to a complement of the attached universal primer sequence and a 5' end that contains other sequences of an adapter.

The adapters or portions of the adapters may be attached to the target polynucleotide in any other suitable manner. In some embodiments, the adapters are introduced in a multi-step process, such as a two-step process, involving ligation of a portion of the adapter to the target polynucleotide having a universal primer sequence. The second step comprises extension, for example by PCR amplification, using primers that comprise a 3' end that hybridizes to the attached universal primer sequence (or that hybridizes to a complement of the universal primer sequence) and a 5' end that contains other sequences of an adapter. By way of example, such extension may be performed as described in U.S. Pat. No. 8,053,192. Additional extensions may be performed to provide additional sequences to the 5' end of the resulting previously extended polynucleotide.

Fragmented polynucleotides that have been modified prior to ligation, for example to better prepare for ligation, may be referred to herein as polynucleotide "fragments."

Any suitable adapter may be ligated to a target polynucleotide. Preferably, the adapter comprises a first oligonucleotide strand having a 5' end and a 3' end; and a second oligonucleotide strand having a 5' end and a 3' end. A region of the 5' end of the first strand comprises nucleotides complementary to nucleotides in a region of the 3' end of the second strand such that the complementary regions are double-stranded. A region of the 3' end of the first strand and a region of the 5' end of the second strand are sufficiently non-complementary to be single-stranded.

In some embodiments, the entire adapter is ligated to the fragmented target polynucleotide. Preferably, the ligated adapter comprises a double stranded region that is ligated to a double stranded target polynucleotide. Preferably, the double-stranded region is as short as possible without loss of function. In this context, "function" refers to the ability of the double-stranded region to form a stable duplex under standard reaction conditions. In some embodiments, standard reactions conditions refer to reaction conditions for an enzyme-catalyzed polynucleotide ligation reaction, which will be well known to the skilled reader (e.g. incubation at a temperature in the range of 4° C. to 25° C. in a ligation buffer appropriate for the enzyme), such that the two strands forming the adapter remain partially annealed during ligation of the adapter to a target molecule. Ligation methods are known in the art and may utilize standard methods (Sambrook and Russell, Molecular Cloning, A Laboratory Manual, third edition). Such methods utilize ligase enzymes such as DNA ligase to effect or catalyze joining of the ends of the two polynucleotide strands of, in this case, the adapter duplex oligonucleotide and the target polynucleotide duplexes, such that covalent linkages are formed. The adapter duplex oligonucleotide may contain a 5'-phosphate moiety in order to facilitate ligation to a target polynucleotide 3'-OH. The target polynucleotide may contain a 5'-phosphate moiety, either residual from the shearing or fragmentation process, or added using an enzymatic treatment step, and has been end repaired, and optionally extended by an overhanging base or bases, to give a 3'-OH suitable for ligation. In this context, attaching means covalent linkage of polynucleotide strands which were not previously covalently linked. In a particular aspect of the invention, such attaching takes place by formation of a phosphodiester linkage between the two polynucleotide strands, but other means of covalent linkage (e.g. non-phosphodiester backbone linkages) may be used. Ligation of adapters to target polynucleotides is described in more detail in, for example, U.S. Pat. No. 8,053,192.

Any suitable adapter may be attached to a target polynucleotide via any suitable process, such as those discussed above. The adapter includes a library-specific index tag sequence. The index tag sequence may be attached to the target polynucleotides from each library before the sample is immobilized for sequencing. The index tag is not itself formed by part of the target polynucleotide, but becomes part of the template for amplification. The index tag may be a synthetic sequence of nucleotides which is added to the target as part of the template preparation step. Accordingly, a library-specific index tag is a nucleic acid sequence tag which is attached to each of the target molecules of a particular library, the presence of which is indicative of or is used to identify the library from which the target molecules were isolated.

The adapters may contain more than one index tag so that the multiplexing possibilities may be increased.

Whether the entire adapter or a portion of the adapter is attached to the double stranded target fragment, the adapter or portion comprises a double stranded region and a region comprising two non-complementary single strands. The double-stranded region of the adapter may be of any suitable number of base pairs. Preferably, the double stranded region is a short double-stranded region, typically comprising 5 or more consecutive base pairs, formed by annealing of two partially complementary polynucleotide strands. This "double-stranded region" of the adapter refers to a region in which the two strands are annealed and does not imply any particular structural conformation. In some embodiments, the double stranded region comprises 20 or less consecutive base pairs, such as 10 or less or 5 or less consecutive base pairs.

The stability of the double-stranded region may be increased, and hence its length potentially reduced, by the inclusion of non-natural nucleotides which exhibit stronger base-pairing than standard Watson-Crick base pairs. Preferably, the two strands of the adapter are 100% complementary in the double-stranded region.

When the adapter is attached to the target polynucleotide, the non-complementary single stranded region may form the 5' and 3' ends of the polynucleotide to be sequenced. The term "non-complementary single stranded region" refers to a region of the adapter where the sequences of the two polynucleotide strands forming the adapter exhibit a degree of non-complementarity such that the two strands are not capable of fully annealing to each other under standard annealing conditions for a PCR reaction.

The non-complementary single stranded region is provided by different portions of the same two polynucleotide strands which form the double-stranded region. The lower limit on the length of the single-stranded portion will typically be determined by function of, for example, providing a suitable sequence for i) binding of a primer for primer extension, PCR and/or sequencing (for instance, binding of a primer to a universal primer binding site), or for ii) binding of a universal capture nucleic acid for immobilization of a adapter-target-adapter to a surface (for instance, binding of a universal capture nucleic acid to a universal primer extension binding site).

Theoretically there is no upper limit on the length of the unmatched region, except that in general it is advantageous to minimize the overall length of the adapter, for example, in order to facilitate separation of unbound adapters from adapter-target constructs following the attachment step or steps. Therefore, it is generally preferred that the non-complementary single-stranded region of the adapter is 50 or less consecutive nucleotides in length, such as 40 or less, 30 or less, or 25 or less consecutive nucleotides in length.

In some embodiments, the single stranded ends of the adapter are modified to prevent digestion by an exonuclease. For example, the 3' end may be modified to prevent digestion by a 3' exonuclease, and the 5' end may be modified to prevent digestion by a 5' exonuclease. For purposes of the present disclosure, a modification that "prevents" digestion by an exonuclease inhibits the activity of the exonuclease relative to its action on an unmodified end. Preferably, a modification that prevents digestion exonuclease eliminates the ability of the exonuclease to digest the polynucleotide strand.

The free ends of the single stranded regions of the adapter may be modified in any suitable manner to prevent exonuclease activity. In some embodiments, the free ends of the single stranded regions of the adapter comprise a phosphorothioate bond. Preferably, bonds between the terminal three nucleotides of the free ends of the single stranded regions of the adapter comprise phosphorothioate bonds. For purpose of the present disclosure, an end of a polynucleotide whose bonds between the terminal three nucleotides comprise phosphorothioate bonds may be referred to as an end comprising three phosphorothioate bonds. Phosphorothioate bonds may be introduced into a 5' end or a 3' end of a polynucleotide in any suitable manner, as is well known in the art. Oligonucleotides comprising terminal phosphorothioate bonds may be purchased from a number of commercial vendors including, for example, Integrated DNA Technologies and Sigma-Aldrich.

In some embodiments, a single stranded DNA binding protein (SSB) is bound to the free ends of the single stranded regions of the adapter to protect the free ends of the adapter from exonuclease degradation. Any suitable SSB may be used to bind the single stranded regions of the adapter to protect the single stranded regions from exocuclease activity. Examples of suitable SSBs include herpes simplex virus (HSV-1) SSB (Mapelli M, Panjikar S, Tucker PA (2005). "The crystal structure of the herpes simplex virus 1 ssDNA-binding protein suggests the structural basis for flexible, cooperative single-stranded DNA binding". *J Biol Chem.* 280 (4): 2990-7); *E. coli* SSB (Meyer RR, Laine PS (December 1990). "The single-stranded DNA-binding protein of *Escherichia coli"*. *Microbiol. Rev.* 54 (4): 342-80); eukaryotic mitochondrial SSBs, such as human mitochondrial SSB (mtSSB) (Tiranti, V; Rocchi, M; DiDonato, S; Zeviani, M (30 Apr. 1993). "Cloning of human and rat cDNAs encoding the mitochondrial single-stranded DNA-binding protein (SSB)". *Gene.* 126 (2): 219-25) and *Saccharomyces cerevisiae* SSB (Van Dyck, E; Foury, F; Stillman, B; Brill, S J (September 1992). "A single-stranded DNA binding protein required for mitochondrial DNA replication in *S. cerevisiae* is homologous to *E. coli* SSB". *The EMBO Journal.* 11 (9): 3421-30); and eukaryotic replication protein A (Wold, M S (1997). "Replication protein A: heterotrimeric, single-stranded DNA-binding protein required for eukaryotic DNA metabolism". *Annual Review of Biochemistry.* 66 (1): 61-92). SSBs are commercially available from a number of vendors including ThermoFisher Scientific (Catalog number 70032Z500UG) and Sigma-Aldrich (MDL number MFCD00213047).

The SSBs may be bound to the single stranded free ends of the adapter prior, during, or after ligation of the adapter to the target polynucleotide. If the bound SSBs interfere with the ligation reaction, the SSBs are preferably bound to the single stranded free ends of the adapter after the adapters are ligated to the target polynucleotide. Following ligation of the adapter to the target polynucleotide, the following species of polynucleotides may remain: adapter, adapter-target, and adapter-target-adapter. The single stranded free ends of the adapters will be protected from exonuclease activity by the bound SSBs, while the double stranded region of the adapter and the adapter-target molecules will be susceptible to exonuclease activity. Following exonuclease degradation, adapter-target-adapter with bound SSBs will remain present. Prior to hybridizing the adapter-target-adapter polynucleotides to a solid surface having oligonucleotides complementary to at least one sequence of a free end an adapter, the SSBs may be removed to facilitate the hybridization. The SSBs may be removed in any suitable manner. For example, the SSBs may be removed under denaturing conditions.

In some embodiments, the free ends of the single stranded regions of the adapter include a biotin group to which avidin or streptavidin may bind to prevent degradation by an exonuclease. Biotin may be attached to free 5' and 3' ends of the adapter in any suitable manner. For example, biotin may be incorporated onto a 5' or 3' end of an adapter via enzymatic incorporation of a biotin-labeled nucleotide, via chemical modification of the 5' or 3' end to attach the biotin, through the use of labeled oligonucleotide primers, and the like. By way of example, biotin may be incorporated onto a 3' end using, for example, terminal deoxynucleotidyl transferase (TdT) to catalyze non-template-directed nucleotide incorporation of a biotinylated nucleotide onto the 3'-OH end of single-stranded DNA. One example of a kit for attaching biotin to a 3' end of a free end of an adapter is the ThermoScientific Pierce biotin 3' end labeling kit (catalog number 89818), which incorporated a 1-3 biotinylated ribonucleotide (biotin-11-UTP) onto the 3' end of single-stranded DNA using TdT.

The biotin-labeled nucleotide may comprise a cleavable linker, such as a disulfide bond, which may be cleaved with, for example, dithiothreitol to release the biotin (and any avidin or streptavidin). Biotin labels with cleavable linkers, including biotin-labelled nucleotides having cleavable linkers are commercially available from a number of vendors, such as Integrated DNA Technologies, Inc. (IDT) of Skokie, IL.

Avidin or streptavidin may be bound to the adapter prior, during, or after ligation of the adapter to the target polynucleotide. If the bound avidin or streptavidin interferes with the ligation reaction, the avidin or streptavidin are preferably bound to the single stranded free ends of the adapter after the adapters are ligated to the target polynucleotide. Following ligation of the adapter to the target polynucleotide, the following species of polynucleotides may remain: adapter, adapter-target, and adapter-target-adapter. The single stranded free ends of the adapters will be protected from exonuclease activity by the bound avidin or streptavidin, while the double stranded region of the adapter and the adapter-target molecules will be susceptible to exonuclease activity. Following exonuclease degradation, adapter-target-adapter with bound avidin or streptavidin will remain present. Prior to hybridizing the adapter-target-adapter polynucleotides to a solid surface having oligonucleotides complementary to at least one sequence of a free end an adapter, the avidin or streptavidin may be removed to facilitate the hybridization. The avidin or streptavidin may be removed in any suitable manner. Preferably, the biotin label comprises a cleavable linker which allows the biotin and the bound avidin or streptavidin to be removed.

In some embodiments, the free ends of the single stranded regions of the adapter are bound by antibodies directed to the Y-shaped adapters to prevent degradation from the 5' and 3' single stranded ends of the adapter by an exonuclease.

Preferably, the ends of the adapter that form the double stranded region of the adapter are susceptible to exonuclease activity. Preferably, the ends of the adapter that form the double stranded region of the adapter are at least as susceptible to exonuclease activity as ends containing unmodified nucleotides. In some embodiments, the ends of the adapter that form the double stranded region of the adapter contain unmodified nucleotides.

Individual strands of oligonucleotides may be mixed and annealed to produce an adapter having a double stranded portion and a single stranded portion for ligating the double stranded portion to a double stranded target fragment.

At least one of the first or second strands that form the adapter includes a library-specific index tag sequence. The index tag sequence may be attached to the target polynucleotides from each library by ligating the adapter to the target before the sample is immobilized for sequencing. The index tag is not itself formed by part of the target polynucleotide, but becomes part of the template for amplification. The index tag may be a synthetic sequence of nucleotides which is added to the target as part of the template preparation step. Accordingly, a library-specific index tag is a nucleic acid sequence tag which is attached to each of the target molecules of a particular library, the presence of which is indicative of or is used to identify the library from which the target molecules were isolated.

Preferably, the index tag sequence, also referred to as a sample-specific tag, is 20 nucleotides or less in length. For example, the index tag sequence may be 1-10 nucleotides or 4-6 nucleotides in length. A four nucleotide index tag gives a possibility of multiplexing 256 samples on the same array, a six base index tag enables 4096 samples to be processed on the same array.

The library-specific index tag sequence may be located in a single-stranded, double-stranded region, or span the single-stranded and double-stranded regions of the adapter. Preferably, the index tag sequence is in a single-stranded region of the adapter.

The adapters may include any other suitable sequence in addition to the index tag sequence. For example, the adapters may comprise universal extension primer sequences, which are typically located at the 5' or 3' end of the adapter and the resulting polynucleotide for sequencing. The universal extension primer sequences may hybridize to complementary primers bound to a surface of a solid substrate. The complementary primers comprise a free 3' end from which a polymerase or other suitable enzyme may add nucleotides to extend the sequence using the hybridized library polynucleotide as a template, resulting in a reverse strand of the library polynucleotide being coupled to the solid surface. Such extension may be part of a sequencing run or cluster amplification.

In some embodiments, the adapters comprise one or more universal sequencing primer sequences. The universal sequencing primer sequences may bind to sequencing primers to allow sequencing of an index tag sequence, a target sequence, or an index tag sequence and a target sequence.

The precise nucleotide sequence of the adapters is generally not material to the invention and may be selected by the user such that the desired sequence elements are ultimately included in the common sequences of the library of templates derived from the adapters to, for example, provide binding sites for particular sets of universal extension primers and/or sequencing primers and/or universal amplification primers and/or universal capture nucleic acids. Additional sequence elements may be included, for example, to provide binding sites for sequencing primers which will ultimately be used in sequencing of template molecules in the library, or products derived from amplification of the template library, for example on a solid support.

The adapter oligonucleotides may contain exonuclease resistant modifications such as phosphorothioate linkages. Such modifications reduce the number of adaptor-dimers present in the library, because the two adaptors cannot undergo ligation without removal of their non-complementary overhangs. In one embodiment, the adaptors can be treated with an exonuclease enzyme prior to the ligation reaction with the target, to ensure that the overhanging ends of the strands cannot be removed during the ligation process. Treatment of the adaptors in this manner reduces the formation of the adaptor-dimers at the ligation step.

Preferably, the adapter is attached to both ends of a target polypeptide to produce a polynucleotide having a first adapter-target-second adapter sequence of nucleotides. The first and second adapters may be the same or different. Preferably, the first and second adapters are the same. In such embodiments, the resulting polynucleotide would have a first adapter-target-first adapter sequence of nucleotides. If the first and second adapters are different, at least one of the first and second adapters comprises a library-specific index tag sequence.

It will be understood that a "first adapter-target-second adapter sequence," "first adapter-target-first adapter sequence," or an "adapter-target-adapter" sequence refers to the orientation of the adapters relative to one another and to the target and does not necessarily mean that the sequence may not include additional sequences, such as linker sequences, for example.

Other libraries may be prepared in a similar manner, each including at least one library-specific index tag sequence or combinations of index tag sequences different than an index tag sequence or combination of index tag sequences from the other libraries.

As used herein, "attached" or "bound" are used interchangeably in the context of an adapter relative to a target sequence. As described above, any suitable process may be used to attach an adapter to a target polynucleotide. For example, the adapter may be attached to the target through ligation with a ligase; through a combination of ligation of a portion of an adapter and addition of further or remaining portions of the adapter through extension, such as PCR, with primers containing the further or remaining portions of the adapters; through transposition to incorporate a portion of an adapter and addition of further or remaining portions of the adapter through extension, such as PCR, with primers containing the further or remaining portions of the adapters; or the like. Preferably, the attached adapter oligonucleotide is covalently bound to the target polynucleotide.

After the adapters or portions of the adapters are attached to the target polynucleotides, the resulting polynucleotides may be subjected to a clean-up process to enhance the purity to the adapter-target-adapter polynucleotides by removing at least a portion of the unincorporated adapters. Any suitable clean-up process may be used, such as electrophoresis, size exclusion chromatography, or the like. In some embodiments, gel purification and/or solid phase reverse immobilization (SPRI) paramagnetic beads may be employed to separate the adapter-target-adapter polynucleotides from the unattached adapters. While such processes may enhance the purity of the resulting adapter-target-adapter polynucleotides, some unattached adapter oligonucleotides likely remain.

Amplification

In some embodiments, the polynucleotide resulting from attaching the adapter or portion of the adapter to the double stranded target is then subjected to amplification with primers having 5' ends that are modified to prevent digestion by an enzyme having 5' exonuclease activity. The 5' ends of the primers may be modified in any suitable manner to prevent digestion by an enzyme having 5' exonuclease activity. In some embodiments, the 5' ends of the primers comprise a phosphorothioate bond. Preferably, bonds between the terminal three nucleotides of the 5' ends of the primers comprise phosphorothioate bonds.

If the adapter attached to the target prior to amplification is only a portion of the adapter, the remainder of the adapter may be provided by the 5' ends of the primers.

In either case, a first primer oligonucleotide for amplification that has a modified 5' end is configured to hybridize with a portion of the adapter or adapter portion in proximity to a 3' end of a strand of the adapter or portion. A second primer oligonucleotide for amplification that has a modified 5' end is configured to hybridize with a complement of a portion of the adapter or adapter portion in proximity to a 3' end of a strand of the complement of the adapter or portion. A complement of the adapter may result from extension of the first primer using the adapter-target-adapter as a template. Once the complement is formed, the second adapter may hybridize to the complement.

The first and second primers may be incubated with the polynucleotide resulting from attaching the adapter or portion of the adapter to the double stranded target (an "adapter-target-adapter" polynucleotide) under conditions suitable to amplify the adapter-target-adapter polynucleotides to produce polynucleotides having an amplified adapter-target-amplified adapter sequence with modified 5' ends. If the adapter-target-adapter polynucleotides comprise the entire adapter, the adapter-target-adapter polynucleotides may have the same sequence as the amplified adapter-target-amplified adapter sequence. If the adapter-target-adapter polynucleotides contain only a portion of the adapter, the amplified adapter-target-amplified adapter sequence will have additional nucleotides at the single stranded ends of the amplified adapter sequence due to the addition of the remainder of the adapter sequence from the primers.

Amplification of the adapter-target-adapter polynucleotides with the 5' modified primers results in a polynucleotide having amplified adapter-target-amplified adapter sequences with modified 5' ends.

The resulting amplified adapter includes a library-specific index tag sequence. Accordingly, the index tag is not itself formed by part of the target polynucleotide, but becomes part of the template for amplification on a solid surface for sequencing.

The amplified adapters may contain more than one index tag so that the multiplexing possibilities may be increased. The library-specific index tag sequence may be included on one or both of the 5' modified primers or may be included in a portion of the adapter that attached to the template fragment. If the library-specific index tag sequence is not included in the primers but is included in the potion of the adapter that is attached to the template fragment (and the primers add the remaining portion of the adapter), adapter-target-adapter polynucleotides from different libraries may be pooled to perform the amplification to the amplified adapter-target-amplified adapter polynucleotides. If the primers include the library-specific index tag sequence, then each library should be amplified separately prior to pooling.

In any case, the amplified adapters may include any other suitable sequence in addition to the index tag sequence. For example, the amplified adapters may comprise universal extension primer sequences, which are typically located at the 5' or 3' end of the amplified adapter and the resulting template polynucleotide for sequencing. In some embodiments, the amplified adapters comprise one or more universal sequencing primer sequences. The precise nucleotide sequence of the amplified adapters is generally not material to the invention and may be selected by the user such that the desired sequence elements are ultimately included in the common sequences of the library of templates derived from the amplified adaptors to, for example, provide binding sites for particular sets of universal extension primers and/or sequencing primers.

It will be understood that an "adapter-target-adapter sequence" or its equivalents refers to the orientation of the adapters relative to one another and to the target and does not necessarily mean that the sequence may not include additional sequences, such as linker sequences, for example.

Other libraries may be prepared in a similar manner, each including at least one library-specific index tag sequence or combinations of index tag sequences different than an index tag sequence or combination of index tag sequences from the other libraries.

A clean-up process, such as described above, may be performed on the resulting template polynucleotides having the amplified adapter-template-amplified adapter sequences.

The resulting adapter-target-adapter polynucleotides, whether or not first subjected to cleaned-up, along with any unincorporated adapter or primer oligonucleotides or remaining polynucleotides species are subjected to 3' blocking.

3' Blocking

In one embodiment, in addition to reducing or eliminating the amount of undesirable molecules, such as unligated adapters and/or incomplete products, the combined ligated polynucleotide sequences (the adaptor-target-adaptor molecules) and undesirable molecules, e.g., unligated universal adapter polynucleotides, are optionally 3' blocked, meaning that the polynucleotides are modified to prevent incorporation of nucleotides on the 3' end to extend the polynucleotide or the oligonucleotide from the 3' end. 3' blocking may be performed on each library separately or on pooled libraries.

The resulting composition may be subjected to a 3' blocking reaction to block the 3' ends of the polynucleotides or oligonucleotides in the sample, such as adapter-target-adapter polynucleotides or residual unligated universal adapters. Extension of an oligonucleotide or polynucleotide having "blocked" 3' end by the addition of additional nucleotides in a 5' to 3' direction is prevented due to the blocked 3' end.

The 3' blocking may be accomplished in any suitable manner. In some embodiments, a blocking moiety may be covalently attached to a 3' hydroxyl group at the 3' end to prevent extension from the 3' end. 3' blocking may be performed on each library separately or on pooled libraries. Preferably, 3' blocking is performed on pooled libraries.

3' blocked means that polynucleotides are modified to prevent incorporation of nucleotides on the 3' end to extend the polynucleotide from the 3' end or to prevent digestion by an enzyme having 3' exonuclease activity. Preferably, the 3' ends are blocked to prevent incorporation of nucleotides on the 3' end to extend the polynucleotide from the 3' end. More preferably, the 3' ends are blocked to prevent incorporation of nucleotides on the 3' end to extend the polynucleotide from the 3' end and to prevent digestion by an enzyme having 3' exonuclease activity.

In some embodiments, the 3'-OH blocking group may be removable, such that the 3' carbon atom has attached a group of the structure —O—Z, wherein Z is any of $C(R')_2$—O—R", $C(R')_2$—$N(R")_2$, $C(R')_2$—N(H)R", $C(R')_2$—S—R" and $C(R')_2$—F, wherein each R" is or is part of a removable protecting group; each R' is independently a hydrogen atom, an alkyl, substituted alkyl, arylalkyl, alkenyl, alkynyl, aryl, heteroaryl, heterocyclic, acyl, cyano, alkoxy, aryloxy, heteroaryloxy or amido group, or a detectable label attached through a linking group; or $(R')_2$ represents an alkylidene group of formula $=C(R''')_2$ wherein each R''' may be the same or different and is selected from the group comprising hydrogen and halogen atoms and alkyl groups; and wherein said molecule may be reacted to yield an intermediate in which each R" is exchanged for H or, where Z is $C(R')_2$—F, the F is exchanged for OH, SH or $NH_2$, preferably OH, which intermediate dissociates under aqueous conditions to afford a molecule with a free 3'OH; with the proviso that where Z is $C(R')_2$—S—R", both R' groups are not H. Where the blocking group is any of $C(R')_2$—O—R", $C(R')_2$—N$(R")_2$, $C(R')_2$—N(H)R", $C(R')_2$—S—R" and $C(R')_2$—F, i.e. of formula Z, each R' may be independently H or an alkyl. Preferably, Z is of formula $C(R')_2$—O—R", $C(R')_2$—N$(R")_2$, $C(R')_2$—N(H)R" and $C(R')_2$—SR". Particularly preferably, Z is of the formula $C(R')_2$—O—R", $C(R')_2$—N$(R")_2$, and $C(R')_2$—SR". R" may be a benzyl group or a substituted benzyl group. One example of groups of structure O—Z wherein Z is $C(R')_2$—N$(R")_2$ are those in which N$(R")_2$ is azido (—$N_3$). One such example is azidomethyl wherein each R' is H. Alternatively, R' in Z groups of formula $C(R')_2$—$N_3$ and other Z groups may be any of the other groups discussed herein. Examples of typical R' groups include $C_{1-6}$ alkyl, particularly methyl and ethyl. Other non-limiting examples of suitable 3' blocking groups are provided in Greene et al., "Protective Groups in Organic Synthesis," John Wiley & Sons, New York (1991), U.S. Pat. Nos. 5,990,300, 5,872,244, 6,232,465, 6,214,987, 5,808, 045, 5,763,594, 7,057,026, 7,566,537, 7,785,796, 8,148,064, 8,394,586, 9,388,463, 9,410,200, 7,427,673, 7,772,384, 8,158,346, 9,121,062, 7,541,444, 7,771,973, 8,071,739, 8,597,881, 9,121,060, 9,388,464, 8,399,188, 8,808,988, 9,051,612, 9,469,873, and U.S. Pub. Nos. 2016/0002721 and 2016/0060692, the entire contents of which are incorporated herein by reference.

In some embodiments, the blocking group may remain covalently bound during subsequent processes associated with immobilizing adapter-target-adapter polynucleotides to a solid surface and sequencing.

In some embodiments, a dideoxynucleotide (ddNTP) is incorporated onto the 3' end of a polynucleotide to block the 3' end. The ddNTP may be incorporated in any suitable manner. In some embodiments, a ddNTP is incorporated via a terminal deoxynucleotidyl transferase (TdT). TdTs are able to incorporated nucleotides onto a 3' end of single or double stranded DNA without a template. In some embodiments, a ddNTP is incorporated onto a 3' end via a TdT in the presence of a DNA polymerase, such as, for example, Pol19, Pol812 or Pol963 polymerase. Non-limiting examples of other suitable polymerases are provided in U.S. Pat. Nos. 8,460,910, 8,852,910, 8,623,628, 9,273,352, 9,447,389, and U.S. Pub. Nos. 2015/0376582, 2016/0032377, 2016/0090579, 2016/0115461, the entire contents of which are incorporated herein by reference.

In some embodiments, a digoxigenin-labeled dideoxyuridine triphosphate is added to the 3' end using terminal transferase to block the 3' end. Kits for adding digoxigenin-labeled dideoxyuridine triphosphate to a 3' end of a polynucleotide are available from, for example, Sigma-Aldrich.

Any other suitable process may also be employed to modify the 3' ends of the polynucleotides.

During or following 3' blocking a number of compounds and compositions may result. For example, a compound or composition comprising a polynucleotide having a first adapter-target-second adapter sequence or an adapter-target-adapter sequence of nucleotides in which a 3' end of the polynucleotide is blocked may result. A library or a composition comprising a plurality of such 3' blocked polynucleotides may result. Pooled libraries and composition comprising pooled libraries of such polynucleotides may result. The compositions may further comprise adapter oligonucleotides (e.g., universal adapters) that are not attached to the target polynucleotides. A polynucleotide may result that has a first adapter-target-second adapter sequence or an adapter-target-adapter sequence of nucleotides in which a 5' ends of the polynucleotides are blocked and the 3' ends of the polynucleotide is blocked. Compositions or libraries comprising the 5' modified and 3' blocked polynucleotides may result. Pooled libraries and composition comprising pooled libraries of such polynucleotides may result.

By way of further example, a composition comprising such polynucleotides and an enzyme and reagent for blocking 3' ends of the polynucleotide may result. Similarly, a composition comprising a library of polynucleotides and the enzyme and reagent may result. Compositions comprising pooled libraries of such polynucleotides and the enzyme and reagent may result. In some embodiments, the compositions comprise a ddNTP. The compositions may further comprise a TdT. The compositions may further comprise a DNA polymerase, such as, for example, Pol19, Pol812 or Pol963 polymerase.

A clean-up process, such as described above, may be performed following blocking. For instance, a clean-up step may occur prior to immobilizing the polynucleotides on a solid surface for sequencing. If the libraries have not been pooled, they may be pooled prior to immobilizing on a surface of sequencing.

Methods for reducing or eliminating the amount of unligated universal adapter polynucleotide constructs, and methods for 3' blocking polynucleotides can be performed concurrently, or sequentially in any order.

In some embodiments, the exonuclease treatment described herein to reduce or eliminate unligated universal adaptors can be used immediately following the ligation, or can be used following the PCR based methods to add a universal extension primer binding site.

Exonuclease Treatment

Solutions or compositions comprising the resulting adapter-target-adapter polynucleotides, whether or not first subjected to cleanup, along with any unincorporated adapter oligonucleotides or target polynucleotides are subjected to treatment with an exonuclease. In one embodiment, the exonuclease treatment has 3' exonuclease activity to degrade any polynucleotides that remain that are not 3' blocked. In one embodiment, an exonuclease digests polynucleotides having an unprotected 5' end or an unprotected 3' end, including the unincorporated adapters. In embodiments having exonuclease resistant 5' ends, the exonuclease may have both 5' exonuclease activity and 3' exonuclease activity.

Any suitable exonuclease may be used. In one embodiment, the exonuclease has 5' and 3' exonuclease activity. An exonuclease that has "5' exonuclease activity" is an exonuclease that digests DNA in a 5' to 3' direction. An exonuclease that has "3' exonuclease activity" is an exonuclease that digests DNA in a 3' to 5' direction. The exonuclease may comprise activity for double-stranded DNA without nicking. One example of a suitable exonuclease that has 5' and 3' exonuclease activity and has activity for double-stranded DNA without nicking is Exonuclease V, which is a RecBCD complex from *E. coli* and is available from, for example, New England Biolabs (Cat #M0345S/L).

In one embodiment, undesirable molecules such as the unligated universal adapter polynucleotide constructs are removed by exonuclease. In one embodiment, exonucleases useful herein have a 5' to 3' DNA exonuclease activity, and optionally, an exonuclease is biased for double stranded DNA. In one embodiment, an exonuclease specifically targets the 5' end of a double stranded DNA, where the 5' end has a 5' phosphate. In another embodiment, an exonuclease specifically targets the 5' end of a double stranded DNA, where the 5' end does not have a 5' phosphate. Without intending to be limiting, use of exonucleases useful herein having a 5' to 3' DNA exonuclease activity is designed to remove at least one strand of unligated universal adaptors by digestion at the 5' end of the double stranded region of the universal adaptors.

In one embodiment, an exonuclease useful herein has a 5' to 3' DNA exonuclease activity that is biased for double stranded DNA having a 5' phosphate at the 5' end of the region of double stranded nucleic acid of a universal adapter. Examples of 5' to 3' exonucleases biased for dsDNA having a 5' phosphate at the 5' end of the region of double stranded nucleic acid include, but are not limited to, lambda exonuclease (New England Biolabs). The presence of the 5' phosphate at the 5' end of the double-stranded region biases an exonuclease such as lambda exonuclease for the 5' end of the double-stranded region of an unligated universal adapter. In one embodiment, the 5' end of the strand that is part of the region of single stranded non-complementary nucleic acid strands does not include a 5' phosphate. In one embodiment, the 5' end of the strand that is part of the single stranded region is modified to reduce the ability of the exonuclease to use it as a substrate.

In another embodiment, an exonuclease useful herein has both 5' to 3' and 3' to 5' DNA exonuclease activity. When such an exonuclease is biased for double stranded DNA but also uses single stranded DNA as a substrate, universal adapters used for ligation can include two types of modifications. One modification is at the 3' end of the single stranded region to block the 3' to 5' DNA exonuclease activity. This modification prevents digestion of adaptor-target-adaptor molecules from the free 3' ends. The second modification is at the 5' end of the strand that is part of the region of single stranded non-complementary nucleic acid strands. This modification prevents digestion of adaptor-target-adaptor molecules from the free 5' ends. Examples of modifications include, but are not limited to, inclusion of phosphorothioate linkages. Examples of exonucleases having a 5' to 3' DNA exonuclease activity and 3' to 5' DNA exonuclease activity, and biased for double stranded DNA, include but are not limited to exonuclease VIII truncated (New England Biolabs).

In a preferred embodiment, undesirable molecules such as incomplete products are removed by exonuclease. In one embodiment, exonucleases useful herein have a 3' to 5' DNA exonuclease activity, and optionally, an exonuclease is biased for double stranded DNA that is blunt ended or has a recessed 3' terminus. In one embodiment, an exonuclease having a 3' to 5' DNA exonuclease activity has reduced activity on single stranded DNA (e.g., it is biased for double stranded DNA) and/or reduced activity on a 3' extension when the single strand is 4 or more bases in length (e.g., it is biased for double stranded DNA that has a single stranded 3' extension of 3 bases or less). Without intending to be limiting, use of exonucleases useful herein having a 3' to 5' DNA exonuclease activity is designed to remove at least one strand of incomplete products by digestion at the 3' end of the double stranded region of the incomplete product. Examples of incomplete products include adaptor-target molecules, and target molecules that do not include an adaptor at either end. Examples of 3' to 5' exonucleases biased for double stranded DNA having blunt or recessed 3' termini include, but are not limited to, Exonuclease III (New England Biolabs).

In some embodiments, two exonucleases may be employed, one having 5' exonuclease activity and the other having 3' exonuclease activity. Examples of exonucleases that have 5' exonuclease activity include lambda exonuclease (New England Biolabs) and Exonuclease VIII truncated (New England Biolabs). An example of an exonuclease having 3' exonuclease activity is Exonuclease T (New England Biolabs).

Exonuclease treatment may be performed on each library separately or on pooled libraries. Following exonuclease treatment, a clean-up step, such as described above, may be performed prior to immobilizing the polynucleotides on a solid surface for sequencing.

If the libraries have not been pooled, they may be pooled prior to immobilizing on a surface of sequencing.

During or following exonuclease treatment a number of compounds and compositions may result. For example, a compound or composition comprising a polynucleotide having an adapter-target-adapter sequence of nucleotides in which a 3' end of the polynucleotide is blocked for exonuclease activity may result. A library or a composition comprising a plurality of such 3' blocked polynucleotides may result. Pooled libraries and composition comprising pooled libraries of such polynucleotides may result. The compositions may further comprise universal adapters that are not attached to the target polynucleotides, and/or incomplete products.

By way of further example, a composition comprising a polynucleotide having an adapter-target-adapter sequence of nucleotides and an exonuclease may result. Similarly, a composition comprising a library polynucleotides and the exonuclease may result. Compositions comprising pooled libraries of such polynucleotides and the exonuclease may result. The compositions may further comprise universal adapters that are not attached to the target polynucleotides.

Preparation of Immobilized Samples for Sequencing

The plurality of molecules, e.g., first adapter-target-second adapter or adapter-target-adapter, from one or more sources are then immobilized and amplified prior to sequencing. Methods for attaching adapter-target-adapter molecules from one or more sources to a substrate are known in the art. Likewise, methods for amplifying immobilized adapter-target-adapter molecules include, but are not limited to, bridge amplification and kinetic exclusion. Methods for immobilizing and amplifying prior to sequencing are described in, for instance, Bignell et al. (U.S. Pat. No. 8,053,192), Gunderson et al. (WO2016/130704), Shen et al. (U.S. Pat. No. 8,895,249), and Pipenburg et al. (U.S. Pat. No. 9,309,502).

The pooled library preparations, e.g., 5' modified and/or 3' blocked library preparations, may then be immobilized on a solid surface for in preparation for sequencing. Sequencing may be performed as an array of single molecules, or may be amplified prior to sequencing. The amplification may be carried out using one or more immobilized primers. The immobilized primer(s) may be a lawn on a planar surface, clusters on a planar surface, in wells of a multi-well structure, on a pool of beads, or the like. The pool of beads may be isolated into an emulsion with a single bead in each "compartment" of the emulsion. At a concentration of only one template per "compartment", only a single template is amplified on each bead.

The term "solid-phase amplification" as used herein refers to any polynucleotide amplification reaction carried out on or in association with a solid support such that all or a portion of the amplified products are immobilized on the solid support as they are formed. In particular, the term encompasses solid-phase polymerase chain reaction (solid-phase PCR) and solid phase isothermal amplification which are reactions analogous to standard solution phase amplification, except that one or both of the forward and reverse amplification primers is/are immobilized on the solid support. Solid phase PCR covers systems such as emulsions, wherein one primer is anchored to a bead and the other is in free solution, and colony formation in solid phase gel matrices wherein one primer is anchored to the surface, and one is in free solution.

Although the disclosure encompasses "solid-phase" amplification methods in which only one amplification primer is immobilized (the other primer usually being present in free solution), it is preferred for the solid support to be provided with both the forward and the reverse primers immobilized. In practice, there will be a "plurality" of identical forward primers and/or a "plurality" of identical reverse primers immobilized on the solid support, since the amplification process requires an excess of primers to sustain amplification. References herein to forward and reverse primers are to be interpreted accordingly as encompassing a "plurality" of such primers unless the context indicates otherwise.

As will be appreciated by the skilled reader, any given amplification reaction requires at least one type of forward primer and at least one type of reverse primer specific for the template to be amplified. However, in certain embodiments the forward and reverse primers may comprise template-specific portions of identical sequence, and may have entirely identical nucleotide sequence and structure (including any non-nucleotide modifications). In other words, it is possible to carry out solid-phase amplification using only one type of primer, and such single-primer methods are encompassed within the scope of the invention. Other embodiments may use forward and reverse primers which contain identical template-specific sequences but which differ in some other structural features. For example one type of primer may contain a non-nucleotide modification which is not present in the other.

Throughout this disclosure, the terms "P5" and "P7" are used when referring to adapters and/or amplification primers. It will be understood that any suitable amplification primers can be used in the methods presented herein, and that the use of P5 and P7 are exemplary embodiments only. Uses of amplification primers such as P5 and P7 on flowcells is known in the art, as exemplified by the disclosures of WO 2007/010251, WO 2006/064199, WO 2005/065814, WO 2015/106941, WO 1998/044151, and WO 2000/018957, each of which is incorporated by reference in its entirety. For example, any suitable forward amplification primer, whether immobilized or in solution, can be useful in the methods presented herein for hybridization to a complementary sequence and amplification of a sequence. Similarly, any suitable reverse amplification primer, whether immobilized or in solution, can be useful in the methods presented herein for hybridization to a complementary sequence and amplification of a sequence. One of skill in the art will understand how to design and use primer sequences that are suitable for capture, and amplification of nucleic acids as presented herein.

Solid supports comprised of an inert substrate or matrix (e.g. glass slides, polymer beads, etc) may be "functionalized", for example by application of a layer or coating of an intermediate material comprising reactive groups which permit covalent attachment to biomolecules, such as polynucleotides. Examples of such supports include, but are not limited to, polyacrylamide hydrogels supported on an inert substrate such as glass. In such embodiments, the biomolecules (e.g. polynucleotides) may be directly covalently attached to the intermediate material (e.g. the hydrogel), but the intermediate material may itself be non-covalently attached to the substrate or matrix (e.g. the glass substrate). The term "covalent attachment to a solid support" is to be interpreted accordingly as encompassing this type of arrangement.

The pooled library samples may be amplified on a solid surface contains a forward and reverse amplification primer. In some embodiments, the pooled libraries of polynucleotides are used to prepare clustered arrays of polynucleic acid colonies, analogous to those described in U.S. Pat. Pub. No. 2005/0100900, U.S. Pat. No. 7,115,400, WO 00/18957 and WO 98/44151, by solid-phase amplification and more particularly solid phase isothermal amplification. The terms "cluster" and "colony" are used interchangeably herein to refer to a discrete site on a solid support comprised of a plurality of identical immobilized nucleic acid strands and a plurality of identical immobilized complementary nucleic acid strands. The term "clustered array" refers to an array formed from such clusters or colonies. In this context the term "array" is not to be understood as requiring an ordered arrangement of clusters.

The term solid phase, or surface, is used to mean either a planar array wherein primers are attached to a flat surface, for example, glass, silica or plastic microscope slides or similar flow cell devices; beads, wherein either one or two primers are attached to the beads and the beads are amplified; an array of beads on a surface after the beads have been amplified; or the like.

The terms "solid surface," "solid support" and other grammatical equivalents herein refer to any material that is appropriate for or may be modified to be appropriate for the attachment of the template polynucleotides. As will be appreciated by those in the art, the number of possible substrates is very large. Possible substrates include, but are not limited to, glass and modified or functionalized glass, plastics (including acrylics, polystyrene and copolymers of styrene and other materials, polypropylene, polyethylene, polybutylene, polyurethanes, Teflon®, etc.), polysaccharides, nylon or nitrocellulose, ceramics, resins, silica or silica-based materials including silicon and modified silicon, carbon, metals, inorganic glasses, plastics, optical fiber bundles, and a variety of other polymers. Particularly useful solid supports and solid surfaces for some embodiments are located within a flow cell apparatus. Exemplary flow cells are set forth in further detail below.

In some embodiments, the solid support comprises a patterned surface. A "patterned surface" refers to an arrangement of different regions in or on an exposed layer of a solid support. For example, one or more of the regions may be features where one or more amplification primers are pres-ent. The features may be separated by interstitial regions where amplification primers are not present. In some embodiments, the pattern may be an x-y format of features that are in rows and columns. In some embodiments, the pattern may be a repeating arrangement of features and/or interstitial regions. In some embodiments, the pattern may be a random arrangement of features and/or interstitial regions. Exemplary patterned surfaces that may be used in the methods and compositions set forth herein are described in U.S. Pat. Nos. 8,778,848, 8,778,849, 9,079,148, and U.S. Pub. No. 2014/0243224.

In some embodiments, the solid support comprises an array of wells or depressions in a surface. This may be fabricated as is generally known in the art using a variety of techniques, including, but not limited to, photolithography, stamping techniques, molding techniques and microetching techniques. As will be appreciated by those in the art, the technique used will depend on the composition and shape of the array substrate.

The features in a patterned surface may be wells in an array of wells (e.g. microwells or nanowells) on glass, silicon, plastic or other suitable solid supports with patterned, covalently-linked gel such as poly(N-(5-azidoacet-amidylpentyl)acrylamide-co-acrylamide)(PAZAM, see, for example, U.S. Pub. No. 2013/184796, WO 2016/066586, and WO 2015/002813). The process creates gel pads used for sequencing that may be stable over sequencing runs with a large number of cycles. The covalent linking of the polymer to the wells is helpful for maintaining the gel in the structured features throughout the lifetime of the structured substrate during a variety of uses. However in many embodiments, the gel need not be covalently linked to the wells. For example, in some conditions silane free acrylamide (SFA, see, for example, U.S. Pat. No. 8,563,477) which is not covalently attached to any part of the structured substrate, may be used as the gel material.

In particular embodiments, a structured substrate may be made by patterning a solid support material with wells (e.g. microwells or nanowells), coating the patterned support with a gel material (e.g. PAZAM, SFA or chemically modified variants thereof, such as the azidolyzed version of SFA (azido-SFA)) and polishing the gel coated support, for example via chemical or mechanical polishing, thereby retaining gel in the wells but removing or inactivating substantially all of the gel from the interstitial regions on the surface of the structured substrate between the wells. Primer nucleic acids may be attached to gel material. A solution of target nucleic acids (e.g. a fragmented human genome) may then be contacted with the polished substrate such that individual target nucleic acids will seed individual wells via interactions with primers attached to the gel material; however, the target nucleic acids will not occupy the interstitial regions due to absence or inactivity of the gel material. Amplification of the target nucleic acids will be confined to the wells since absence or inactivity of gel in the interstitial regions prevents outward migration of the growing nucleic acid colony. The process is conveniently manufacturable, being scalable and utilizing conventional micro- or nano-fabrication methods.

The term "flowcell" as used herein refers to a chamber comprising a solid surface across which one or more fluid reagents may be flowed. Examples of flowcells and related fluidic systems and detection platforms that may be readily used in the methods of the present disclosure are described, for example, in Bentley et al., *Nature* 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082.

In some embodiments, the solid support or its surface is non-planar, such as the inner or outer surface of a tube or vessel. In some embodiments, the solid support comprises microspheres or beads. By "microspheres" or "beads" or "particles" or grammatical equivalents herein is meant small discrete particles. Suitable bead compositions include, but are not limited to, plastics, ceramics, glass, polystyrene, methylstyrene, acrylic polymers, paramagnetic materials, thoria sol, carbon graphite, titanium dioxide, latex or cross-linked dextrans such as Sepharose, cellulose, nylon, cross-linked micelles and Teflon®, as well as any other materials outlined herein for solid supports may all be used. "Micro-sphere Detection Guide" from Bangs Laboratories, Fishers Ind. is a helpful guide. In certain embodiments, the micro-spheres are magnetic microspheres or beads.

The beads need not be spherical; irregular particles may be used. Alternatively or additionally, the beads may be porous. The bead sizes range from nanometers, i.e. 100 nm, to millimeters, i.e. 1 mm, with beads from about 0.2 micron to about 200 microns being preferred, and from about 0.5 to about 5 micron being particularly preferred, although in some embodiments smaller or larger beads may be used.

Clustered arrays may be prepared using either a process of thermocycling, as described in WO/9844151, or a process whereby the temperature is maintained as a constant, and the cycles of extension and denaturing are performed using changes of reagents. Such isothermal amplification methods are described in patent application numbers WO/0246456 and US 2008/0009420. Due to the lower temperatures required in the isothermal process, this is particularly preferred.

It will be appreciated that any of the amplification methodologies described herein or generally known in the art may be utilized with universal or target-specific primers to amplify immobilized DNA fragments. Suitable methods for amplification include, but are not limited to, the polymerase chain reaction (PCR), strand displacement amplification (SDA), transcription mediated amplification (TMA) and nucleic acid sequence based amplification (NASBA), as described in U.S. Pat. No. 8,003,354, which is incorporated herein by reference in its entirety. The above amplification methods may be employed to amplify one or more nucleic acids of interest. For example, PCR, including multiplex PCR, SDA, TMA, NASBA and the like may be utilized to amplify immobilized DNA fragments. In some embodiments, primers directed specifically to the polynucleotide of interest are included in the amplification reaction.

Other suitable methods for amplification of polynucleotides may include oligonucleotide extension and ligation, rolling circle amplification (RCA) (Lizardi et al., *Nat. Genet.* 19:225-232 (1998)) and oligonucleotide ligation assay (OLA) (See generally U.S. Pat. Nos. 7,582,420, 5,185,243, 5,679,524 and 5,573,907; EP 0 320 308 B1; EP 0 336 731 B1; EP 0 439 182 B1; WO 90/01069; WO 89/12696; and WO 89/09835) technologies. It will be appreciated that these amplification methodologies may be designed to amplify immobilized DNA fragments. For example, in some embodiments, the amplification method may include liga-tion probe amplification or oligonucleotide ligation assay (OLA) reactions that contain primers directed specifically to the nucleic acid of interest. In some embodiments, the amplification method may include a primer extension-ligation reaction that contains primers directed specifically to the nucleic acid of interest. As a non-limiting example of primer extension and ligation primers that may be specifically designed to amplify a nucleic acid of interest, the amplification may include primers used for the GoldenGate assay (Illumina, Inc., San Diego, CA) as exemplified by U.S. Pat. Nos. 7,582,420 and 7,611,869.

Exemplary isothermal amplification methods that may be used in a method of the present disclosure include, but are not limited to, Multiple Displacement Amplification (MDA) as exemplified by, for example Dean et al., *Proc. Natl. Acad. Sci. USA* 99:5261-66 (2002) or isothermal strand displace-ment nucleic acid amplification exemplified by, for example U.S. Pat. No. 6,214,587. Other non-PCR-based methods that may be used in the present disclosure include, for example, strand displacement amplification (SDA) which is described in, for example Walker et al., Molecular Methods for Virus Detection, Academic Press, Inc., 1995; U.S. Pat. Nos. 5,455, 166, and 5,130,238, and Walker et al., *Nucl. Acids Res.* 20:1691-96 (1992) or hyper-branched strand displacement amplification which is described in, for example Lage et al., *Genome Res.* 13:294-307 (2003). Isothermal amplification methods may be used with the strand-displacing Phi 29 polymerase or Bst DNA polymerase large fragment, 5'→3' exo-for random primer amplification of genomic DNA. The use of these polymerases takes advantage of their high processivity and strand displacing activity. High processiv-ity allows the polymerases to produce fragments that are 10-20 kb in length. As set forth above, smaller fragments may be produced under isothermal conditions using poly-merases having low processivity and strand-displacing activity such as Klenow polymerase. Additional description of amplification reactions, conditions and components are set forth in detail in the disclosure of U.S. Pat. No. 7,670, 810, which is incorporated herein by reference in its entirety.

Another polynucleotide amplification method that is use-ful in the present disclosure is Tagged PCR which uses a population of two-domain primers having a constant 5' region followed by a random 3' region as described, for example, in Grothues et al. *Nucleic Acids Res.* 21(5):1321-2 (1993). The first rounds of amplification are carried out to allow a multitude of initiations on heat denatured DNA based on individual hybridization from the randomly-syn-thesized 3' region. Due to the nature of the 3' region, the sites of initiation are contemplated to be random throughout the genome. Thereafter, the unbound primers may be removed and further replication may take place using primers complementary to the constant 5' region.

In some embodiments, isothermal amplification can be performed using kinetic exclusion amplification (KEA), also referred to as exclusion amplification (ExAmp). A nucleic acid library of the present disclosure can be made using a method that includes a step of reacting an amplification reagent to produce a plurality of amplification sites that each includes a substantially clonal population of amplicons from an individual target nucleic acid that has seeded the site. In some embodiments the amplification reaction proceeds until a sufficient number of amplicons are generated to fill the capacity of the respective amplification site. Filling an already seeded site to capacity in this way inhibits target nucleic acids from landing and amplifying at the site thereby producing a clonal population of amplicons at the site. In some embodiments, apparent clonality can be achieved even if an amplification site is not filled to capacity prior to a second target nucleic acid arriving at the site. Under some conditions, amplification of a first target nucleic acid can proceed to a point that a sufficient number of copies are made to effectively outcompete or overwhelm production of copies from a second target nucleic acid that is transported to the site. For example, in an embodiment that uses a bridge amplification process on a circular feature that is smaller than 500 nm in diameter, it has been determined that after 14 cycles of exponential amplification for a first target nucleic acid, contamination from a second target nucleic acid at the same site will produce an insufficient number of contaminating amplicons to adversely impact sequencing-by-synthesis analysis on an Illumina sequencing platform.

As demonstrated by the above example, amplification sites in an array can be, but need not be, entirely clonal in particular embodiments. Rather, for some applications, an individual amplification site can be predominantly populated with amplicons from a first target nucleic acid and can also have a low level of contaminating amplicons from a second target nucleic acid. An array can have one or more amplification sites that have a low level of contaminating amplicons so long as the level of contamination does not have an unacceptable impact on a subsequent use of the array. For example, when the array is to be used in a detection application, an acceptable level of contamination would be a level that does not impact signal to noise or resolution of the detection technique in an unacceptable way. Accordingly, apparent clonality will generally be relevant to a particular use or application of an array made by the methods set forth herein. Exemplary levels of contamination that can be acceptable at an individual amplification site for particular applications include, but are not limited to, at most 0.1%, 0.5%, 1%, 5%, 10% or 25% contaminating amplicons. An array can include one or more amplification sites having these exemplary levels of contaminating amplicons. For example, up to 5%, 10%, 25%, 50%, 75%, or even 100% of the amplification sites in an array can have some contaminating amplicons. It will be understood that in an array or other collection of sites, at least 50%, 75%, 80%, 85%, 90%, 95% or 99% or more of the sites can be clonal or apparently clonal.

In some embodiments, kinetic exclusion can occur when a process occurs at a sufficiently rapid rate to effectively exclude another event or process from occurring. Take for example the making of a nucleic acid array where sites of the array are randomly seeded with target nucleic acids from a solution and copies of the target nucleic acid are generated in an amplification process to fill each of the seeded sites to capacity. In accordance with the kinetic exclusion methods of the present disclosure, the seeding and amplification processes can proceed simultaneously under conditions where the amplification rate exceeds the seeding rate. As such, the relatively rapid rate at which copies are made at a site that has been seeded by a first target nucleic acid will effectively exclude a second nucleic acid from seeding the site for amplification. Kinetic exclusion amplification methods can be performed as described in detail in the disclosure of U.S. Pub. No. 2013/0338042, which is incorporated herein by reference in its entirety.

Kinetic exclusion can exploit a relatively slow rate for initiating amplification (e.g. a slow rate of making a first copy of a target nucleic acid) vs. a relatively rapid rate for making subsequent copies of the target nucleic acid (or of the first copy of the target nucleic acid). In the example of the previous paragraph, kinetic exclusion occurs due to the relatively slow rate of target nucleic acid seeding (e.g. relatively slow diffusion or transport) vs. the relatively rapid rate at which amplification occurs to fill the site with copies of the nucleic acid seed. In another exemplary embodiment, kinetic exclusion can occur due to a delay in the formation of a first copy of a target nucleic acid that has seeded a site (e.g. delayed or slow activation) vs. the relatively rapid rate at which subsequent copies are made to fill the site. In this example, an individual site may have been seeded with several different target nucleic acids (e.g. several target nucleic acids can be present at each site prior to amplification). However, first copy formation for any given target nucleic acid can be activated randomly such that the average rate of first copy formation is relatively slow compared to the rate at which subsequent copies are generated. In this case, although an individual site may have been seeded with several different target nucleic acids, kinetic exclusion will allow only one of those target nucleic acids to be amplified. More specifically, once a first target nucleic acid has been activated for amplification, the site will rapidly fill to capacity with its copies, thereby preventing copies of a second target nucleic acid from being made at the site.

An amplification reagent can include further components that facilitate amplicon formation and, in some cases, increase the rate of amplicon formation. An example is a recombinase. Recombinase can facilitate amplicon formation by allowing repeated invasion/extension. More specifically, recombinase can facilitate invasion of a target nucleic acid by the polymerase and extension of a primer by the polymerase using the target nucleic acid as a template for amplicon formation. This process can be repeated as a chain reaction where amplicons produced from each round of invasion/extension serve as templates in a subsequent round. The process can occur more rapidly than standard PCR since a denaturation cycle (e.g. via heating or chemical denaturation) is not required. As such, recombinase-facilitated amplification can be carried out isothermally. It is generally desirable to include ATP, or other nucleotides (or in some cases non-hydrolyzable analogs thereof) in a recombinase-facilitated amplification reagent to facilitate amplification. A mixture of recombinase and single stranded binding (SSB) protein is particularly useful as SSB can further facilitate amplification. Exemplary formulations for recombinase-facilitated amplification include those sold commercially as TwistAmp kits by TwistDx (Cambridge, UK). Useful components of recombinase-facilitated amplification reagent and reaction conditions are set forth in U.S. Pat. Nos. 5,223,414 and 7,399,590, the contents of which are incorporated herein by reference.

Another example of a component that can be included in an amplification reagent to facilitate amplicon formation and in some cases to increase the rate of amplicon formation is a helicase. Helicase can facilitate amplicon formation by allowing a chain reaction of amplicon formation. The process can occur more rapidly than standard PCR since a denaturation cycle (e.g. via heating or chemical denaturation) is not required. As such, helicase-facilitated amplification can be carried out isothermally. A mixture of helicase and single stranded binding (SSB) protein is particularly useful as SSB can further facilitate amplification. Exemplary formulations for helicase-facilitated amplification include those sold commercially as IsoAmp kits from Biohelix (Beverly, MA). Further, examples of useful formulations that include a helicase protein are described in U.S. Pat. Nos. 7,399,590 and 7,829,284, each of which is incorporated herein by reference.

Yet another example of a component that can be included in an amplification reagent to facilitate amplicon formation and in some cases increase the rate of amplicon formation is an origin binding protein.

Use in Sequencing/Methods of Sequencing

The immobilized polynucleotides from the pooled libraries may be sequenced in any suitable manner. Preferably, sequencing is performed by sequencing by synthesis in which nucleotides are added successively to a free 3' hydroxyl group of a sequencing primer using the immobilized polynucleotides as a template, resulting in synthesis of a polynucleotide chain in the 5' to 3' direction. The nature of the nucleotide added is preferably determined after each nucleotide addition. Sequencing techniques using sequencing by ligation, wherein not every contiguous base is sequenced, and techniques such as massively parallel signature sequencing (MPSS) where bases are removed from, rather than added to the strands on the surface are also within the scope of the disclosure, as are techniques using detection of pyrophosphate release (pyrosequencing). Such pyrosequencing based techniques are particularly applicable to sequencing arrays of beads where the beads have been amplified in an emulsion such that a single template from the library molecule is amplified on each bead.

The initiation point for the sequencing reaction may be provided by annealing of a sequencing primer to a product of the solid-phase amplification reaction. In this connection, one or both of the adapters added during formation of the template library may include a nucleotide sequence which permits annealing of a sequencing primer to immobilized polynucleotides, such as the adapter-target-adapter polynucleotides.

The index tag sequence and target sequence may be determined in a single read from a single sequencing primer, or in multiple reads from more than one sequencing primers. In the case of two reads from two sequencing primers, the "index tag read" and the "target read" may be performed in either order, with a suitable denaturing step to remove the annealed primer after the first sequencing read is completed. Suitable denaturing steps may include formamide, hydroxide or heat as generally known in the art.

The products of solid-phase amplification reactions where both forward and reverse amplification primers are covalently immobilized on the solid surface may be so-called "bridged" structures formed by annealing of pairs of immobilized polynucleotide strands and immobilized complementary strands, both strands being attached to the solid support at the 5' end. Arrays comprised of such bridged structures provide inefficient templates for nucleic acid sequencing, since hybridization of a conventional sequencing primer to one of the immobilized strands is not favored compared to annealing of this strand to its immobilized complementary strand under standard conditions for hybridization. Examples of bridged or cluster amplification are described in, for example, U.S. Pat. Nos. 7,985,565 and 7,115,400.

In order to provide more suitable templates for nucleic acid sequencing, it is preferred to remove substantially all or remove or displace at least a portion of one of the immobilized strands in the "bridged" structure to generate a template which is at least partially single-stranded. The portion of the template which is single-stranded will thus be available for hybridization to a sequencing primer. The process of removing all or a portion of one immobilized strand in a "bridged" double-stranded nucleic acid structure may be referred to herein as 'linearization', and is described in further detail in WO 2007/010251, WO 2006/064199, WO 2005/065814, WO 2015/106941, WO 1998/044151, and WO 2000/018957.

Bridged template structures may be linearized by cleavage of one or both strands with a restriction endonuclease or by cleavage of one strand with a nicking endonuclease. Other methods of cleavage may be used as an alternative to restriction enzymes or nicking enzymes, including inter alia chemical cleavage (e.g. cleavage of a diol linkage with periodate), cleavage of abasic sites by cleavage with endonuclease (for example 'USER', as supplied by NEB, Cat

M5505S), or by exposure to heat or alkali, cleavage of ribonucleotides incorporated into amplification products otherwise comprised of deoxyribonucleotides, photochemical cleavage or cleavage of a peptide linker.

It will be appreciated that a linearization step may not be essential if the solid-phase amplification reaction is performed with only one primer covalently immobilized and the other in free solution.

Following the cleavage step, regardless of the method used for cleavage, the product of the cleavage reaction may be subjected to denaturing conditions in order to remove the portion(s) of the cleaved strand(s) that are not attached to the solid support. Suitable denaturing conditions, for example sodium hydroxide solution, formamide solution or heat, will be apparent to the skilled reader with reference to standard molecular biology protocols (Sambrook et al., 2001, Molecular Cloning, A Laboratory Manual, 3rd Ed, Cold Spring Harbor Laboratory Press, Cold Spring Harbor Laboratory Press, NY; Current Protocols, eds. Ausubel et al.). Denaturation results in the production of a sequencing template which is partially or substantially single-stranded. A sequencing reaction may then be initiated by hybridization of a sequencing primer to the single-stranded portion of the template.

Thus, in some embodiments, a sequencing reaction comprises hybridizing a sequencing primer to a single-stranded region of a linearized amplification product, sequentially incorporating one or more nucleotides into a polynucleotide strand complementary to the region of amplified template strand to be sequenced, identifying the base present in one or more of the incorporated nucleotide(s) and thereby determining the sequence of a region of the template strand.

One preferred sequencing method which may be used relies on the use of modified nucleotides having removable 3' blocks, for example as described in WO 2004/018497 and U.S. Pat. No. 7,057,026. Once the modified nucleotide has been incorporated into the growing polynucleotide chain complementary to the region of the template being sequenced there is no free 3'—OH group available to direct further sequence extension and therefore the polymerase cannot add further nucleotides. Once the nature of the base incorporated into the growing chain has been determined, the 3' block may be removed to allow addition of the next successive nucleotide. By ordering the products derived using these modified nucleotides, it is possible to deduce the DNA sequence of the DNA template. Such reactions may be done in a single experiment if each of the modified nucleotides has a different label attached thereto, known to correspond to the particular base, to facilitate discrimination between the bases added during each incorporation step. Alternatively, a separate reaction may be carried out containing each of the modified nucleotides separately.

The modified nucleotides may carry a label to facilitate their detection. A fluorescent label, for example, may be used for detection of modified nucleotides. Each nucleotide type may thus carry a different fluorescent label, for example, as described in WO 2007/135368. The detectable label need not, however, be a fluorescent label. Any label may be used which allows the detection of an incorporated nucleotide.

One method for detecting fluorescently labelled nucleotides comprises using laser light of a wavelength specific for the labelled nucleotides, or the use of other suitable sources of illumination. The fluorescence from the label on the nucleotide may be detected by a CCD camera or other suitable detection means. Suitable instrumentation for recording images of clustered arrays is described in WO 2007/123744.

Of course, any other suitable sequencing method may be employed. Preferably, the sequencing method relies on successive incorporation of nucleotides into a polynucleotide chain. Suitable alternative techniques include, for example, pyrosequencing, FISSEQ (fluorescent in situ sequencing), MPSS and sequencing by ligation-based methods, for example as described is U.S. Pat. No. 6,306,597.

The nucleic acid sample may be further analyzed to obtain a second read from the opposite end of the fragment. Methodology for sequencing both ends of a cluster are described in WO 2007/010252 and WO 2008/041002. In one example, the series of steps may be performed as follows; generate clusters, linearize, hybridize first sequencing primer and obtain first sequencing read. The first sequencing primer may be removed, a second primer hybridized and the index tag sequenced. The poly nucleotide strand may then be "inverted" on the surface by synthesizing a complementary copy from the remaining immobilized primers used in cluster amplification. This process of strand resynthesize regenerates the double stranded cluster. The original template strand may be removed, to linearize the resynthesized strand that may then be annealed to a sequencing primer and sequenced in a third sequencing run.

In the cases where strand re-synthesis is employed, both strands may be immobilized to the surface in a way that allows subsequent release of a portion of the immobilized strand. This may be achieved through a number of mechanisms as described in WO 2007/010251. For example, one primer may contain a uracil nucleotide, which means that the strand may be cleaved at the uracil base using the enzymes uracil glycosylase (UDG) which removes the nucleoside base, and endonuclease VIII that excises the abasic nucleotide. This enzyme combination is available as USER™ enzyme from New England Biolabs (Cat #M5505). The second primer may comprise an 8-oxoguanine nucleotide, which is then cleavable by the enzyme FPG (NEB Cat #M0240). This design of primers provides control of which primer is cleaved at which point in the process, and also where in the cluster the cleavage occurs. The primers may also be chemically modified, for example with a disulfide or diol modification that allows chemical cleavage at specific locations.

Referring now to FIG. 1 a schematic drawing is shown of an adapter 100 that may be used in accordance with various embodiments described herein. The depicted adapter 100 comprises a double-stranded region 110 and a non-complementary single-stranded region 120. The double-stranded region 110 may be attached to a double-stranded target polynucleotide if the 3' ends are not blocked. In the depicted embodiment, each strand of the adapter 100 comprises a blocked 3' end, indicated by the "X." One depicted strand of the adapter 100 comprises a universal extension primer sequence 130, an index tag sequence 132, and a sequencing primer sequence 134. The other depicted strand of the adapter 100 comprises a universal extension primer sequence 140, an index tag sequence 142, and a sequencing primer sequence 144.

The universal extension primer sequences 130, 140 may hybridize to extension primer oligonucleotides attached to a solid surface for purposes of amplification or sequencing (if the adapter 100 was attached to a target polynucleotide). Universal extension primer sequence 140, or a portion thereof, may also hybridize to a sequencing primer for sequencing index tag sequence 142. Alternatively, the strand may comprise a further sequencing primer sequence (not shown).

Sequencing primer sequence 134 may hybridize to a sequencing primer to allow sequencing of index tag sequence 132. Index tag sequence 142 and index tag sequence 132 may be the same or different.

Sequencing primer sequence 144 may hybridize to a sequencing primer to allow sequencing of a target polynucleotide sequence (if attached to the adapter 100).

Sequencing primer sequences 134, 144 may hybridize to, for example, PCR primers if the adapters are attached to a target in a multi-step process as described above.

It will be understood that a suitable adapter for used in various embodiments described herein may have more or less sequence features, or other sequence features, than those described regarding FIG. 1.

Figure 2:
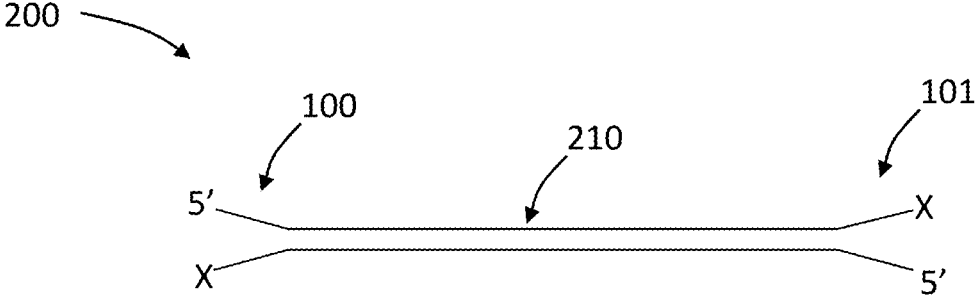
FIG. 2 is a schematic drawing of an embodiment of a template polynucleotide having an adapter-target-adapter sequence (which may include an adapter generally as shown in FIG. 1) according to various aspects of the disclosure presented herein.

Referring now to FIG. 2, a schematic drawing of a template polynucleotide 200 of a library having a first adapter 100—template 210—second adapter 101 sequence is shown. The template polynucleotide 210 is double stranded and attached to a double stranded portion of the first 100 and second 101 adapters. The first 100 and second 101 adapters may be the same or different. Preferably, the first 100 and second 101 adapters are the same. The 3' ends of the template polynucleotide 200 are blocked, e.g., as described above.

Figure 3:
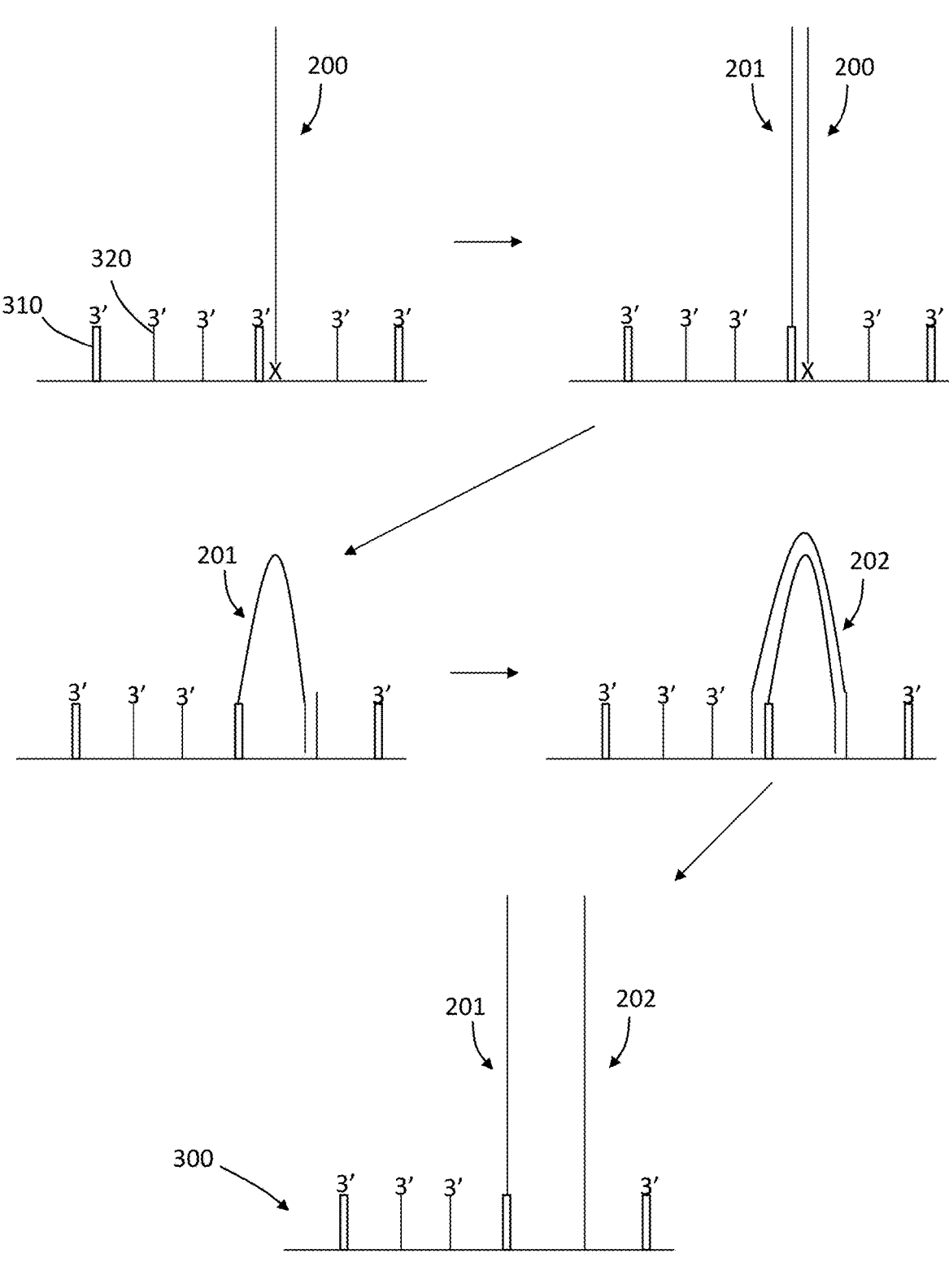
FIG. 3 is a schematic drawing illustrating an embodiment of a process for cluster amplification employing an embodiment of a template polynucleotide (which may be the template polynucleotide depicted in FIG. 2) according to various aspects of the disclosure presented herein.

Referring now to FIG. 3, a schematic illustration of a process for cluster amplification of a template polynucleotide 200 from a library to a solid surface 300 to prepare for sequencing is shown. In the first panel, the template polynucleotide 200 having a blocked 3' end is hybridized to a first extension primer 310 attached to the solid surface 300. For example, universal extension primer sequence 140 depicted in FIG. 1 of the adapter portion may hybridize to the first extension primer 310.

The first extension primer 310 comprises a free 3' end, and thus nucleotides may be added to the 3' end using the template polynucleotide 200 as a template to produce a copy template strand 201 (see second panel) attached to the solid surface 300 in the presence of a suitable polymerase. The template strand 200 may be removed and the copy strand 201 may hybridize with a second extension primer 320 attached to the solid surface 300 (see third panel). For example, universal extension primer sequence 130 depicted in FIG. 1 of the adapter portion may hybridize to the second extension primer 320.

The second extension primer 320 comprises a free 3' end, and thus nucleotides may be added to the 3' end using the copy template polynucleotide 201 as a template to produce an amplified template strand 202 (see fourth panel) attached to the solid surface 300 in the presence of a suitable polymerase. Additional rounds of amplification may be performed to produce a cluster of copy template strands 201 and amplified template strands 202.

For purposes of illustration, the fifth panel of FIG. 3 depicts the copy 201 and amplified 202 template strands in linear form.

Figure 4:
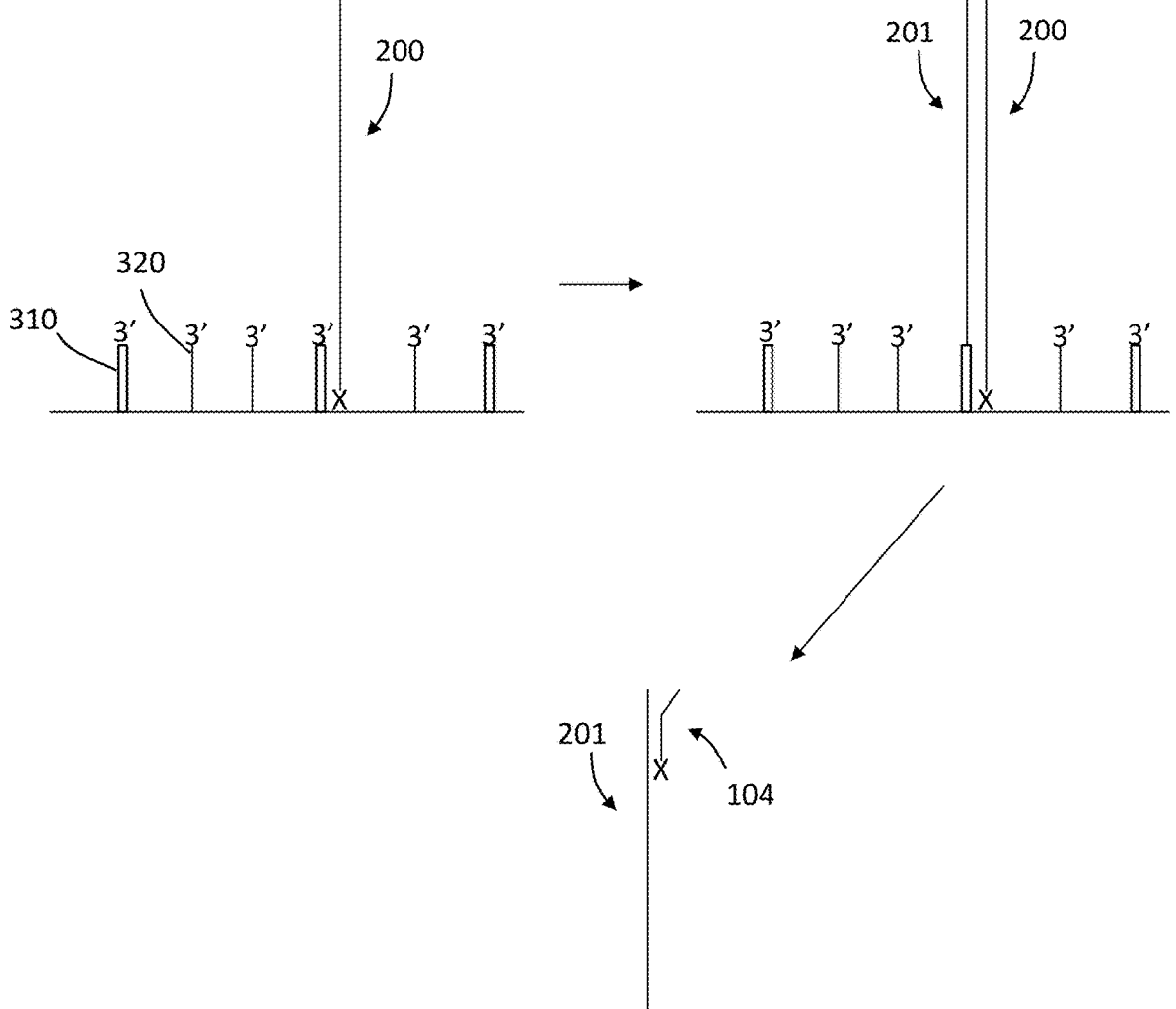
FIG. 4 is a schematic drawing illustrating an embodiment of how 3' end blocking may mitigate index hopping.

Referring now to FIG. 4, a schematic drawing illustrating how blocking of 3' ends may mitigate index hopping is shown. The first two panels of FIG. 4 are the same as the first two panels of FIG. 3. As shown in the third panel of FIG. 4, a residual unincorporated (not attached to a target polynucleotide) adapter 104, or a strand thereof, may hybridize to an adapter portion of the copy template strand 201 (for example, the hybridization may occur at the double stranded region of the adapter and the adapter portion of the template polynucleotide). The adapter 104 may be from a library different than the library from which the copy template strand 201 is derived. Accordingly, the adapter 104 may have an index tag sequence that is different than the index tag sequence associated with the copy template strand 201. Because the 3' end of the adapter is blocked (indicated by the "X"), the adapter 104 cannot serve as an effective primer to extend and copy the copy template strand 201. However, if extension were permitted (and the 3' end of the unincorporated adapter 104 were not blocked), a copy would be produced in which an incorrect index tag (index tag from adapter 104 from a second library) would be associated with a target polynucleotide from another library (target polynucleotide of template polynucleotide 201 from a first library). In a subsequent round of amplification, an incorrectly indexed polynucleotide could be attached to the surface 300.

Figure 5:
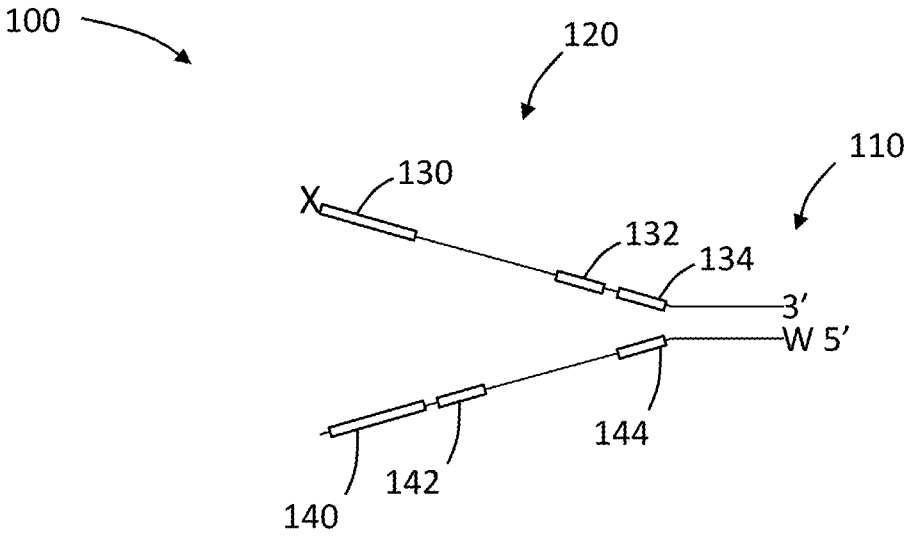
FIGS. 5, 6, 7, and 8 are schematic drawings of multiple embodiments of an adapter according to various aspects of the disclosure presented herein.

Referring now to FIG. 5, a schematic drawing is shown of an adapter 100 that may be used in accordance with various embodiments described herein. The depicted adapter 100 comprises a double-stranded region 110 and a non-complementary single-stranded region 120. The double-stranded region 110 may be attached to a double-stranded target polynucleotide. In the depicted embodiment, the 5' end of the strand in the double-stranded region 110 includes an optional 5' phosphate (indicated by "W"), which aids in both ligation of the adapter 100 to a double-stranded target polynucleotide and digestion by an exonuclease having 5' to 3' exonuclease activity that is biased for double stranded DNA that includes a terminal 5' phosphate. Optionally, the free 5' end of the strand of the single stranded portion 120 is modified to protect the end from exonuclease activity (indicated by "X"), for instance, the free 5' end of the strand of the single stranded portion 120 does not include a 5' phosphate. If the adapter 100 is not attached to a double stranded target fragment, the unincorporated adapter may be degraded by one or more exonuclease having 5' to 3' exonuclease activity that is biased for double stranded DNA. The strand having 140, 142, and 144 is selectively degraded, leaving the other strand and adapter-target-adapter molecules intact. The optional modification at the free 5' end of the strand of the single stranded portion 120 can aid in reducing residual activity the 5' to 3' exonuclease may have for single stranded DNA. If the adapter 100 is part of an incomplete product, e.g., one adapter 100 is attached to a double stranded target molecule, the incomplete product can be degraded by one or more exonuclease having 3' to 5' exonuclease activity that is biased for double stranded DNA having a blunt or recessed 3' terminus. The strand having 130, 132, and 134 is selectively degraded, leaving the other strand and adapter-target-adapter molecules intact.

Figure 6:
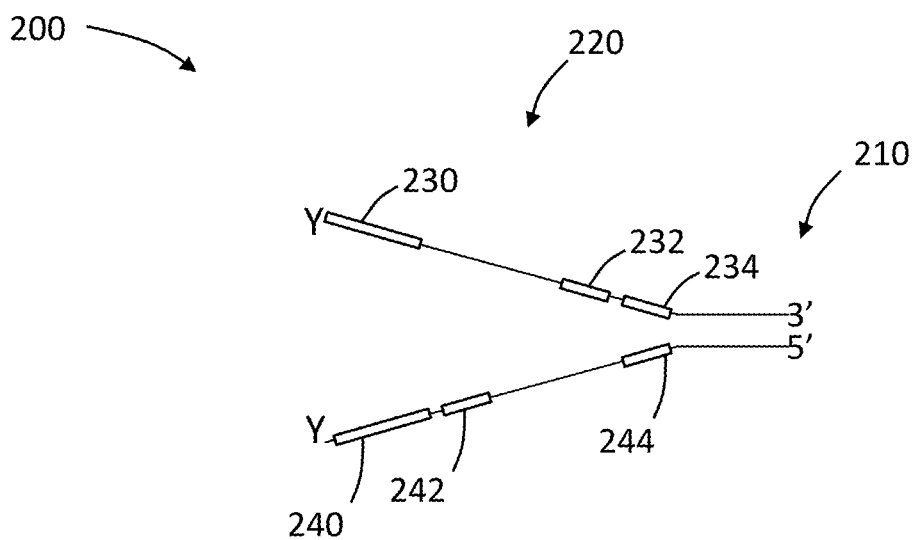

Referring now to FIG. 6, a schematic drawing is shown of an adapter 200 that may be used in accordance with various embodiments described herein. In the depicted embodiment the free ends of each strand of the single stranded portion 220 are modified (indicated by "Y") to protect the ends from exonuclease activity. If the adapter 100 is not attached to a double stranded target fragment, the unincorporated adapter may be digested by one or more exonuclease having both 5' to 3' exonuclease activity and 3' to 5' exonuclease activity. The protection of the two free ends of each strand of the single stranded portion 220 prevents the exonuclease from using desired adapter-target-adapter molecules as a substrate. If the adapter 200 is part of an incomplete product, e.g., one adapter 200 is attached to a double stranded target molecule, the incomplete product can be degraded by one or more exonuclease having 3' to 5' exonuclease activity that is biased for double stranded DNA having a blunt or recessed 3' terminus. The protection of the two free ends of each strand of the single stranded portion 220 prevents the exonuclease from using desired adapter-target-adapter molecules as a substrate.

Figure 7:
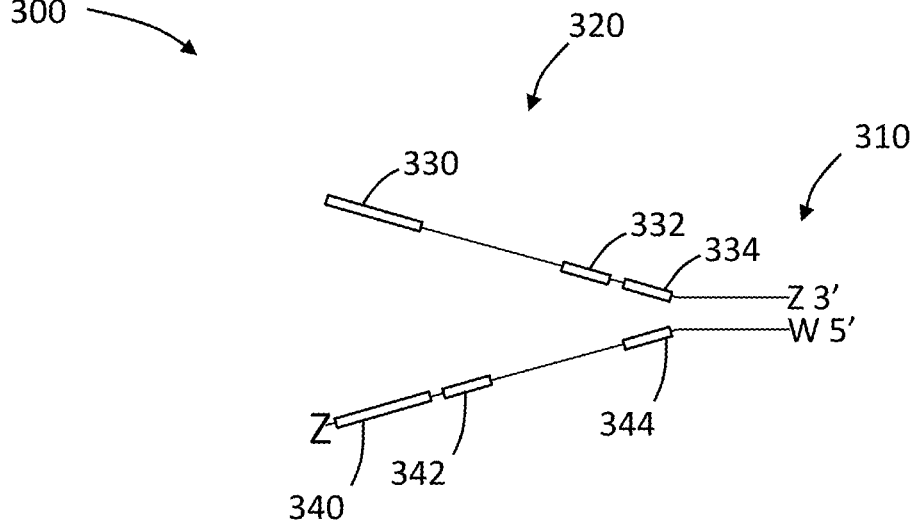

Referring now to FIG. 7, a schematic drawing is shown of an adapter 300 that may be used in accordance with various embodiments described herein. In the depicted embodiment, the 5' end of the strand in the double-stranded region 310 includes an optional 5' phosphate (indicated by "W"), which aids in both ligation of the adapter 300 to a double-stranded target polynucleotide and digestion by an exonuclease having 5' to 3' exonuclease activity that is biased for double stranded DNA that includes a terminal 5' phosphate. The double stranded region 310 may be attached to a double-stranded target polynucleotide if the 3' ends are not blocked. In the depicted embodiment, each strand of the adapter 300 comprises a blocked 3' end, indicated by the "Z." If the adapter 300 is not attached to a double stranded target fragment, the unincorporated adapter may be digested by one or more exonuclease having both 5' to 3' exonuclease activity and 3' to 5' exonuclease activity. Any remaining adapter sequences not degraded by the exonuclease cannot act as a primer for extension of any polynucleotide sequence during subsequent amplification and/or sequencing reactions.

Figure 8:
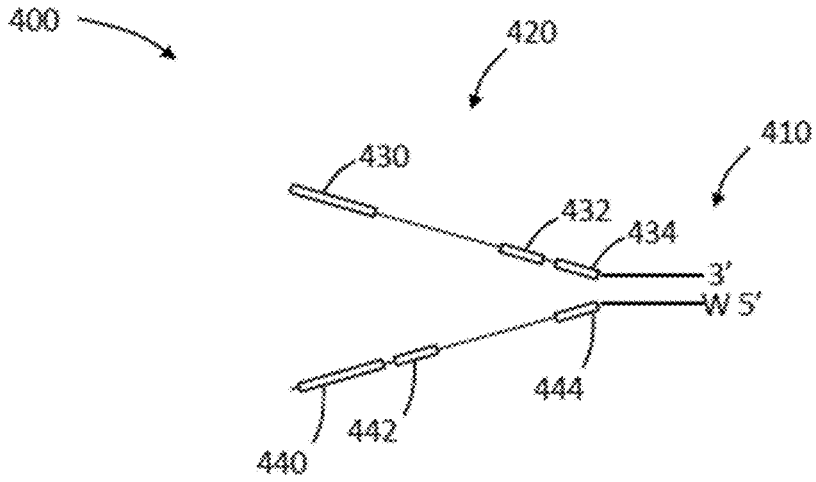

Referring now to FIG. 8, a schematic drawing is shown of an adapter 400 that may be used in accordance with various embodiments described herein. In the depicted embodiment, the 5' end of the strand in the double-stranded region 410 includes an optional 5' phosphate (indicated by "W"), which aids in both ligation of the adapter 400 to a double-stranded target polynucleotide. The double stranded region 410 may be attached to a double-stranded target polynucleotide. In those embodiments where one adapter is attached to a double-stranded target molecule (an incomplete product), the incomplete product may be digested by one or more exonuclease having 3' to 5' exonuclease activity that is biased for double stranded DNA having a blunt or recessed 3' terminus.

In FIGS. 5, 6, 7, and 8, one depicted strand of the adapter 100 or 200 or 300 or 400 comprises a universal extension primer binding site 130 or 230 or 330 or 430 (e.g., P5), a tag sequence 132 or 232 or 332 or 432 (e.g., i5), and a sequencing primer binding site 134 or 234 or 334 or 434 (e.g., SBS3). The other depicted strand of the adapter 100 or 200 or 300 or 400 comprises a universal extension primer binding site 140 or 240 or 340 or 440 (e.g., P7'), a tag sequence 142 or 242 or 342 or 442 (e.g., i7), and a sequencing primer binding site 144 or 244 or 344 or 444 (e.g., SBS12').

In FIGS. 5, 6, 7, and 8, the universal extension primer binding sites 130 or 230 or 330 or 430 (e.g., P5), 140 or 240 or 340 or 440 (e.g., P7') may hybridize to extension primer oligonucleotides attached to a solid surface for purposes of amplification or sequencing (if the adapter 100 or 200 or 300 or 400 was attached to a target polynucleotide).

Universal extension primer binding site 140 or 240 or 340 or 440 (e.g., P7'), or a portion thereof, may also hybridize to a sequencing primer for sequencing index tag sequence 142 or 242 or 342 or 442 (e.g., i7). Alternatively the strand may comprise a further sequencing primer sequence (not shown).

In FIGS. 5, 6, 7, and 8, sequencing primer binding site 134 or 234 or 334 or 434 (e.g., SBS3) may hybridize to a sequencing primer to allow sequencing of index tag sequence 132 or 232 or 332 or 432 (e.g., i5). Tag sequence 142 or 242 or 342 or 442 and tag sequence 132 or 232 or 332 or 432 may be the same or different.

In FIGS. 5, 6, 7, and 8, sequencing primer binding site 144 or 244 or 344 or 444 (e.g., SBS12') may hybridize to a sequencing primer to allow sequencing of a target polynucleotide sequence (if attached to the adapter 100 or 200 or 300 or 400).

In FIGS. 5, 6, 7, and 8, sequencing primer binding sites 134 or 234 or 334 or 434 (e.g., SBS3), 144 or 244 or 344 or 444 (e.g., SBS12') may hybridize to, for example, PCR primers if the adapters are attached to a target in a multi-step process as described above.

It will be understood that a suitable adapter for use in various embodiments described herein may have more or less sequence features, or other sequence features, than those described regarding FIG. 5, FIG. 6, FIG. 7, and FIG. 8.

Figure 9:
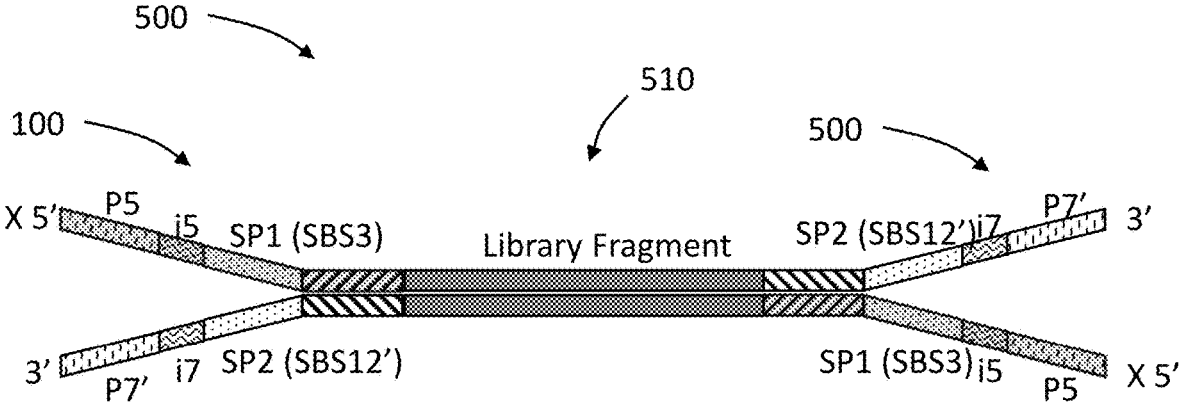
FIG. 9, 10, 11, 12A and 12B are schematic drawings of multiple embodiments of a template polynucleotide having an adapter-target-adapter molecule (which may include an adapter, or a portion thereof) generally as shown in FIG. 5, 6, 7, or 8, respectively, according to various aspects of the disclosure presented herein.

Referring now to FIG. 9, a schematic drawing of an adapter-target-adapter 500 of a library having an adapter 100—template 510—adapter 100 sequence is shown. The adapter-target-adapter 510 is double stranded and attached to a double stranded portion of the adapters 100. The 5' ends of the single stranded portions of the adapters are modified to protect from exonuclease digestion (indicated by "X"). Because the adapters 100 are ligated to both ends of the double stranded target fragment 510, no double stranded sequences are available on an adapter-target-adapter molecule for an exonuclease, thus the resulting adapter-target-adapter 400 is resistant to digestion by exonuclease.

Figure 10:
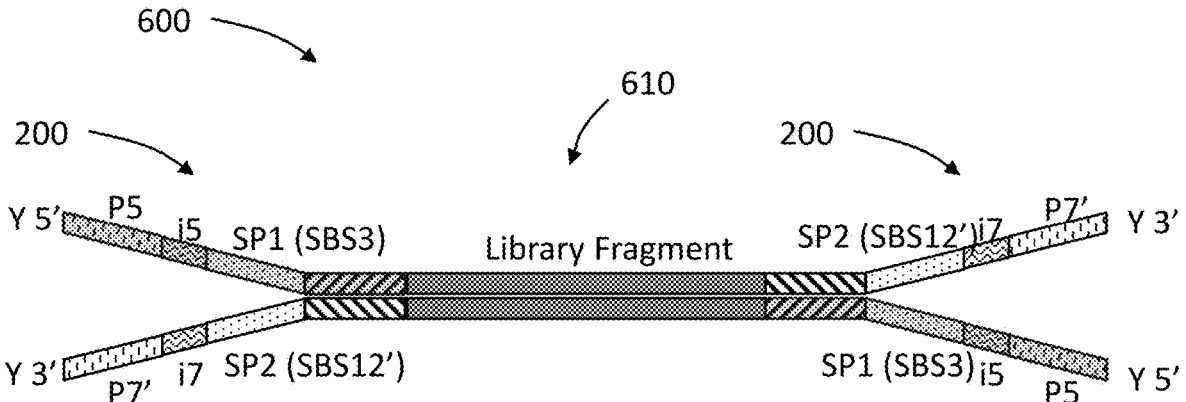

Referring now to FIG. 10, a schematic drawing of an adapter-target-adapter 600 of a library having an adapter 200—template 610—adapter 200 sequence is shown. The adapter-target-adapter 610 is double stranded and attached to a double stranded portion of the adapters 200. The ends of the single stranded portions of the adapters are modified to protect from exonuclease digestion (indicated by "Y"). Because the adapters 200 are ligated to both ends of the double stranded target fragment 610, no unblocked single stranded sequences are available on an adapter-target-adapter molecule for an exonuclease, thus the resulting adapter-target-adapter 600 is resistant to digestion by exonuclease.

Figure 11:
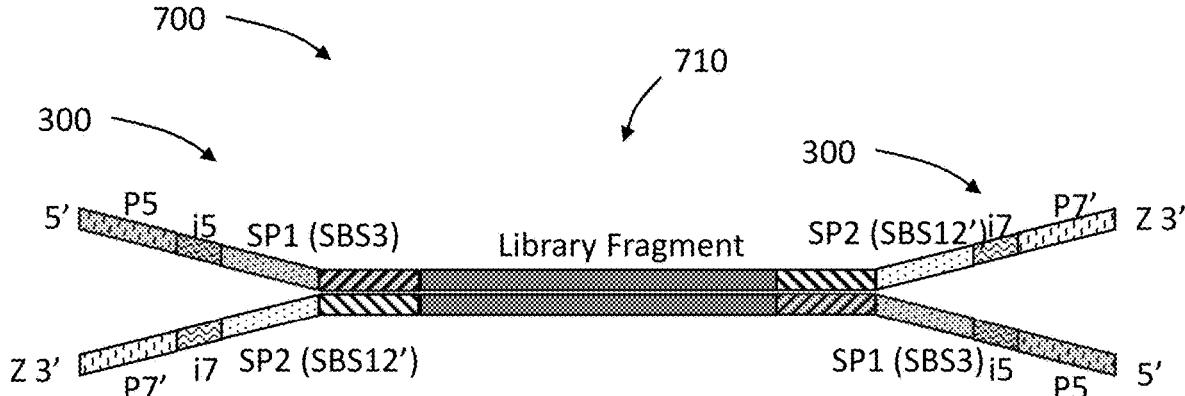
Figure 11:
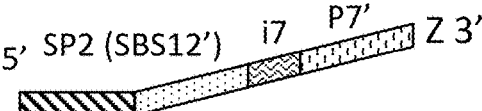

Referring now to FIG. 11, a schematic drawing of an adapter-target-adapter 700 of a library having an adapter 300—template 710—adapter 300 sequence is shown. The adapter-target-adapter 710 is double stranded and attached to a double stranded portion of the adapters 300. The ends of the single stranded regions of the adapters are modified to prevent them from acting as primers for extension of any polynucleotide in a flowcell. FIG. 7 further shows a schematic drawing of an adapter that was not completed degraded by exonuclease. A single strand of an adapter 300 is shown. This single stranded adapter cannot act as a primer for extension of any polynucleotide in a flowcell.

Figure 12A:
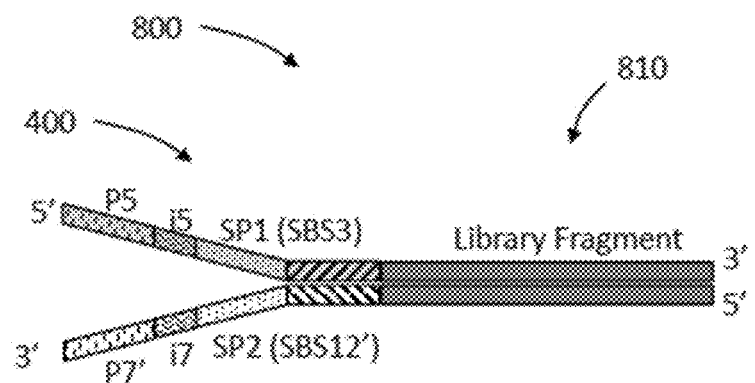
Figure 12B:
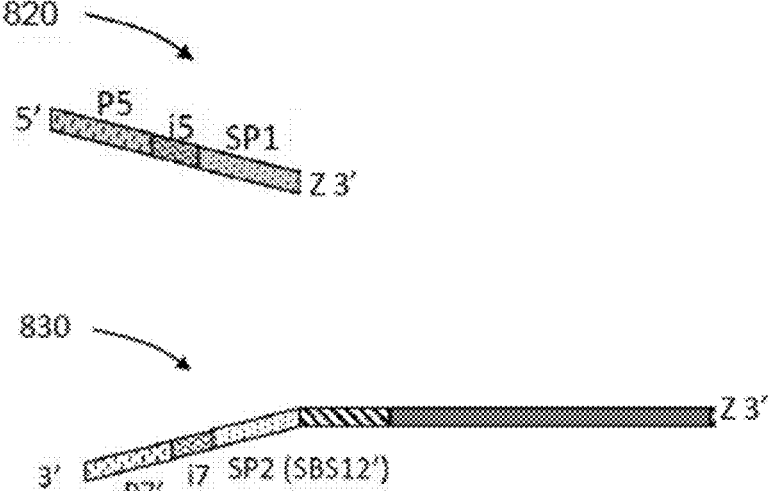

Referring now to FIG. 12A, a schematic drawing of an incomplete product of adapter-target 800 of a library having an adapter 400—template 810 sequence is shown. The adapter-target 800 is double stranded and attached to a double stranded portion of the adapter 400. FIG. 12B further shows a schematic drawing of one result of digestion of an incomplete product 800 with an exonuclease having 3' to 5' exonuclease activity that is biased for double stranded DNA having a blunt or recessed 3' terminus. Digestion of one strand of the double stranded portion of an adapter-target 800 from 3' to 5' may result in two single stranded molecules. One strand is a single strand adapter-target 830. The other adaptor strand 820 corresponds to one of the single stranded regions of an adapter 400. In this embodiment, the polynucleotides present in library pool are 3' blocked, as indicated by the "Z," after exposure to an exonuclease having 3' to 5' exonuclease activity that is biased for double stranded DNA having a blunt or recessed 3' terminus. These 3' blocked single stranded adapter-target 830 and adapter strand 820 cannot act as a primer for extension of any polynucleotide in a flowcell.

Figure 13:
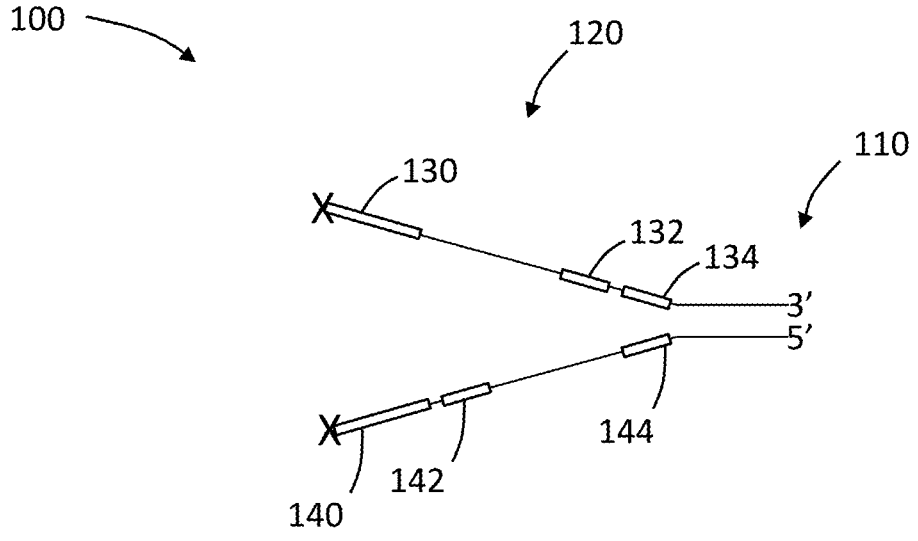
FIG. 13 is a schematic drawing of an embodiment of an adapter according to various aspects of the disclosure presented herein.

Referring now to FIG. 13 a schematic drawing is shown of an adapter 100 that may be used in accordance with various embodiments described herein. The depicted adapter 100 comprises a double-stranded region 110 and a non-complementary single-stranded region 120. The double-stranded region 110 may be attached to a double-stranded target polynucleotide. In the depicted embodiment, the free ends of each strand of the single stranded portion 120 are modified (indicated by "X") to protect the ends from exonuclease activity. In contrast the 3' end of one strand and the 5' end of the other strand that form the double stranded portion 110 are susceptible to exonuclease degradation. If the adapter 100 is not attached to a double stranded target fragment, the unincorporated adapter may be digested by one or more exonuclease having 5' and 3' exonuclease activity. Because the exonuclease will begin digestion from the double stranded portion 110, the exonuclease preferably has activity for double-stranded DNA without nicking.

One depicted strand of the adapter 100 comprises a universal extension primer sequence 130, an index tag sequence 132, and a sequencing primer sequence 134. The other depicted strand of the adapter 100 comprises a universal extension primer sequence 140, an index tag sequence 142, and a sequencing primer sequence 144.

The universal extension primer sequences 130, 140 may hybridize to extension primer oligonucleotides attached to a solid surface for purposes of amplification or sequencing (if the adapter 100 was attached to a target polynucleotide). Universal extension primer sequence 140, or a portion thereof, may also hybridize to a sequencing primer for sequencing index tag sequence 142. Alternatively the strand may comprise a further sequencing primer sequence (not shown).

Sequencing primer sequence 134 may hybridize to a sequencing primer to allow sequencing of index tag sequence 132. Index tag sequence 142 and index tag sequence 132 may be the same or different.

Sequencing primer sequence 144 may hybridize to a sequencing primer to allow sequencing of a target polynucleotide sequence (if attached to the adapter 100).

Sequencing primer sequences 134, 144 may hybridize to, for example, PCR primers if the adapters are attached to a target in a multi-step process as described above.

It will be understood that a suitable adapter for used in various embodiments described herein may have more or less sequence features, or other sequence features, than those described regarding FIG. 13.

Figure 14:
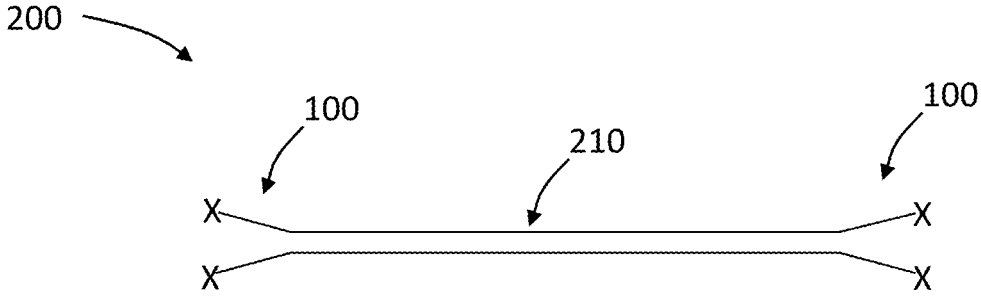
FIG. 14 is a schematic drawing of an embodiment of a template polynucleotide having an adapter-target-adapter sequence (which may include an adapter generally as shown in FIG. 13) according to various aspects of the disclosure presented herein.

Referring now to FIG. 14, a schematic drawing of a template polynucleotide 200 of a library having an adapter 100—template 210—adapter 100 sequence is shown. The template polynucleotide 210 is double stranded and attached to a double stranded portion of the adapters 100. The ends of the single stranded portions of the adapters are modified to protect from exonuclease digestion (indicated by "X"). Because the adapters 100 are ligated to both ends of the double stranded target fragment 210, the resulting template polynucleotide 200 is resistant to digestion by exonuclease.

Figure 15:
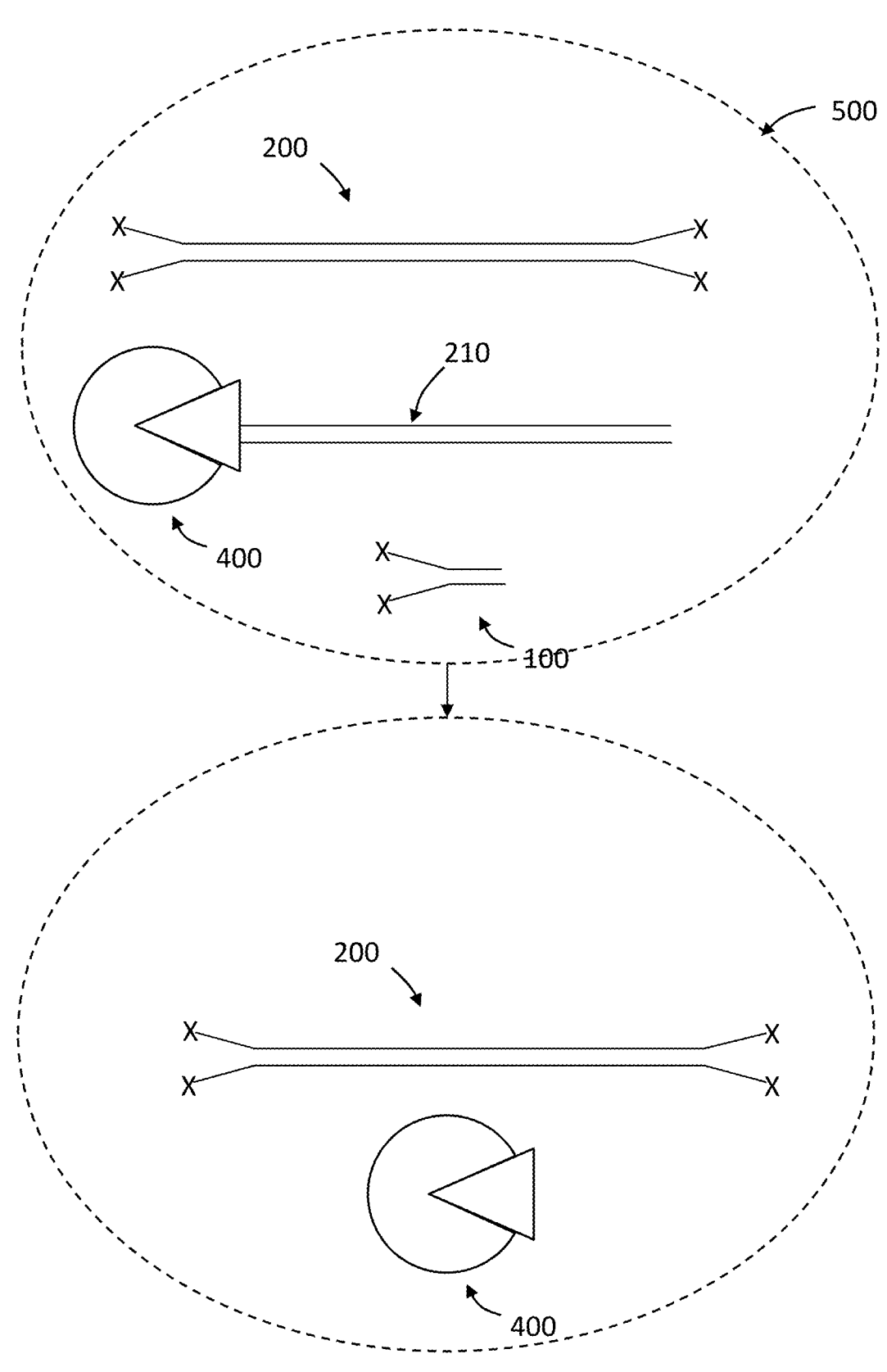
FIG. 15 is a schematic drawing illustrating results of incubating reaction products and reagents of an adapter-target ligation with an exonuclease.

Referring now to FIG. 15, a schematic drawing illustrating results of incubating reaction products and reagents of an adapter-target ligation with an exonuclease 400 is shown.

Following ligation of an adapter 100 to a target fragment 210, some remaining unincorporated adapter 100, target fragment 210, and template polynucleotide 200 results. If the resulting solution or composition 500 is incubated with an exonuclease 400 having 5' exonuclease activity and having 5' exonuclease activity, the unincorporated adapter 100 and target fragment 210 will be digested by the exonuclease 400 (see bottom of FIG. 3). Following exonuclease treatment, the resulting solution may be cleaned up and the template polynucleotide 200may be immobilized on a solid surface for sequencing.

Figure 16:
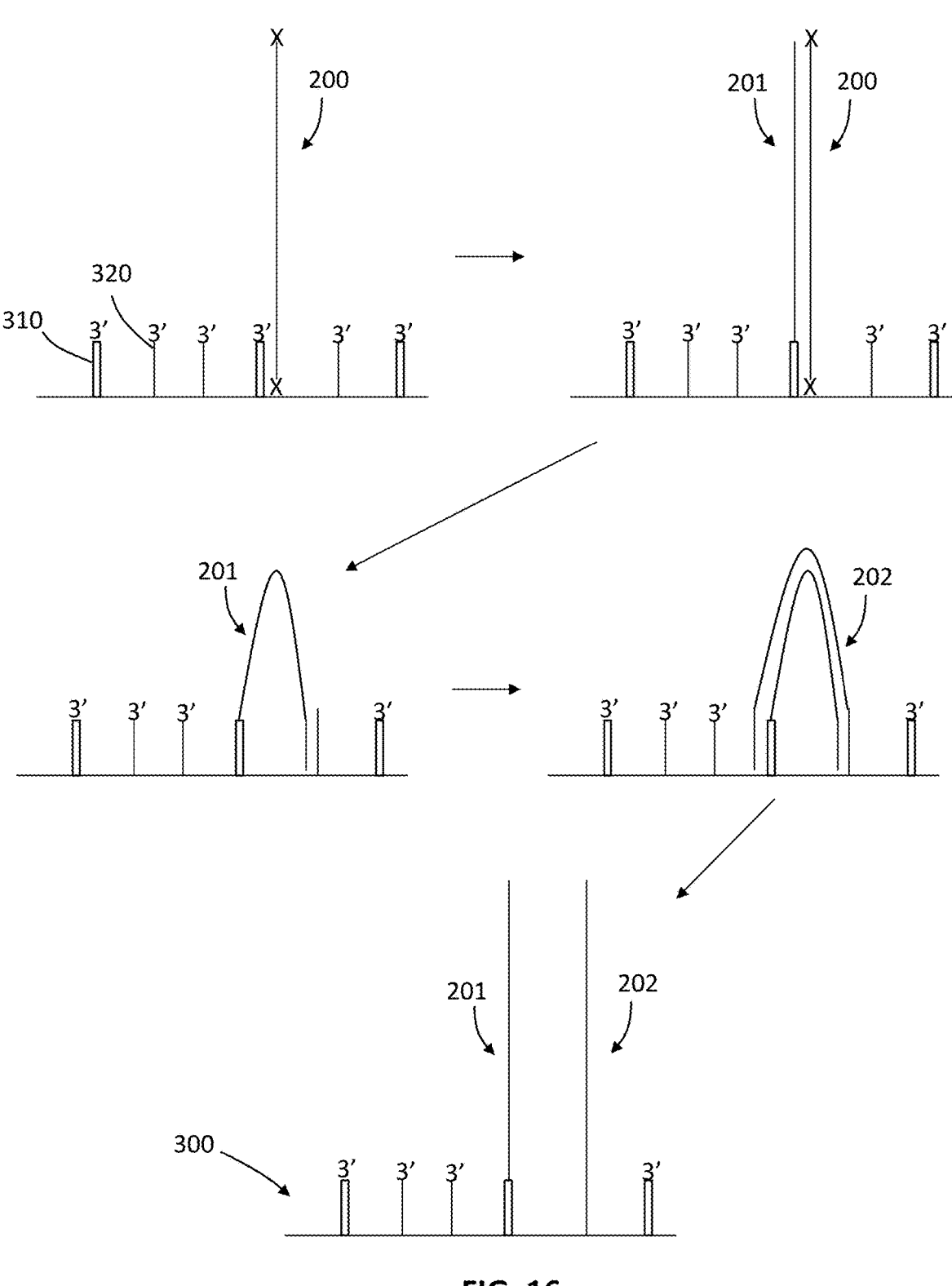
FIG. 16 is a schematic drawing illustrating an embodiment of a process for cluster amplification employing an embodiment of a template polynucleotide (which may be the template polynucleotide depicted in FIG. 14) according to various aspects of the disclosure presented herein.

Referring now to FIG. 16, a schematic illustration of a process for cluster amplification of a template polynucleotide 200 from a library to a solid surface 300 to prepare for sequencing is shown. In the first panel, the template polynucleotide 200 having modified ends (for nuclease protection) is hybridized to a first extension primer 310 attached to the solid surface 300. For example, universal extension primer sequence 140 depicted in FIG. 1 of the adapter portion may hybridize to the first extension primer 310.

The first extension primer 310 comprises a free 3' end, and thus nucleotides may be added to the 3' end using the template polynucleotide 200 as a template to produce a copy template strand 201 (see second panel) attached to the solid surface 300 in the presence of a suitable polymerase. The template strand 200 may be removed and the copy strand 201 may hybridize with a second extension primer 320 attached to the solid surface 300 (see third panel). For example, universal extension primer sequence 130 depicted in FIG. 1 of the adapter portion may hybridize to the second extension primer 320.

The second extension primer 320 comprises a free 3' end, and thus nucleotides may be added to the 3' end using the copy template polynucleotide 201 as a template to produce an amplified template strand 202 (see fourth panel) attached to the solid surface 300 in the presence of a suitable polymerase. Additional rounds of amplification may be performed to produce a cluster of copy template strands 201 and amplified template strands 202.

For purposes of illustration, the fifth panel of FIG. 15 depicts the copy 201 and amplified 202 template strands in linear form.

Figure 17:
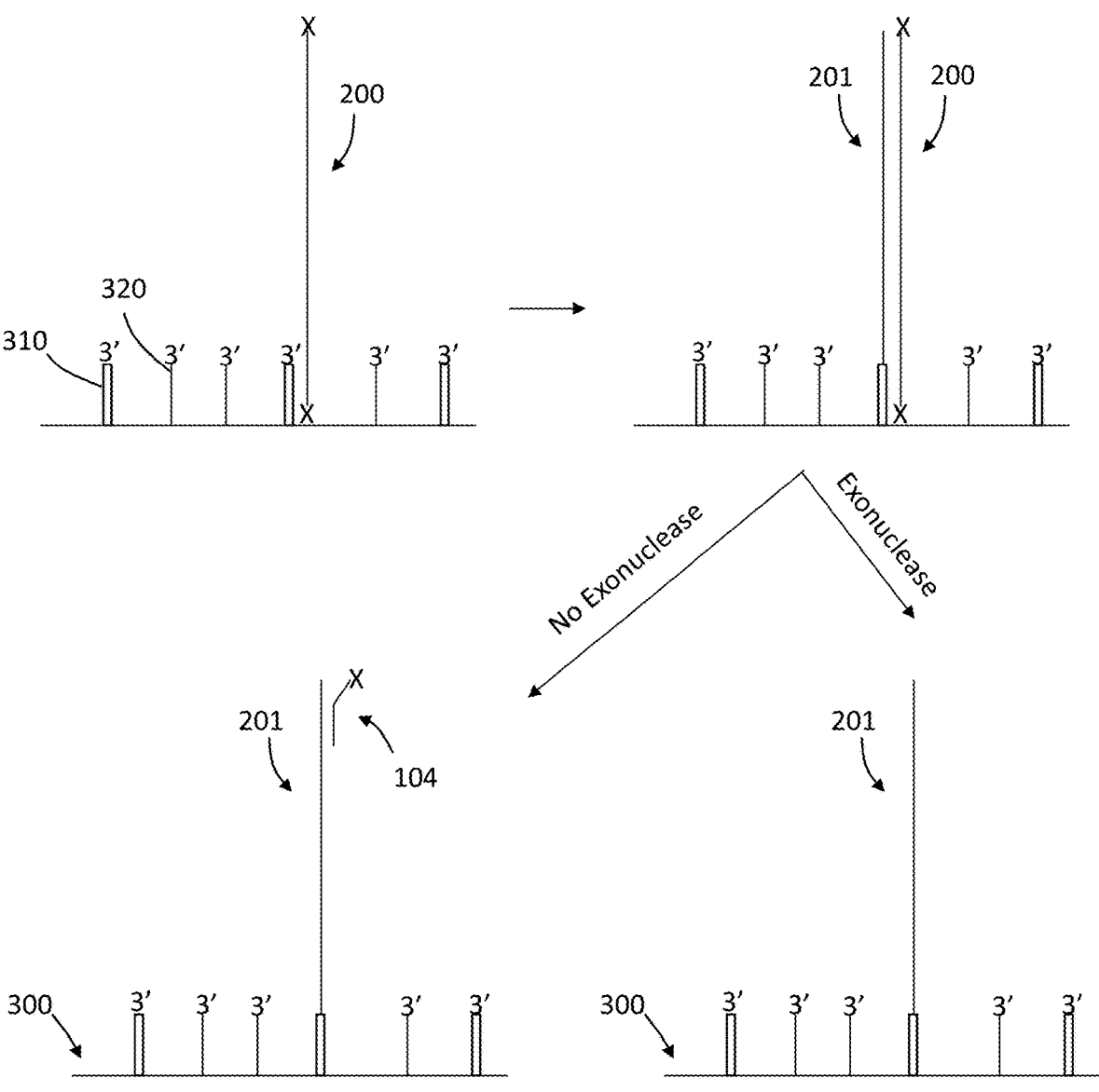
FIG. 17 is a schematic drawing illustrating an embodiment of how exonuclease treatment may mitigate index hopping in accordance with various embodiments described herein.

Referring now to FIG. 17, a schematic drawing illustrating how exonuclease treatment to remove unincorporated adapters may mitigate index hopping is shown. The first two panels of FIG. 17 are the same as the first two panels of FIG. 164. As shown in the bottom left panel of FIG. 17, a residual unincorporated (not attached to a target polynucleotide) adapter, or a strand 104 thereof, may hybridize to an adapter portion of the copy template strand 201 (for example, the hybridization may occur at the double stranded region of the adapter and the adapter portion of the template polynucleotide).

The adapter strand 104 may be from a library different than the library from which the copy template strand 201 is derived. Accordingly, the adapter strand 104 may have an index tag sequence that is different than the index tag sequence associated with the copy template strand 201. The adapter strand 104 may serve as an effective primer to extend and copy the copy template strand 201. An amplified strand would be produced in which an incorrect index tag (index tag from adapter strand 104 from a second library) would be associated with a target polynucleotide from another library (target polynucleotide of template polynucleotide 201 from a first library). In a subsequent round of amplification, an incorrectly indexed polynucleotide could be attached to the surface 300. However, and as illustrated in the bottom right panel of FIG. 5, if unincorporated adapters are digested by exonuclease treatment, the adapter strand is not available to serve as an extension primer and index hoping is mitigated.

Figure 18:
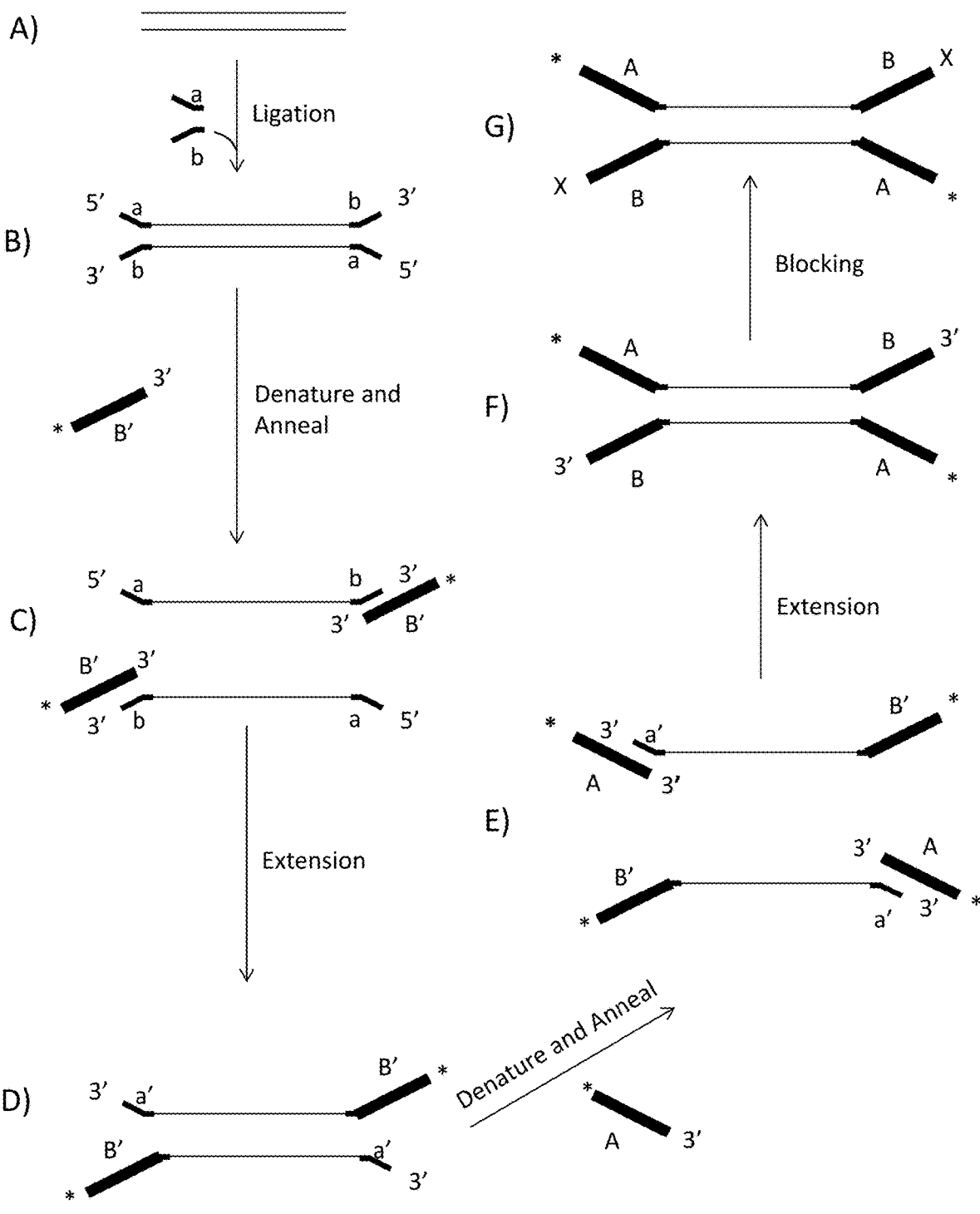
FIG. 18 is a schematic drawing illustrating an embodiment of a process for producing 5' modified and 3' blocked template polynucleotides.

Referring now to FIG. 18, a schematic drawing illustrating an embodiment of a process for producing 5' modified and 3' blocked template polynucleotides for immobilizing on a solid surface for sequencing is shown. In FIG. 18A, a double stranded target polynucleotide fragment is shown. Initial portions of adapters may be attached to the ends of the target by ligation (see FIG. 18B) or tagmentation. The portions of the adapters (ab) comprise a double stranded portion attached to the double stranded target and single stranded portions extending away from the target to the 5' and 3' ends. A 5' modified primer (B') is configured to hybridize to a single stranded portion of the adapter (b) in proximity to the 3' end (FIG. 18C). A polymerase may be used to extend the primer B' using the portions of the adapter and the target as a template to produce a complement of the portions of the adapter (a') and the target (FIG. 18D, strands from FIG. 18C removed for purposes of convenience and clarity). A 5' modified primer (A) is configured to hybridize to a single stranded portion of the complement of the adapter portion (a') in proximity to the 3' end (FIG. 18E). A polymerase may be used to extend the primer A using the portions of the complement of the adapters and target as a template to produce portions of the adapter (b) and the target (FIG. 18F, strands from FIG. 18E removed for purposes of convenience and clarity).

If the adapter portion that is added by, for example, ligation or tagmentation includes the library specific index tag sequence at a location between the sequence for hybridization of the primers (A, B') and the target (when the portion of the adapter is attached to the target), amplification (FIGS. 18C-F) with primers (A, B') may be performed on pooled target fragments from different libraries, provided that each fragment from each library includes a portion of an adapter having a library specific index tag sequence in a similar location and each portion of the adapter from each library has a sequence (or complement) to which primers (A, B') may hybridize. Otherwise, each library should be amplified separately.

The resulting 5' protected template (amplified adapter-target-amplified adapter) may be subjected to 3' blocking to produce a 5' and 3' protected template polynucleotide (FIG. 18G) for immobilizing on a solid surface for sequencing. 3' blocking may affect any polynucleotide present in solution with the 5' protected template, including any other amplification fragments or residual polynucleotides (not shown). Accordingly, if adaptor portions (ab) are amplified with primers (A, B), the amplified adapters that are not attached to the template (not shown) should also be 3' blocked.

Exonuclease treatment may optionally be applied to the resulting mixture. Remaining unblocked or unprotected polynucleotides may be degraded prior to immobilizing the template polynucleotides on a solid surface.

Figure 19:
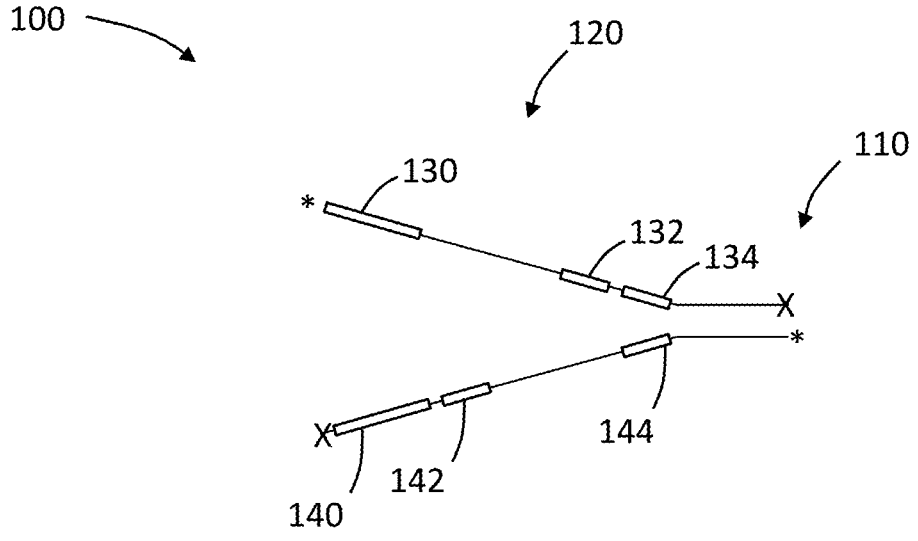
FIG. 19 is a schematic drawing of an embodiment of an adapter according to various aspects of the disclosure presented herein.

Referring now to FIG. 19 a schematic drawing is shown of an adapter (amplified adapter) 100 that may be used or result during amplification of the libraries in preparation for sequencing. The depicted adapter 100 comprises a double-stranded region 110 and a non-complementary single-stranded region 120. The 5' ends are modified (indicated by the "*") to prevent degradation by an exonuclease, and the 3' ends are blocked (indicated by the "X"). One depicted strand of the adapter 100 comprises a universal extension primer sequence 130, an index tag sequence 132, and a sequencing primer sequence 134. The other depicted strand of the adapter 100 comprises a universal extension primer sequence 140, an index tag sequence 142, and a sequencing primer sequence 144.

The universal extension primer sequences 130, 140 may hybridize to extension primer oligonucleotides attached to a solid surface for purposes of amplification or sequencing (if the adapter 100 were attached to a target polynucleotide). Universal extension primer sequence 140, or a portion thereof, may also hybridize to a sequencing primer for sequencing index tag sequence 142. Alternatively, the strand may comprise a further sequencing primer sequence (not shown).

Sequencing primer sequence 134 may hybridize to a sequencing primer to allow sequencing of index tag sequence 132. Index tag sequence 142 and index tag sequence 132 may be the same or different.

Sequencing primer sequence 144 may hybridize to a sequencing primer to allow sequencing of a target polynucleotide sequence (if attached to the adapter 100).

Sequencing primer sequences 134, 144 may hybridize to, for example, PCR primers if the adapters are attached to a target in a multi-step process as described above.

It will be understood that a suitable adapter for used in various embodiments described herein may have more or less sequence features, or other sequence features, than those described regarding FIG. 19.

Figure 20:
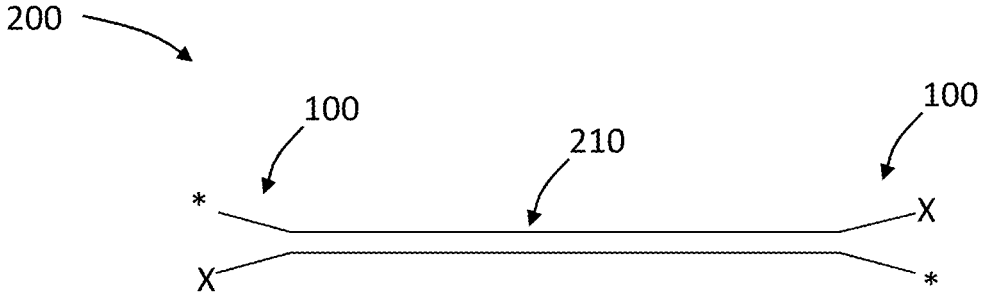
FIG. 20 is a schematic drawing of an embodiment of a template polynucleotide having an adapter-target-adapter sequence (which may include an adapter generally as shown in FIG. 2) according to various aspects of the disclosure presented herein.

Referring now to FIG. 20, a schematic drawing of a template polynucleotide 200 of a library having an adapter 100—template 210—adapter 100 sequence is shown. The template polynucleotide 210 is double stranded and attached to a double stranded portion of the first 100 and second 101 adapters. The 3' ends of the template polynucleotide 200 are blocked and the 5' ends are modified, e.g., as described above.

Figure 21:
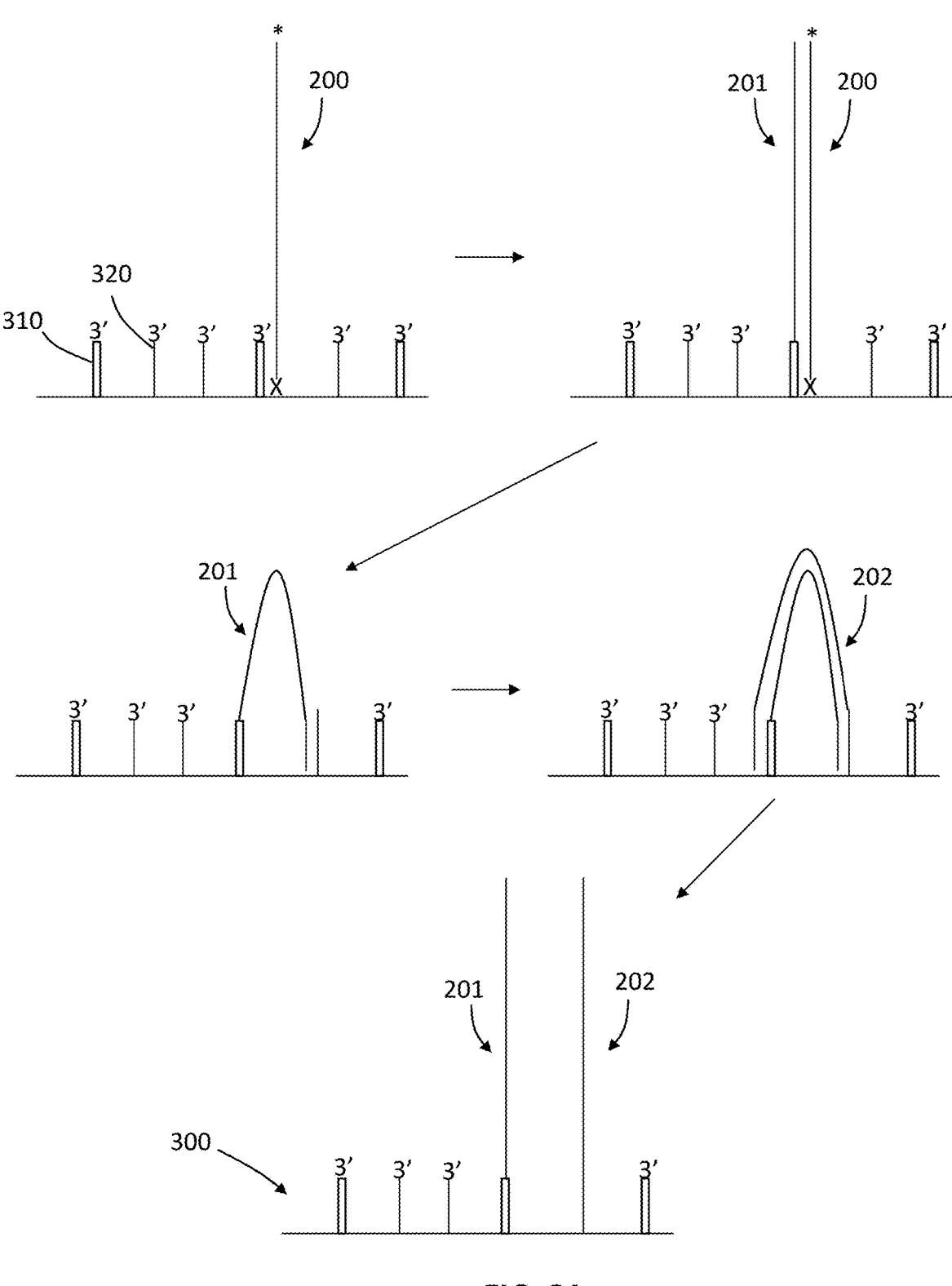
FIG. 21 is a schematic drawing illustrating an embodiment of a process for cluster amplification employing an embodiment of a template polynucleotide (which may be the template polynucleotide depicted in FIG. 20) according to various aspects of the disclosure presented herein.

Referring now to FIG. 21, a schematic illustration of a process for cluster amplification of a template polynucleotide 200 from a library to a solid surface 300 to prepare for sequencing is shown. In the first panel, the template polynucleotide 200 having a modified 5' end and a blocked 3' end is hybridized to a first extension primer 310 attached to the solid surface 300. For example, universal extension primer sequence 140 depicted in FIG. 2 of the adapter portion may hybridize to the first extension primer 310.

The first extension primer 310 comprises a free 3' end, and thus nucleotides may be added to the 3' end using the template polynucleotide 200 as a template to produce a copy template strand 201 (see second panel) attached to the solid surface 300 in the presence of a suitable polymerase. The template strand 200 may be removed and the copy strand 201 may hybridize with a second extension primer 320 attached to the solid surface 300 (see third panel). For example, universal extension primer sequence 130 depicted in FIG. 19 of the adapter portion may hybridize to the second extension primer 320.

The second extension primer 320 comprises a free 3' end, and thus nucleotides may be added to the 3' end using the copy template polynucleotide 201 as a template to produce an amplified template strand 202 (see fourth panel) attached to the solid surface 300 in the presence of a suitable polymerase. Additional rounds of amplification may be performed to produce a cluster of copy template strands 201 and amplified template strands 202.

For purposes of illustration, the fifth panel of FIG. 21 depicts the copy 201 and amplified 202 template strands in linear form.

Figure 22:
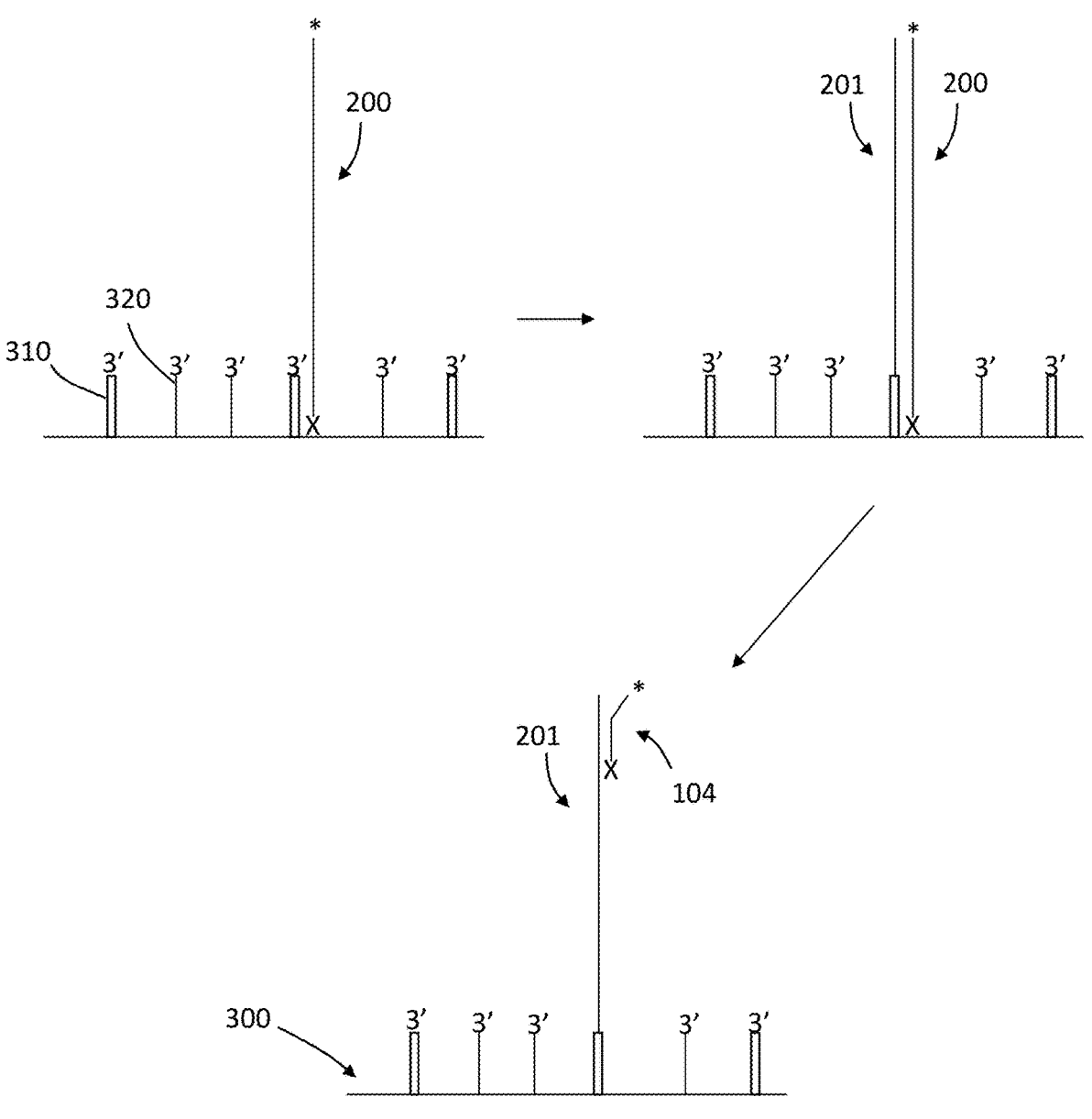
FIG. 22 is a schematic drawing illustrating an embodiment of how 3' end blocking may mitigate index hopping.

Referring now to FIG. 22, a schematic drawing illustrating how blocking of 3' ends (to prevent extension from the blocked 3' end) may mitigate index hopping is shown. The first two panels of FIG. 22 are the same as the first two panels of FIG. 21. As shown in the third panel of FIG. 22, a residual unincorporated (not attached to a target polynucleotide) adapter strand 104 may hybridize to an adapter portion of the copy template strand 201 (for example, the hybridization may occur at the double stranded region of the adapter and the adapter portion of the template polynucleotide). The adapter strand 104 may be from a library different than the library from which the copy template strand 201 is derived. Accordingly, the adapter 104 may have an index tag sequence that is different than the index tag sequence associated with the copy template strand 201. Because the 3' end of the adapter is blocked (indicated by the "X"), the adapter 104 cannot serve as an effective primer to extend and copy the copy template strand 201. However, if extension were permitted (and the 3' end of the unincorporated adapter 104 were not blocked), a copy would be produced in which an incorrect index tag (index tag from adapter 104 from a second library) would be associated with a target polynucleotide from another library (target polynucleotide of template polynucleotide 201 from a first library). In a subsequent round of amplification, an incorrectly indexed polynucleotide could be attached to the surface 300.

Figure 23:
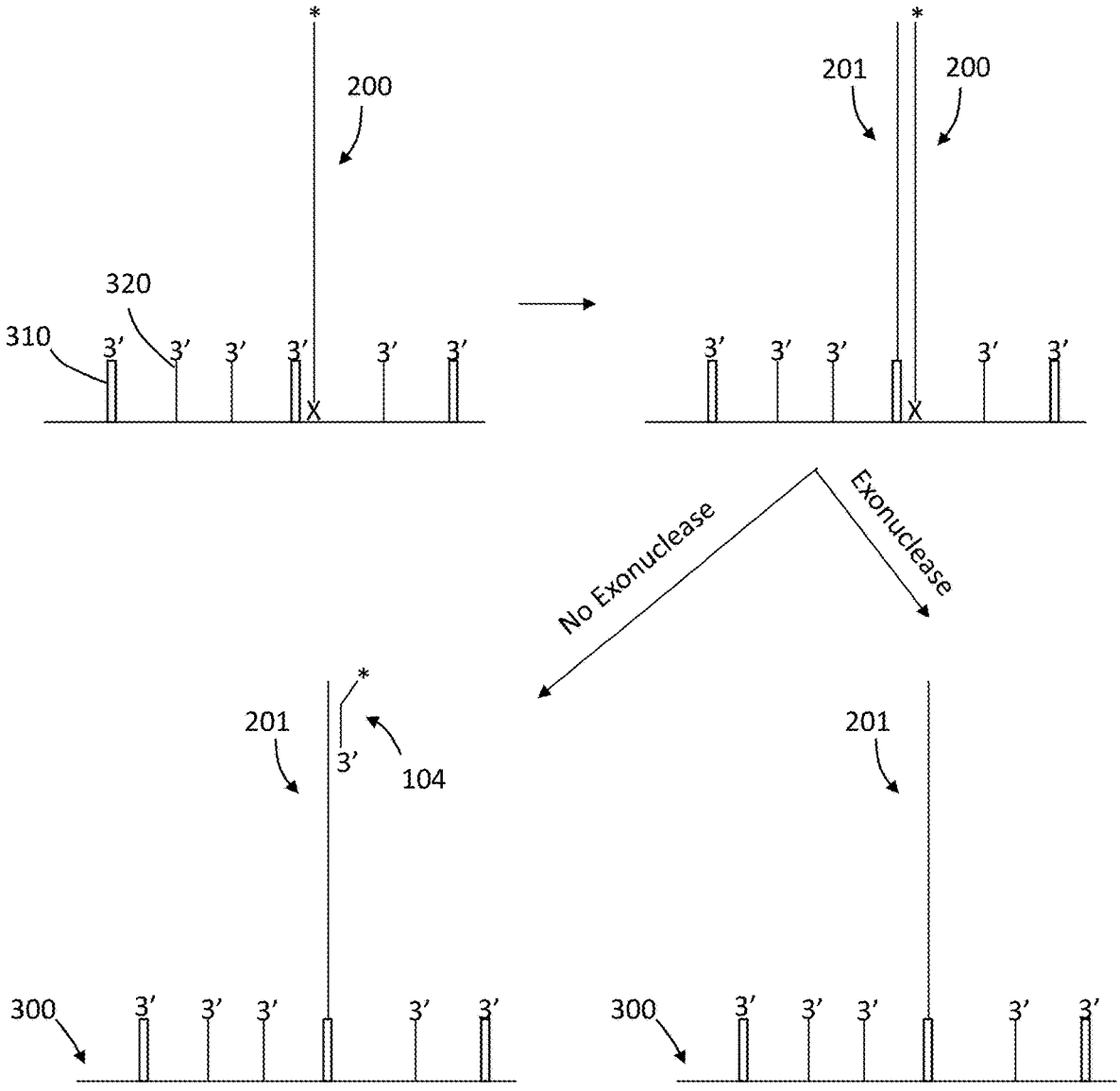
FIG. 23 is a schematic drawing illustrating an embodiment of how exonuclease treatment may mitigate index hopping in accordance with various embodiments described herein.

Referring now to FIG. 23, a schematic drawing illustrating how exonuclease treatment to remove unblocked and unincorporated adapters or adapter strands may mitigate index hopping is shown. The first two panels of FIG. 23 are the same as the first two panels of FIG. 21. As shown in the bottom left panel of FIG. 23, an adapter strand 104 that may result from amplification (e.g., as described regarding FIGS. 18B-F) that was not blocked during a 3' blocking step (e.g., as described regarding FIG. 18G) may hybridize to an adapter portion of the copy template strand 201 (for example, the hybridization may occur at the double stranded region of the adapter and the adapter portion of the template polynucleotide). The adapter strand 104 may be from a library different than the library from which the copy template strand 201 is derived. Accordingly, the adapter strand 104 may have an index tag sequence that is different than the index tag sequence associated with the copy template strand 201. The adapter strand 104 may serve as an effective primer to extend and copy the copy template strand 201. An amplified strand would be produced in which an incorrect index tag (index tag from adapter strand 104 from a second library) would be associated with a target polynucleotide from another library (target polynucleotide of template polynucleotide 201 from a first library). In a subsequent round of amplification, an incorrectly indexed polynucleotide could be attached to the surface 300. However and as illustrated in the bottom right panel of FIG. 23, if the unblocked adapters or adapter strands that may result are digested by exonuclease treatment, the adapter strand is not available to serve as an extension primer and index hoping is mitigated.

Figure 24A:
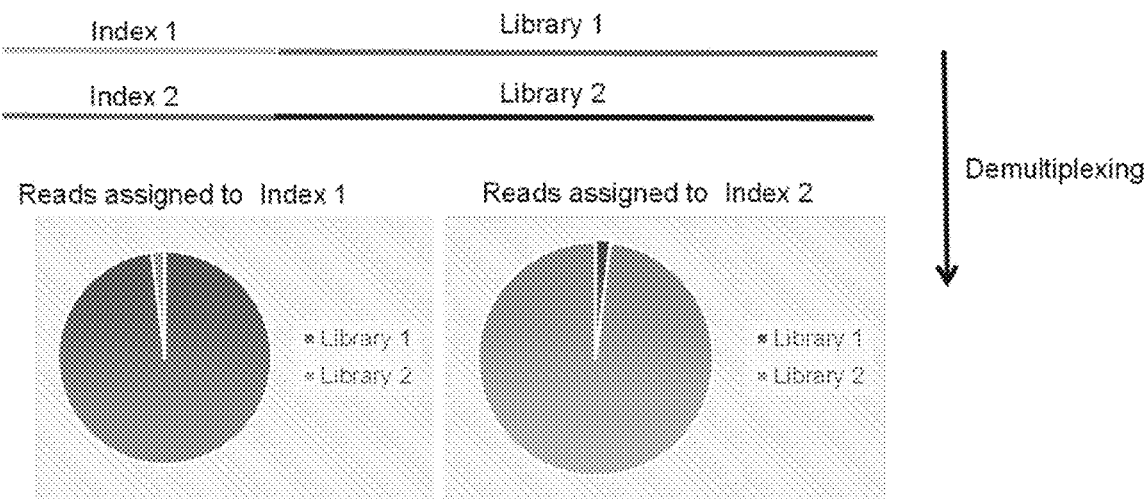
FIGS. 24A and 24B illustrate the nature of the index hopping phenomenon.
Figure 24B:
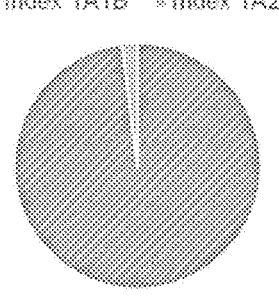

Referring now to FIGS. 24A and 24B, the nature of the index hopping phenomenon is illustrated. FIG. 24A shows how reads from a given sample are incorrectly demultiplexed and mixed with a different sample following demultiplexing. FIG. 24B demonstrates index hopping in a dual index system, where it leads to unexpected combinations of index tag sequences.

Figures 25A, 25B:
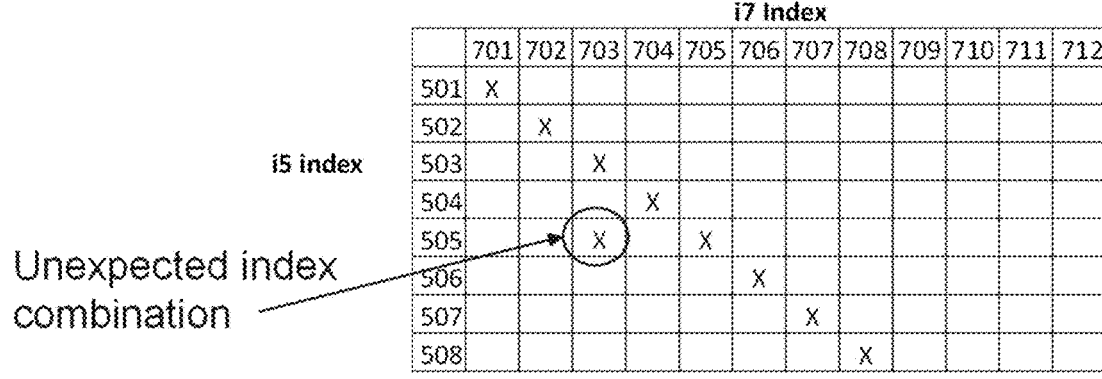
FIGS. 25A and 25B illustrate the general approach to measuring the rate of index hopping in a given system.

Referring now to FIGS. 25A and 25B, the general approach to measuring the rate of index hopping in a given system is illustrated. FIG. 25A shows an exemplary layout of a dual adapter plate, wherein each individual well of a 96-well plate contains a unique pair of index tag sequences (12 different P7 indices combined with 8 different P5 indices). FIG. 25B shows an experimental setup aimed at measuring the rate of index hopping, wherein 8 unique dual index tag combinations are used (i.e. no P5 index is expected to pair up with more than one P7 index and vice versa). Unexpected combinations of index tags (e.g., D505-D703) are then easily identified as instances of index hopping.

Figure 26A:
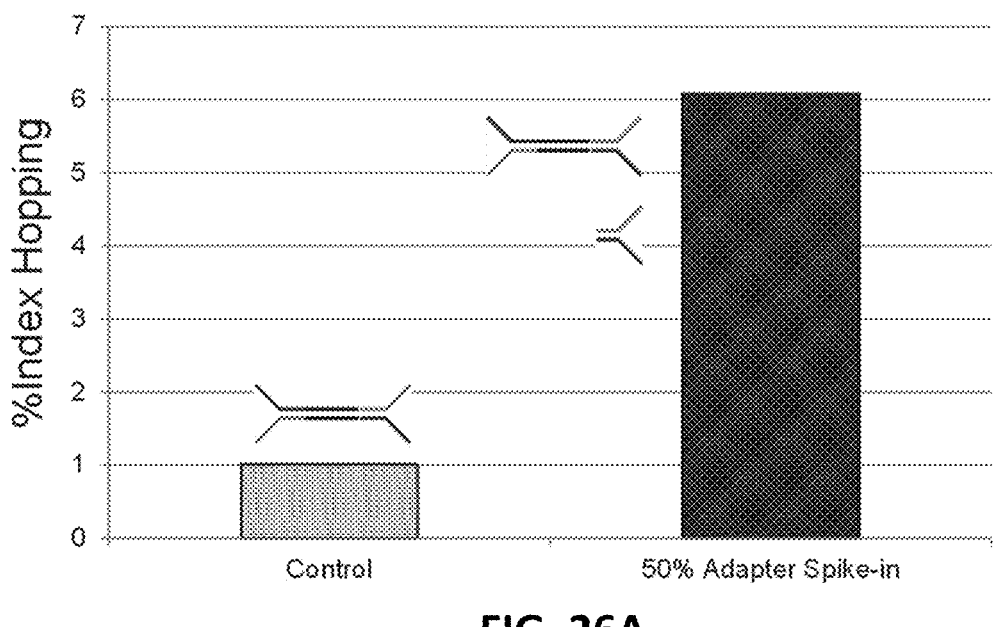
FIGS. 26A and 26B illustrate the effect of unligated adapters on the rate of index hopping.
Figure 26B:
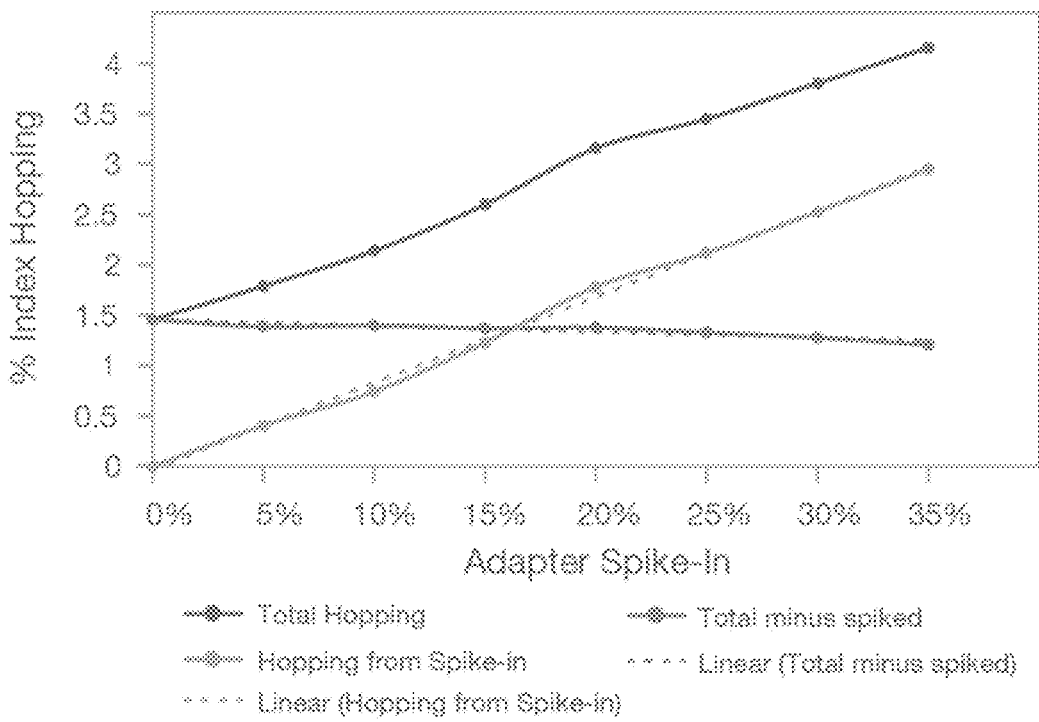

Referring now to FIGS. 26A and 26B, the effect of unligated adapters on the rate of index hopping is illustrated. FIG. 26A shows a 6-fold increase in index hopping associated with a 50% spike-in of free adapters. FIG. 26B shows an approximately linear effect of the free forked adapter on the rate of index hopping within the range tested. The inventors also observed a more pronounced effect of free single-stranded P7 adapters on the rate of index hopping compared to free single-stranded P5 adapters (data not shown).

Figure 28A:
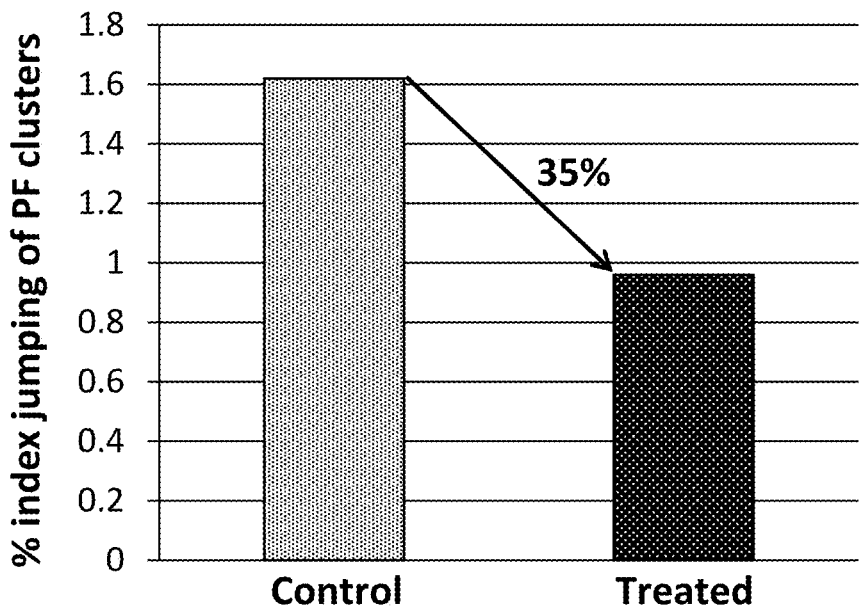
FIGS. 28A and 28B illustrate the effect of exonuclease treatment according to the present invention on the rates of index hopping in Illumina TruSeq® PCR-Free library preparation work flow, with (FIG. 28B) and without (FIG. 28A) 3' blocking.
Figure 28B:
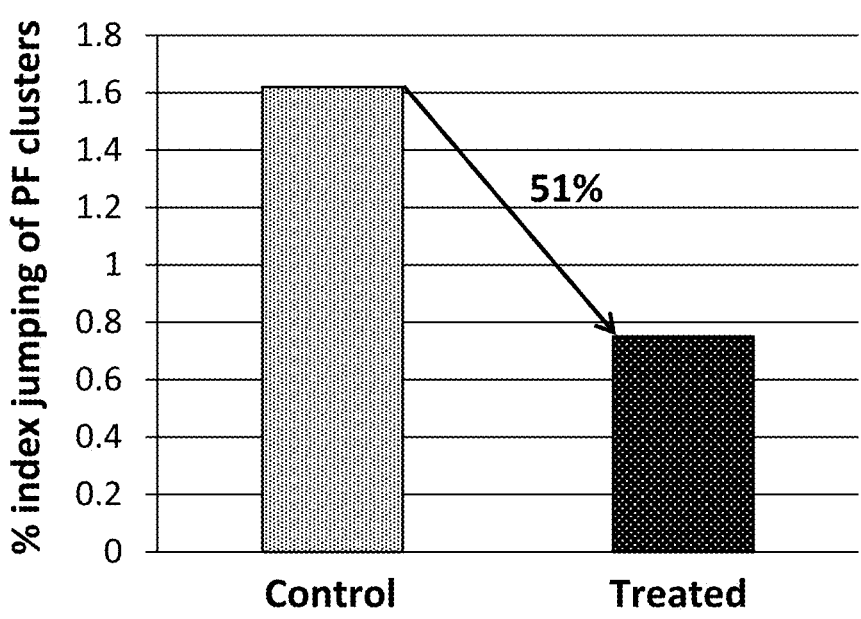

Referring now to FIGS. 28A and 28B, the effect of exonuclease treatment on the rates of index hopping in Illumina TruSeq® PCR-Free library preparation workflow, alone and in combination with 3' blocking, respectively, is illustrated. Significant decreases in index hopping were observed in both instances, though a stronger reduction was observed with the combined exonuclease and 3' blocking treatment.

Examples

The present disclosure is illustrated by the following examples. It is to be understood that the particular examples, materials, amounts, and procedures are to be interpreted broadly in accordance with the scope and spirit of the disclosure as set forth herein.

Example 1: Sample Protocol for 3' Blocking of Indexed Libraries

This protocol explains how to perform a 3' blocking treatment on DNA libraries to reduce index hopping. This method is designed to be performed on DNA library pools prior to the denaturation step and subsequent cluster generation using the Illumina HiSeq® 4000 and similar sequencing platforms utilizing patterned flow cells and ExAmp based clustering (e.g., HiSeq® X and NovaSeq®).

Index hopping has been seen to occur where incorrect index sequences are assigned to the insert sequence resulting in sample misassignment. Performing this treatment on DNA sample pools before running on HiSeq® 4000 should reduce the index hopping levels by some level which cannot at this stage be predicted consistently.

Treatment workflow may be considered to involve four steps: (i) produce DNA sample pool; (ii) perform treatment; (iii) cleanup sample and quantify; and (iv) cluster and sequence sample pool.

Consumables/Equipment: Consumables and equipment may be supplied by a sequencing user or manufacture. User supplied consumables may include a DNA library sample pool—30 µl at concentration to be used for denaturation during clustering. The user may also supply freshly prepared 80% ethanol (EtOH).

Table 1 below illustrates some consumables and equipment that may be used.

TABLE 1

Consumables and Equipment

| Consumable/Equipment | Supplier |
|---|---|
| Ethanol 200 proof (absolute) for molecular biology | Sigma-Aldrich, Cat #E7023 |
| Magnetic stand-96 | Life Technologies, Cat #AM10027 |
| Vortexer | General lab supplier |
| 96-well thermal cycler (with heated lid) | General lab supplier |

A sequencing manufacturer may supply IHT (Index Hopping Treatment Mix); RSB (Resuspension Buffer), and SPB (Sample Purification Beads).

The IHT mix may include a sequencing premix (Tris buffer, sodium chloride, sucrose, magnesium sulfate, EDTA and Tween 20), a ddNTP mix, Poll9 DNA polymerase, and TDT terminal transferase.

The RSB may include a Tris buffer, pH 8.5.

The SPB may include AgenCourt® AMPure® XP beads (Beckman Coulter, Cat #A63880). The SPB should be vortexed before each use. The SPB should be vortexed frequently to make sure that beads are evenly distributed. The SPB should be aspirated and dispensed slowly due to the viscosity of the solution.

Some of the consumables should be stored and prepared as indicated in Table 2 below.

TABLE 2

Storage and preparation of consumables

| Item | Storage | Instructions |
|---|---|---|
| BMX | −25° C. to −15° C. | Thaw at room temperature, and then place on ice. Return to storage after use. |
| RSB | 2° C. to 8° C. | Let stand for 30 min to bring to room temperature. Return to storage after use. |
| SPB | 2° C. to 8° C. | Let stand for 30 min to bring to room temperature. |

The following blocking program may be saved on the thermal cycler: (i) choose the preheat lid option and set to 100° C.; (ii) 38° C. for 20 mins; (iii) 60° C. for 20 mins; and (iv) hold at 4° C.

The samples may be treated as follows: (i) centrifuge IHT at 600×g for 5 seconds; (ii) add 30 µl of DNA library sample pool to PCR tube; (iii) add 30 µl IHT mix to each sample in each PCR tube and then mix thoroughly by pipetting up and down; and (iv) incubate by placing on the thermal cycler and running the IHT program. Each tube contains 60 µl.

The treated pooled sample may be cleaned up as follows: (1) vortex SPB until well-dispersed; (2) add 60 µl SPB to each sample treatment tube and mix thoroughly by pipetting up and down; (3) incubate at room temperature for 5 minutes; (4) place on a magnetic stand and wait until the liquid is clear (2-5 minutes); (5) remove and discard all supernatant from each tube; (6) wash 2 times as follows: (a) add 200 µl freshly prepared 80% EtOH to each tube, (b) incubate on the magnetic stand for 30 seconds, and (c) remove and discard all supernatant from each tube; (7) use a 20 µl pipette to remove residual EtOH from each tube; (8) air-dry on the magnetic stand for 5 minutes; (9) add 22.5 µl RSB to each tube; (10) remove from the magnetic stand and then mix thoroughly by pipetting up and down; (11) incubate at room temperature for 2 minutes; (12) place on a magnetic stand and wait until the liquid is clear (2-5 minutes); (13) transfer 20 µl supernatant to a new tube; (14) quantify libraries if required and proceed onto standard clustering for the HiSeq® 4000 platform starting with NaOH denaturation step; and (15) store at −25° C. to −15° C. if not clustering immediately.

Example 2: Reduction of Index Hopping by 3' Blocking of Indexed Libraries

The treatment protocol set forth above in Example 1 was applied in combination with the following materials, equipment and methods for clustering and sequencing on Illumina platform.

Experimental conditions: (1) Human 450 bp NA12878 (Coriell Institute) TrueSeq® Nano and PCR-Free libraries loaded at 600 pM and 300 pM respectively; (2) HiSeq® X instrument and Illumina SBS chemistry according to manufacturer's instructions; (3) 550 nm ILS v3 flow cell; (4) ExAmp amplification as previously described; and (5) adapter spike-in: 5% free forked adapter from the Illumina dual adapter plate (DAP) spiked into template library prior to denaturation, neutralization, ExAmp mix addition and clustering.

Figure 27:
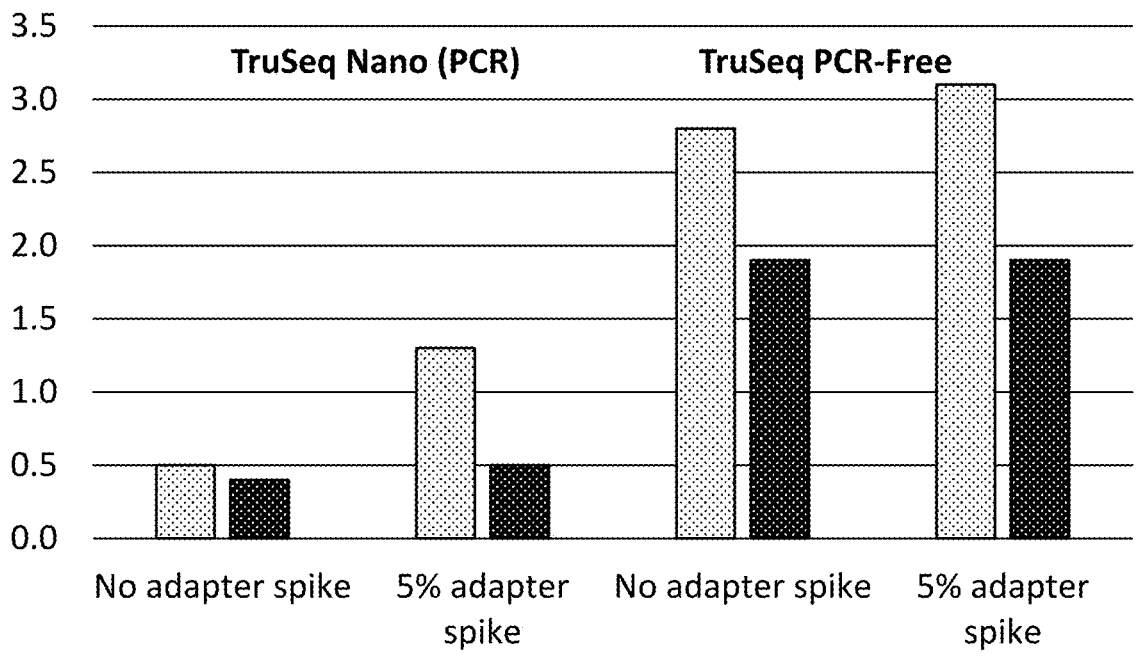

Results of this experiment are summarized in Table 3 below and FIG. 27.

TABLE 3

| Reduction of index hopping by 3' blocking | | | |
|---|---|---|---|
| | Adapter | Index hopping (% of PF clusters) | |
| Library | spike | No 3' blocking | 3' blocking |
| TruSeq ® Nano (PCR) | None | 0.5% | 0.4% |
| | Spike | 1.3% | 0.5% |
| TruSeq ® PCR-Free | None | 2.8% | 1.9% |
| | Spike | 3.1% | 1.9% |

As illustrated above, index hopping was decreased with 3' blocking in samples having entire adapters ligated ("PCR-Free") and samples having at least a portion added through PCR, specifically the 5' ends of PCR primers.

Example 3: Sample Protocol for Exonuclease Treatment with Optional 3' Blocking of Indexed Libraries This protocol explains how to perform an exonuclease treatment, either alone or combined with 3' blocking of DNA libraries, to reduce index hopping. This method is designed to be performed on DNA library pools prior to the denaturation step and subsequent cluster generation using the Illumina HiSeq® 4000 and similar sequencing platforms utilizing patterned flow cells and ExAmp based clustering (e.g., HiSeq® X and NovaSeq®).

Index hopping has been seen to occur where incorrect index sequences are assigned to the insert sequence resulting in sample misassignment. Performing this treatment on DNA sample pools before running on HiSeq® 4000 should reduce the index hopping levels by some level which cannot at this stage be predicted consistently.

Treatment workflow may be considered to involve four steps: (i) produce DNA sample pool; (ii) perform treatment; (iii) cleanup sample and quantify; and (iv) cluster and sequence sample pool.

Consumables/Equipment: Consumables and equipment may be supplied by a sequencing user or manufacture. User supplied consumables may include a DNA library sample pool—30 μl at concentration to be used for denaturation during clustering. The user may also supply freshly prepared 80% ethanol (EtOH).

Table 4 below illustrates some consumables and equipment that may be used.

TABLE 4

| Consumables and Equipment | |
|---|---|
| Consumable/Equipment | Supplier |
| Ethanol 200 proof (absolute) for molecular biology | Sigma-Aldrich, Cat #E7023 |
| Magnetic stand-96 | Life Technologies, Cat #AM10027 |
| Vortexer | General lab supplier |
| 96-well thermal cycler (with heated lid) | General lab supplier |

A sequencing manufacturer may supply EMX (Exonuclease Mix), BMX (Blocking Mix), RSB (Resuspension Buffer), and SPB (Sample Purification Beads).

The EMX may include an exonuclease buffer (67 mM Glycine-KOH, 2.5 mM MgCl$_2$, 50 μg/ml BSA) and Lambda Exonuclease (New England Biolabs, Cat #M0262S/L).

The BMX may include a sequencing premix (Tris buffer, sodium chloride, sucrose, magnesium sulfate, EDTA and Tween 20), a ddNTP mix, Poll9 DNA polymerase, and TDT terminal transferase.

The RSB may include a Tris buffer, pH 8.5.

The SPB may include AgenCourt® AMPure® XP beads (Beckman Coulter, Cat #A63880). The SPB should be vortexed before each use. The SPB should be vortexed frequently to make sure that beads are evenly distributed. The SPB should be aspirated and dispensed slowly due to the viscosity of the solution.

Some of the consumables should be stored and prepared as indicated in Table 5 below.

TABLE 5

| Storage and preparation of consumables | | |
|---|---|---|
| Item | Storage | Instructions |
| EMX | −25° C. to −15° C. | Thaw at room temperature, and then place on ice. Return to storage after use. |
| BMX | −25° C. to −15° C. | Thaw at room temperature, and then place on ice. Return to storage after use. |
| RSB | 2° C. to 8° C. | Let stand for 30 min to bring to room temperature. |
| SPB | 2° C. to 8° C. | Let stand for 30 min to bring to room temperature. |

The following EMX program may be saved on the thermal cycler: (i) choose the preheat lid option and set to 100° C.; (ii) 37° C. for 30 mins; (iii) 75° C. for 10 mins; and (iv) hold at 4° C.

The following BMX program may be saved on the thermal cycler: (i) choose the preheat lid option and set to 100° C.; (ii) 38° C. for 20 mins; (iii) 60° C. for 20 mins; and (iv) hold at 4° C.

For the exonuclease only treatment, the samples may be treated as follows: (i) centrifuge EMX at 600×g for 5 seconds; (ii) add 27 μl of DNA library sample pool to PCR tube; (iii) add 5 μl EMX to each sample in each PCR tube and then mix thoroughly by pipetting up and down; (iv) incubate by placing on the thermal cycler and running the EMX program. Each tube contains 32 μl.

For the exonuclease plus 3' blocking treatment, the samples may be treated as follows: (i) centrifuge EMX at 600×g for 5 seconds; (ii) add 27 μl of DNA library sample pool to PCR tube; (iii) add 5 μl EMX to each sample in each PCR tube and then mix thoroughly by pipetting up and down; (iv) incubate by placing on the thermal cycler and running the EMX program; (v) centrifuge BMX at 600×g for 5 seconds; (vi) add 32 μl BMX directly to each exonuclease reaction in each PCR tube and then mix thoroughly by pipetting up and down; and (vii) incubate by placing on the thermal cycler and running the BMX program. Each tube contains 64 μl.

The treated pooled sample may be cleaned up as follows: (1) vortex SPB until well-dispersed; (2) add 60 μl SPB to each sample treatment tube and mix thoroughly by pipetting up and down; (3) incubate at room temperature for 5 minutes; (4) place on a magnetic stand and wait until the liquid is clear (2-5 minutes); (5) remove and discard all supernatant from each tube; (6) wash 2 times as follows: (a) add 200 μl freshly prepared 80% EtOH to each tube, (b) incubate on the magnetic stand for 30 seconds, and (c) remove and discard all supernatant from each tube; (7) use a 20 μl pipette to remove residual EtOH from each tube; (8) air-dry on the magnetic stand for 5 minutes; (9) add 22.5 μl RSB to each tube; (10) remove from the magnetic stand and then mix thoroughly by pipetting up and down; (11) incubate at room temperature for 2 minutes; (12) place on a magnetic stand and wait until the liquid is clear (2-5 minutes); (13) transfer 20 μl supernatant to a new tube; (14) quantify libraries if required and proceed onto standard clustering for the HiSeq® 4000 platform starting with NaOH denaturation step; and (15) store at −25° C. to −15° C. if not clustering immediately.

Example 4: Reduction of Index Hopping by Exonuclease Treatment with 3' Blocking of Indexed Libraries The treatment protocol set forth above in Example 3 was applied in combination with the following materials, equipment and methods for clustering and sequencing on Illumina platform.

Experimental conditions: (1) Human 450 bp NA12878 (Coriell Institute) TrueSeq® PCR-Free library loaded at 300 pM; (2) HiSeq® X instrument and Illumina SBS chemistry according to manufacturer's instructions; (3) 550 nm ILS v3 flow cell; (4) ExAmp amplification as previously described; and (5) 50% adapter spike-in: free forked adapter from the Illumina dual adapter plate (DAP) spiked into template library prior to denaturation, neutralization, ExAmp mix addition and clustering.

Figure 29:
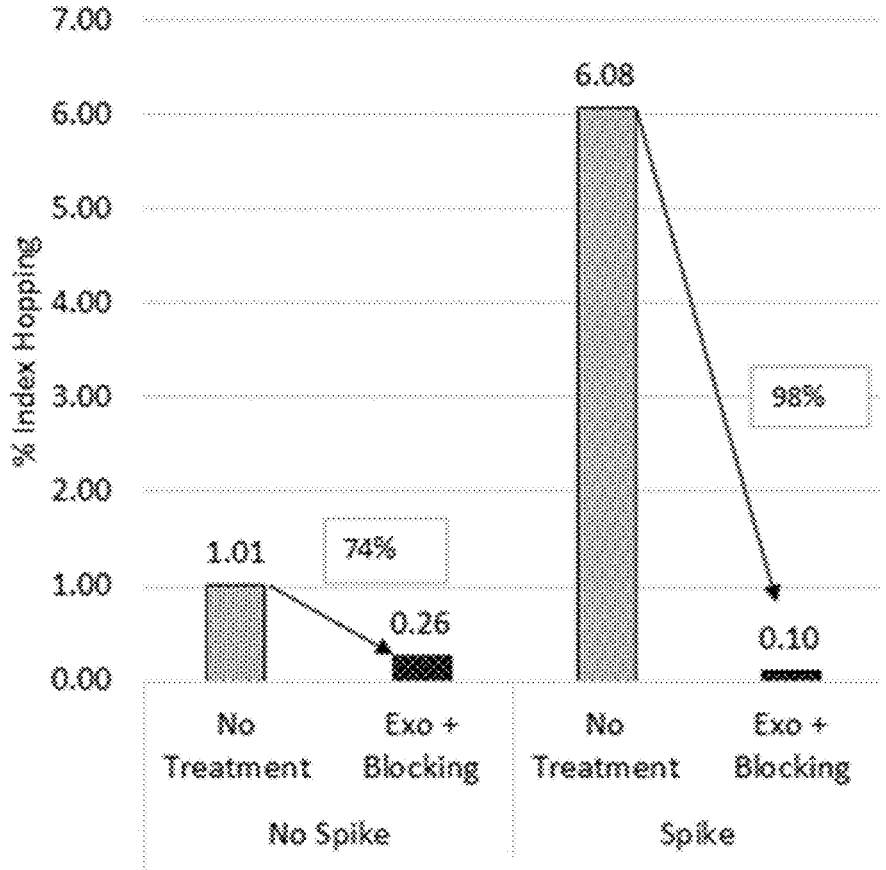

Results of this experiment are summarized in Table 6 below and FIG. 29.

TABLE 6

| Reduction of index hopping by exonuclease treatment with 3' blocking | | | |
|---|---|---|---|
| | Adapter | Index hopping (% of PF clusters) | |
| Library | spike | No Treatment | Exo + 3' Block |
| TruSeq ® PCR-Free | None | 1.01% | 0.26% |
| | Spike | 6.08% | 0.10% |

As illustrated above, index hopping was decreased with exonuclease treatment combined with 3' blocking of DNA libraries.

Example 5: Sample Protocol for Exonuclease Treatment with 3' Blocking of Indexed Libraries with Protected Adapters This protocol explains how to perform an exonuclease treatment with 3' blocking of protected DNA libraries to reduce index hopping. This method is designed to be performed on DNA library pools prior to the denaturation step and subsequent cluster generation using the Illumina HiSeq® 4000 and similar sequencing platforms utilizing patterned flow cells and ExAmp based clustering (e.g., HiSeq® X and NovaSeq®).

Index hopping has been seen to occur where incorrect index sequences are assigned to the insert sequence resulting in sample misassignment. Performing this treatment on DNA sample pools before running on HiSeq® 4000 should reduce the index hopping levels by some level which cannot at this stage be predicted consistently.

Treatment workflow may be considered to involve four steps: (i) produce DNA sample pool; (ii) perform treatment, (iii) cleanup sample and quantify; and (iv) cluster and sequence sample pool.

Consumables/Equipment: Consumables and equipment may be supplied by a sequencing user or manufacture. User supplied consumables may include a DNA library sample pool—30 μl at concentration to be used for denaturation during clustering. The user may also supply freshly prepared 80% ethanol (EtOH).

Table 7 below illustrates some consumables and equipment that may be used.

TABLE 7

| Consumables and Equipment | |
|---|---|
| Consumable/Equipment | Supplier |
| Ethanol 200 proof (absolute) for molecular biology | Sigma-Aldrich, Cat #E7023 |
| Magnetic stand-96 | Life Technologies, Cat #AM10027 |
| Vortexer | General lab supplier |
| 96-well thermal cycler (with heated lid) | General lab supplier |

A sequencing manufacturer may supply EMX (Exonuclease Mix), BMX (Blocking Mix); RSB (Resuspension Buffer), and SPB (Sample Purification Beads).

The EMX may include an exonuclease buffer (NEBuffer 4, NEB Cat #B7004S: 50 mM potassium acetate, 20 mM Tris-acetate, 10 mM magnesium acetate, 1 mM DTT) and Exonuclease V (New England Biolabs, Cat #M0345S/L).

The BMX may include a sequencing premix (Tris buffer, sodium chloride, sucrose, magnesium sulfate, EDTA and Tween 20), a ddNTP mix, Pol19 DNA polymerase, and TDT terminal transferase.

The RSB may include a Tris buffer, pH 8.5.

The SPB may include Agencourt® AMPure® XP beads (Beckman Coulter, Cat #A63880). The SPB should be vortexed before each use. The SPB should be vortexed frequently to make sure that beads are evenly distributed. The SPB should be aspirated and dispensed slowly due to the viscosity of the solution.

Some of the consumables should be stored and prepared as indicated in Table 8 below.

TABLE 8

| Storage and preparation of consumables | | |
|---|---|---|
| Item | Storage | Instructions |
| EMX | −25° C. to −15° C. | Thaw at room temperature, and then place on ice. Return to storage after use |
| BMX | −25° C. to −15° C. | Thaw at room temperature, and then place on ice. Return to storage after use. |

TABLE 8-continued

| | Storage and preparation of consumables | |
|---|---|---|
| Item | Storage | Instructions |
| RSB | 2° C. to 8° C. | Let stand for 30 min to bring to room temperature |
| SPB | 2° C. to 8° C. | Let stand for 30 min to bring to room temperature. |

The following EMX program may be saved on the thermal cycler: (i) choose the preheat lid option and set to 100° C.; (ii) 37° C. for 5 mins; (iii) 70° C. for 30 mins; and (iv) hold at 4° C.

The following BMX program may be saved on the thermal cycler: (i) choose the preheat lid option and set to 100° C.; (ii) 38° C. for 20 mins; (iii) 60° C. for 20 mins; and (iv) hold at 4° C.

The samples may be treated as follows: (i) centrifuge EMX at 600×g for 5 seconds; (ii) add 27 μl of DNA library sample pool to PCR tube; (iii) add 5 μl EMX to each sample in each PCR tube and then mix thoroughly by pipetting up and down; (iv) incubate by placing on the thermal cycler and running the EMX program; (v) centrifuge BMX at 600×g for 5 seconds; (vi) add 32 μl BMX directly to each exonuclease reaction in each PCR tube and then mix thoroughly by pipetting up and down; and (vii) incubate by placing on the thermal cycler and running the BMX program. Each tube contains 64 μl.

The treated pooled sample may be cleaned up as follows: (1) vortex SPB until well-dispersed; (2) add 60 μl SPB to each sample treatment tube and mix thoroughly by pipetting up and down; (3) incubate at room temperature for 5 minutes; (4) place on a magnetic stand and wait until the liquid is clear (2-5 minutes); (5) remove and discard all supernatant from each tube; (6) wash 2 times as follows: (a) add 200 μl freshly prepared 80% EtOH to each tube, (b) incubate on the magnetic stand for 30 seconds, and (c) remove and discard all supernatant from each tube; (7) use a 20 μl pipette to remove residual EtOH from each tube; (8) air-dry on the magnetic stand for 5 minutes; (9) add 22.5 μl RSB to each tube; (10) remove from the magnetic stand and then mix thoroughly by pipetting up and down; (11) incubate at room temperature for 2 minutes; (12) place on a magnetic stand and wait until the liquid is clear (2-5 minutes); (13) transfer 20 μl supernatant to a new tube; (14) quantify libraries if required and proceed onto standard clustering for the HiSeq® 4000 platform starting with NaOH denaturation step; and (15) store at −25° C. to −15° C. if not clustering immediately.

Example 6: Reduction of Index Hopping by Exonuclease Treatment with 3' Blocking of Indexed Libraries with Protected Adapters The treatment protocol set forth above in Example 5 was applied in combination with the following materials, equipment and methods for clustering and sequencing on Illumina platform.

Experimental conditions: (1) Human 450 bp NA12878 (Coriell Institute) TrueSeq® PCR-Free library prepared using phosphorothioate-protected adapters loaded at 300 pM; (2) HiSeq® X instrument and Illumina SBS chemistry according to manufacturer's instructions; (3) 550 nm ILS v3 flow cell; (4) ExAmp amplification as previously described; and (5) 50% adapter spike-in: free forked adapter from the Illumina dual adapter plate (DAP) spiked into template library prior to denaturation, neutralization, ExAmp mix addition and clustering.

Figure 30:
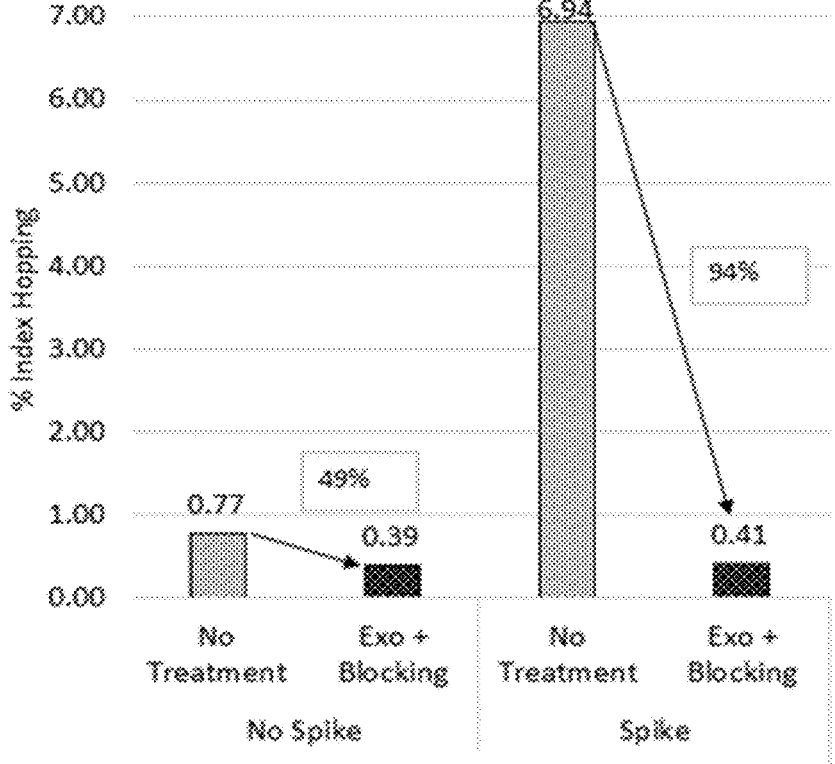

Results of this experiment are summarized in Table 9 below and FIG. 30.

TABLE 9

| Reduction of index hopping by exonuclease treatment of protected adapters with 3' blocking | | | |
|---|---|---|---|
| | Adapter | Index hopping (% of PF clusters) | |
| Library | spike | No Treatment | Exo + 3' Block |
| TruSeq ® PCR-Free | None | 0.77% | 0.39% |
| | Spike | 6.94% | 0.41% |

As illustrated above, index hopping was decreased with exonuclease treatment of protected adapters combined with 3' blocking.

Example 7: Sample Protocol for 3' Blocking of 5' Protected Indexed Libraries

This protocol explains how to perform a 3' blocking treatment of 5' protected DNA libraries, to reduce index hopping. This method is designed to be performed on DNA library pools prior to the denaturation step and subsequent cluster generation using the Illumina HiSeq® 4000 and similar sequencing platforms utilizing patterned flow cells and ExAmp based clustering (e.g., HiSeq® X and NovaSeq®).

Index hopping has been seen to occur where incorrect index sequences are assigned to the insert sequence resulting in sample misassignment. Performing this treatment on DNA sample pools before running on HiSeq® 4000 should reduce the index hopping levels by some level which cannot at this stage be predicted consistently.

Treatment workflow may be considered to involve four steps: (i) produce DNA sample pool; (ii) perform treatment, (iii) cleanup sample and quantify; and (iv) cluster and sequence sample pool.

Consumables/Equipment: Consumables and equipment may be supplied by a sequencing user or manufacture. User supplied consumables may include a DNA library sample pool—30 μl at concentration to be used for denaturation during clustering. The user may also supply freshly prepared 80% ethanol (EtOH).

Table 10 below illustrates some consumables and equipment that may be used.

TABLE 10

| Consumables and Equipment | |
|---|---|
| Consumable/Equipment | Supplier |
| Ethanol 200 proof (absolute) for molecular biology | Sigma-Aldrich, Cat #E7023 |
| Magnetic stand-96 | Life Technologies, Cat #AM10027 |
| Vortexer | General lab supplier |
| 96-well thermal cycler (with heated lid) | General lab supplier |

A sequencing manufacturer may supply BMX (Blocking Mix), EMX (Exonuclease Mix), RSB (Resuspension Buffer), and SPB (Sample Purification Beads).

The EMX may include an exonuclease buffer (67 mM Glycine-KOH, 2.5 mM MgCl$_2$, 50 μg/ml BSA) and Lambda Exonuclease (New England Biolabs, Cat #M0262S/L).

The BMX may include a sequencing premix (Tris buffer, sodium chloride, sucrose, magnesium sulfate, EDTA and Tween 20), a ddNTP mix, Poll9 DNA polymerase, and TDT terminal transferase.

The RSB may include a Tris buffer, pH 8.5.

The SPB may include AgenCourt® AMPure® XP beads (Beckman Coulter, Cat #A63880). The SPB should be vortexed before each use. The SPB should be vortexed frequently to make sure that beads are evenly distributed. The SPB should be aspirated and dispensed slowly due to the viscosity of the solution.

Some of the consumables should be stored and prepared as indicated in Table 11 below.

TABLE 11

| Storage and preparation of consumables | | |
| --- | --- | --- |
| Item | Storage | Instructions |
| BMX | −25° C. to −15° C. | Thaw at room temperature, and then place on ice. Return to storage after use. |
| EMX | −25° C. to −15° C. | Thaw at room temperature, and then place on ice. Return to storage after use. |
| RSB | 2° C. to 8° C. | Let stand for 30 min to bring to room temperature. |
| SPB | 2° C. to 8° C. | Let stand for 30 min to bring to room temperature. |

The following EMX program may be saved on the thermal cycler: (i) choose the preheat lid option and set to 100° C.; (ii) 37° C. for 30 mins; (iii) 75° C. for 10 mins; and (iv) hold at 4° C.

The following BMX program may be saved on the thermal cycler: (i) choose the preheat lid option and set to 100° C.; (ii) 38° C. for 20 mins; (iii) 60° C. for 20 mins; and (iv) hold at 4° C.

For the 3' blocking treatment, the samples may be treated as follows: (i) centrifuge BMX at 600×g for 5 seconds; (ii) add 30 μl of 5' protected DNA library sample pool to PCR tube; (iii) add 30 μl BMX to each sample in each PCR tube and then mix thoroughly by pipetting up and down; (iv) incubate by placing on the thermal cycler and running the BMX program. Each tube contains 60 μl.

For the 3' blocking plus exonuclease treatment, the samples may be treated as follows: (i) centrifuge EMX at 600×g for 5 seconds; (ii) add 27 μl of 5' protected DNA library sample pool to PCR tube; (iii) add 5 μl EMX to each sample in each PCR tube and then mix thoroughly by pipetting up and down; (iv) incubate by placing on the thermal cycler and running the EMX program; (v) centrifuge BMX at 600×g for 5 seconds; (vi) add 32 μl BMX directly to each exonuclease reaction in each PCR tube and then mix thoroughly by pipetting up and down; and (vii) incubate by placing on the thermal cycler and running the BMX program. Each tube contains 64 μl.

The treated pooled sample may be cleaned up as follows: (1) vortex SPB until well-dispersed; (2) add 60 μl SPB to each sample treatment tube and mix thoroughly by pipetting up and down; (3) incubate at room temperature for 5 minutes; (4) place on a magnetic stand and wait until the liquid is clear (2-5 minutes); (5) remove and discard all supernatant from each tube; (6) wash 2 times as follows: (a) add 200 μl freshly prepared 80% EtOH to each tube, (b) incubate on the magnetic stand for 30 seconds, and (c) remove and discard all supernatant from each tube; (7) use a 20 μl pipette to remove residual EtOH from each tube; (8) air-dry on the magnetic stand for 5 minutes; (9) add 22.5 μl RSB to each tube; (10) remove from the magnetic stand and then mix thoroughly by pipetting up and down; (11) incubate at room temperature for 2 minutes; (12) place on a magnetic stand and wait until the liquid is clear (2-5 minutes); (13) transfer 20 μl supernatant to a new tube; (14) quantify libraries if required and proceed onto standard clustering for the HiSeq® 4000 platform starting with NaOH denaturation step; and (15) store at −25° C. to −15° C. if not clustering immediately.

Example 8: Reduction of Index Hopping by 3' Blocking of 5' Protected Indexed Libraries The treatment protocol set forth above in Example 7 was applied in combination with the following materials, equipment and methods for clustering and sequencing on Illumina platform.

Experimental conditions: (1) Human 450 bp NA12878 (Coriell Institute) TrueSeq® Nano library generated using 5' protected P5 and P7 primers loaded at 300 pM; (2) HiSeq® X instrument and Illumina SBS chemistry according to manufacturer's instructions; (3) 550 nm ILS v3 flow cell; (4) ExAmp amplification as previously described; and (5) 50% adapter spike-in: free forked adapter from the Illumina dual adapter plate (DAP) spiked into template library prior to denaturation, neutralization, ExAmp mix addition and clustering.

Figure 31:
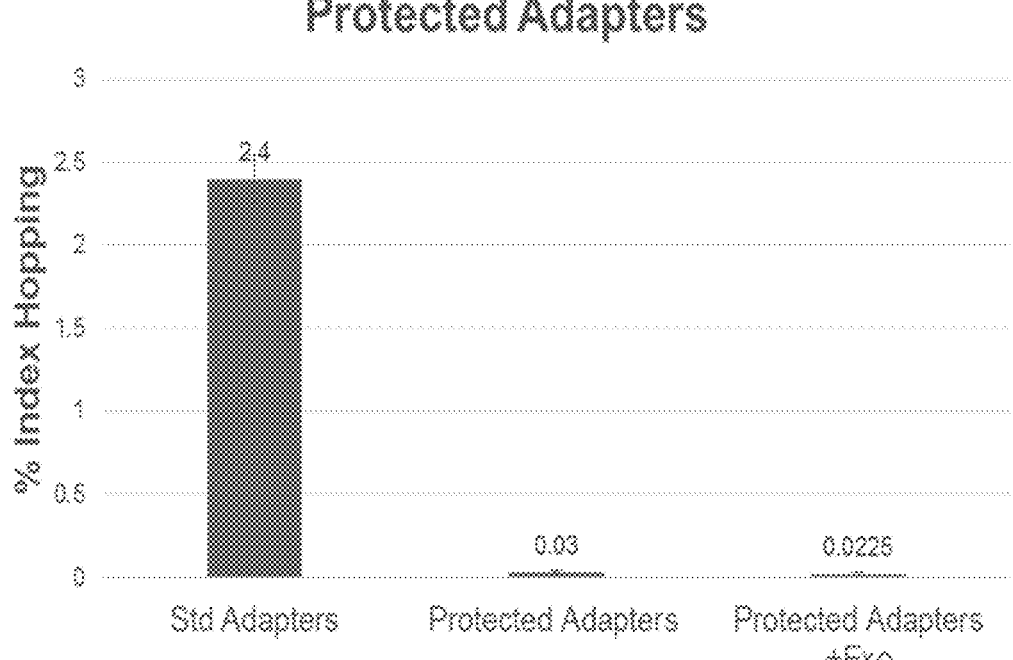
FIG. 31 shows the effect of combined exonuclease and 3' blocking treatment on the rates of index hopping in Illumina TruSeq® Nano (PCR) library preparation work flow, comparing the performance of standard adapters and PCR-protected adapters according to the present invention.

Results of this experiment are summarized in Table 12 below and FIG. 31.

TABLE 12

| Reduction of index hopping by PCR protection with 3' blocking | |
| --- | --- |
| Library | % Index Hopping |
| Standard Adapters | 2.4 |
| 5', 3' Protected Adapters | 0.03 |
| Protected Adapters + Exonuclease | 0.023 |

As illustrated above, index hopping was decreased significantly relative to standard adapters by employing 5' protected and 3' blocked adapters as described herein. Optional exonuclease treatment may have further reduced index hopping.

Any patent, patent application (whether published or not), or other literature referred to herein in hereby incorporated herein in its respective entirety or in part to the extent that it does not conflict with the disclosure presented herein.

It will be apparent to those skilled in the art that various modifications and variations may be made to the present inventive technology without departing from the spirit and scope of the disclosure. Since modifications, combinations, sub-combinations and variations of the disclosed embodiments incorporating the spirit and substance of the inventive technology may occur to persons skilled in the art, the inventive technology should be construed to include everything within the scope of the appended claims and their equivalents.

What is claimed is:

1. An oligonucleotide adapter for ligating to a target polynucleotide prior to sequencing, comprising:

a first oligonucleotide strand having a 5' end and a 3' end; and a second oligonucleotide strand having a 5' end and a 3' end, wherein a region of the 5' end of the first strand comprises nucleotides complementary to nucleotides in a region of the 3' end of the second strand such that the complementary regions are double-stranded, wherein a region of the 3' end of the first strand and a
region of the 5' end of the second strand are sufficiently
non-complementary to be single-stranded, wherein at least one of the first strand and the second
strand comprises a library-specific index tag sequence, wherein the 3' end of the first strand is modified to prevent
digestion by an enzyme having 3' exonuclease activity
and wherein the 5' end of the second strand is modified
to prevent digestion by an enzyme having 5' exonu-
clease activity, and wherein the 5' end of the first strand is susceptible to
exonuclease activity and wherein the 3' end of the
second strand is susceptible to exonuclease activity.

2. An oligonucleotide adapter according to claim 1,
wherein the double stranded region is double-stranded under
standard ligation conditions, and wherein the single-
stranded regions are single stranded under standard ligation
conditions.

3. An oligonucleotide adapter according to claim 1, wherein the 3' end of the first strand comprises a phos-
phorothioate bond, wherein a single stranded DNA
binding protein is bound to the 3' end of the first strand,
wherein biotin is attached to the 3' end of the first
strand, wherein an antibody is attached to the 3' end of
the first strand; and wherein the 5' end of the second strand comprises a
phosphorothioate bond, wherein a single stranded DNA
binding protein is bound to the 5' end of the second,
wherein biotin is attached to the 5' end of the second
strand, or wherein an antibody is attached to the 5' end
of the second strand.

4. The oligonucleotide adapter according to claim 1,
wherein the 3' end of the first strand comprises three
phosphorothioate bonds, and wherein the 5' end of the
second strand comprises three phosphorothioate bonds.

5. A kit comprising:
the oligonucleotide adapter according to claim 1; and
an exonuclease.

6. A kit according to claim 5, wherein the exonuclease
comprises 3' exonuclease activity and 5' exonuclease activ-
ity.

7. A kit according to claim 5, wherein the exonuclease
comprises activity for double-stranded DNA without nick-
ing.

8. A kit according to claim 5, wherein the exonuclease
comprises a first exonuclease having 3' exonuclease activity
and a second exonuclease having 5' exonuclease activity.

9. A kit according to claim 5, wherein the exonuclease is
Exonuclease V.

10. A composition comprising the oligonucleotide adapter
according to claim 1; and
an exonuclease.

11. A composition comprising:
the oligonucleotide adapter according to claim 1; and
a plurality of double stranded target polynucleotide frag-
ments, each fragment having a first end and a second
end.

12. A composition according to claim 11, further com-
prising a ligase.

13. A composition comprising:
a plurality of polynucleotides comprising a first adapter-
target-second adapter sequence, wherein the first
adapter and second adapter comprises the oligonucle-
otide adapter of claim 1;
wherein the target sequence is double stranded, a region
of the first adapter in proximity to the target is double
stranded, a region of the second adapter in proximity to
the target is double stranded, a region of the first
adapter distal to the target comprises two single strands,
each having an end, and a region of the second adapter
distal to the target comprises two single strands, each
having an end.

14. A composition according to claim 13, wherein the
each of the two single strands of the first and second adapters
comprises a phosphorothioate bond.

15. A composition according to claim 13, wherein the
each of the two single strands of the first and second adapters
comprises three phosphorothioate bonds.

16. A composition according to claim 13, further com-
prising:
the oligonucleotide adapter that is not attached to the
target.

17. A composition according to claim 13, further com-
prising an exonuclease.

* * * * *